(12) United States Patent
Lu et al.

(10) Patent No.: US 9,776,994 B2
(45) Date of Patent: Oct. 3, 2017

(54) PYRAZOLINE DERIVATIVES AS INSECTICIDAL COMPOUNDS

(71) Applicant: SYNGENTA PARTICIPATIONS AG, Basel (CH)

(72) Inventors: Long Lu, Shanghai (CN); Jerome Yves Cassayre, Stein (CH); Guillaume Berthon, Stein (CH); Myriem El Qacemi, Stein (CH); Yaming Wu, Shanghai (CN)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/762,319

(22) PCT Filed: Jan. 23, 2014

(86) PCT No.: PCT/CN2014/071207
§ 371 (c)(1),
(2) Date: Jul. 21, 2015

(87) PCT Pub. No.: WO2014/114250
PCT Pub. Date: Jul. 31, 2014

(65) Prior Publication Data
US 2015/0353532 A1 Dec. 10, 2015

(30) Foreign Application Priority Data

Jan. 23, 2013 (WO) ................ PCT/CN2013/070902

(51) Int. Cl.
*C07D 413/12* (2006.01)
*C07D 231/06* (2006.01)
(Continued)

(52) U.S. Cl.
CPC .......... *C07D 413/12* (2013.01); *A01N 43/16* (2013.01); *A01N 43/56* (2013.01); *A01N 43/58* (2013.01);
(Continued)

(58) Field of Classification Search
None
See application file for complete search history.

(56) References Cited

U.S. PATENT DOCUMENTS 4,999,368 A 3/1991 Delany
2011/0269804 A1* 11/2011 Cassayre ................ A01N 43/36
514/362

FOREIGN PATENT DOCUMENTS

EP 1731512 A1 12/2006
EP 2172448 A1 4/2010
(Continued)

Primary Examiner — Kamal Saeed
(74) Attorney, Agent, or Firm — R. Kody Jones

(57) ABSTRACT

The present invention relates to compounds of formula (I) wherein P is selected from P1 and P2, or P and $R^5$ together are P3 or P is a heterocycle H, selected from H1 to H9 wherein $Y^1$, $Y^2$ and $Y^3$ are independently of each other C—H, C—$R^5$, or nitrogen; and $G^1$, $G^2$, $G^3$, Z, $R^1$, $R^2$, $R^3$, $R^4$, $R^5$, $R^{6a}$, $R^{6b}$, $R^7$, $R^8$, $R^9$, $R^{10}$, $R^{11}$, p, n and k are as defined in the claims. The invention also relates to methods of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I).

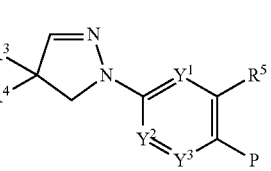

(I)

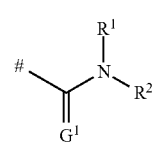

P1

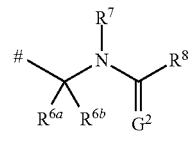

P2

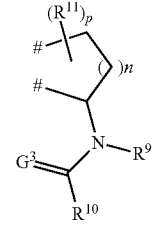

P3

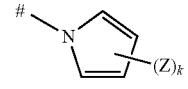

H1

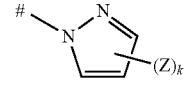

H2

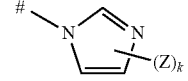

H3

H4

(Continued)

-continued

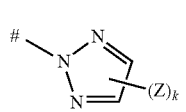

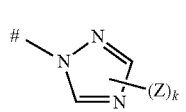

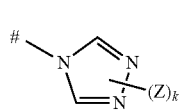

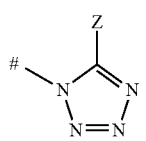

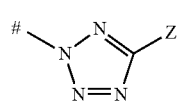

12 Claims, No Drawings

(51) Int. Cl.
*C07D 409/12* (2006.01)
*A01N 43/56* (2006.01)
*A01N 43/80* (2006.01)
*A01N 43/58* (2006.01)
*A01N 43/60* (2006.01)
*A01N 43/90* (2006.01)
*A01N 53/00* (2006.01)
*A01N 43/16* (2006.01)
*A01N 43/78* (2006.01)

(52) U.S. Cl.
CPC ............. *A01N 43/60* (2013.01); *A01N 43/78* (2013.01); *A01N 43/80* (2013.01); *A01N 43/90* (2013.01); *A01N 53/00* (2013.01); *C07D 231/06* (2013.01); *C07D 409/12* (2013.01)

(56) References Cited

FOREIGN PATENT DOCUMENTS

| WO | 2010/020522 A1 | 2/2010 |
| WO | 2010/149506 A1 | 12/2010 |
| WO | 2011/051455 A1 | 5/2011 |
| WO | 2011/101229 A1 | 8/2011 |
| WO | 2012/067235 A1 | 5/2012 |
| WO | PCTCN2014071207 | 6/2015 |

\* cited by examiner

PYRAZOLINE DERIVATIVES AS INSECTICIDAL COMPOUNDS

This application is a 371 filing of International Application No. PCT/CN2014/071207, filed Jan. 23, 2014, which claims priority benefit to International Application No. PCT/CN2013/070902 filed Jan. 23, 2013, the contents of all of which are incorporated herein by reference.

The present invention relates to certain pyrazoline derivatives, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain isoxazoline derivatives with insecticidal properties are disclosed, for example, in EP 1,731,512. However there is a continuing need to find new biologically active compounds as well as new biologically active compounds displaying superior properties for use as agrochemical active ingredients, for example greater biological activity, different spectrum of activity, increased safety profile, or increased biodegradability.

It has now surprisingly been found that certain pyrazoline derivatives have highly potent insecticidal properties.

The present invention provides compounds of formula (I)

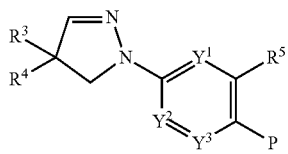

(I)

wherein

P is selected from P1 and P2, or P and $R^5$ together are P3

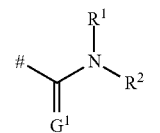

P1

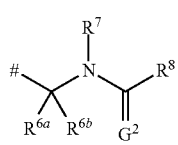

P2

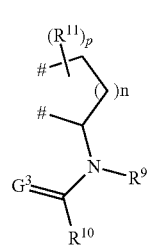

P3 or P is a heterocycle H, selected from H1 to H9

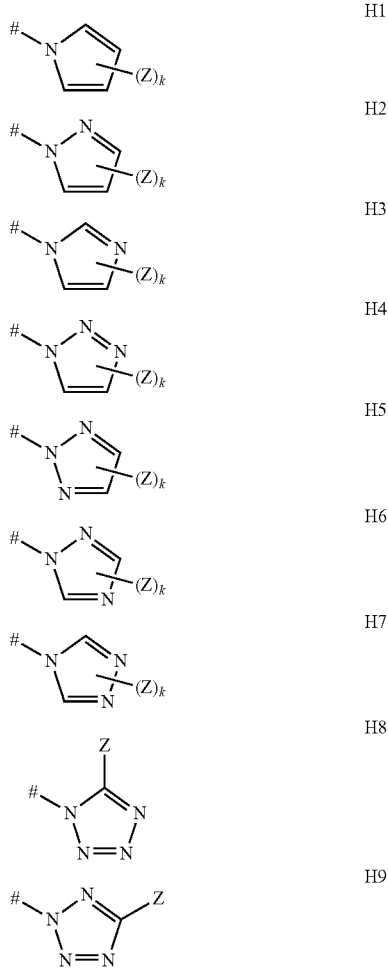

$Y^1$, $Y^2$, and $Y^3$ are independently of each other C—H, C—$R^5$, or nitrogen;

$G^1$ is oxygen or sulfur;
$G^2$ is oxygen or sulfur;
$G^3$ is oxygen or sulfur;
$R^1$ is hydrogen, $C_1$-$C_8$alkyl, $C_1$-$C_8$alkoxy, $C_1$-$C_8$alkylcarbonyl, or $C_1$-$C_8$alkoxycarbonyl;
$R^2$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-$C_1$-$C_4$alkylene or $C_3$-$C_{10}$cycloalkyl-$C_1$-$C_4$alkylene substituted by one to five $R^{13}$, aryl-$C_1$-$C_4$alkylene- or aryl-$C_1$-$C_4$alkylene-substituted by one to five $R^{14}$, heterocyclyl-$C_1$-$C_4$alkylene- or heterocyclyl-$C_1$-$C_4$alkylene-substituted by one to five $R^{14}$, aryl or aryl substituted by one to five $R^{14}$, heterocyclyl or heterocyclyl substituted by one to five $R^{14}$, $C_1$-$C_8$alkylaminocarbonyl-$C_1$-$C_4$alkylene, $C_1$-$C_8$haloalkylaminocarbonyl-$C_1$-$C_4$alkylene, $C_3$-$C_8$cycloalkyl-aminocarbonyl-$C_1$-$C_4$ alkylene, aryl-$CH_2$-aminocarbonyl-$C_1$-$C_4$alkylene or aryl-$CH_2$-aminocarbonyl-$C_1$-$C_4$alkylene wherein the aryl is substituted by one to five $R^{14}$, $C_1$-$C_8$alkylaminocarbonyl, $C_1$-$C_8$haloalkylaminocarbonyl, $C_3$-$C_6$cycloalkylaminocarbonyl, $C_1$-$C_6$alkyl-O—N=CH—, or $C_1$-$C_6$haloalkyl-O—N=CH—;
$R^3$ is $C_1$-$C_8$haloalkyl;
$R^4$ is aryl or aryl substituted by one to five $R^{15}$, or heteroaryl or heteroaryl substituted by one to five $R^{15}$;

each $R^5$ is independently hydrogen, halogen, cyano, nitro, $C_1$-$C_8$alkyl, $C_1$-$C_8$haloalkyl, $C_1$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl, or two $R^5$ on adjacent carbon atoms together form a —CH=CH—CH=CH— bridge or a —N=CH—CH=CH— bridge;

$R^{6a}$ and $R^{6b}$ are each independently hydrogen, halogen, cyano, $C_1$-$C_8$alkyl, $C_1$-$C_8$haloalkyl, or $C_3$-$C_8$cycloalkyl, or $R^{6a}$ and $R^{6b}$ together with the carbon atom to which they are attached may form a 3 to 6-membered carbocyclic ring;

$R^7$ is hydrogen, $C_1$-$C_8$alkyl, $C_1$-$C_8$alkoxy, $C_1$-$C_8$alkylcarbonyl, or $C_1$-$C_8$alkoxycarbonyl;

$R^8$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-$C_1$-$C_4$alkylene or $C_3$-$C_{10}$cycloalkyl-$C_1$-$C_4$alkylene substituted by one to five $R^{13}$, aryl-$C_1$-$C_4$alkylene- or aryl-$C_1$-$C_4$alkylene-substituted by one to five $R^{14}$, heterocyclyl-$C_1$-$C_4$alkylene- or heterocyclyl-$C_1$-$C_4$alkylene-substituted by one to five $R^{14}$, aryl or aryl substituted by one to five $R^{14}$, or heterocyclyl or heterocyclyl substituted by one to five $R^{14}$, each $R^9$ is independently hydrogen, $C_1$-$C_8$alkyl, $C_1$-$C_8$alkoxy, $C_1$-$C_8$alkylcarbonyl, or $C_1$-$C_8$alkoxycarbonyl;

$R^{10}$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-$C_1$-$C_4$alkylene or $C_3$-$C_{10}$cycloalkyl-$C_1$-$C_4$alkylene substituted by one to five $R^{13}$, aryl-$C_1$-$C_4$alkylene- or aryl-$C_1$-$C_4$alkylene-substituted by one to five $R^{14}$, heterocyclyl-$C_1$-$C_4$alkylene- or heterocyclyl-$C_1$-$C_4$alkylene-substituted by one to five $R^{14}$, aryl or aryl substituted by one to five $R^{14}$, heterocyclyl or heterocyclyl substituted by one to five $R^{14}$;

each $R^{11}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or $C_1$-$C_8$alkoxycarbonyl;

each $R^{12}$ is independently halogen, cyano, nitro, hydroxy, amino, $C_1$-$C_8$alkylamino, $(C_1$-$C_8$alkyl$)_2$amino, $C_1$-$C_8$alkylcarbonylamino, $C_1$-$C_8$haloalkylcarbonylamino, $C_1$-$C_8$alkoxy, $C_1$-$C_8$haloalkoxy, aryloxy or aryloxy substituted by one to five $R^{16}$, aryloxy-$C_1$-$C_4$alkylene or aryloxy-$C_1$-$C_4$alkylene wherein the aryl moiety is substituted by one to five $R^{16}$, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, aryl-$C_1$-$C_4$alkylthio or aryl-$C_1$-$C_4$alkylthio wherein the aryl moiety is substituted by one to five $R^{16}$;

each $R^{13}$ is independently halogen, cyano, $C_1$-$C_8$alkyl, $C_2$-$C_8$alkenyl, $C_2$-$C_8$alkynyl, or $C_1$-$C_8$alkoxy, $C_1$-$C_8$akoxycarbonyl, or two $R^{13}$ are together $R^{19}$—O—N=;

each $R^{14}$ is independently halogen, cyano, nitro, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkylene, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylaminosulfonyl, $(C_1$-$C_8$alkyl$)_2$aminosulfonyl, $C_1$-$C_8$alkylcarbonyl, $C_1$-$C_8$haloalkylcarbonyl, $C_1$-$C_8$alkoxycarbonyl, $C_8$haloalkoxycarbonyl, aryl or aryl substituted by one to five $R^{16}$, heterocyclyl or heterocyclyl substituted by one to five $R^{16}$, aryl-$C_1$-$C_4$alkylene or aryl-$C_1$-$C_4$alkylene wherein the aryl moiety is substituted by one to five $R^{16}$, heterocyclyl-$C_1$-$C_4$alkylene or heterocyclyl-$C_1$-$C_4$alkylene wherein the heterocyclyl moiety is substituted by one to five $R^{16}$, aryloxy or aryloxy substituted by one to five $R^{16}$, or aryloxy-$C_1$-$C_4$alkylene or aryloxy-$C_1$-$C_4$alkylene wherein the aryl moiety is substituted by one to five $R^{16}$ or two $R^{14}$ are together =O;

each $R^{15}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or $C_1$-$C_8$alkoxycarbonyl;

each $R^{16}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

each $R^{19}$ is hydrogen, $C_1$-$C_8$alkyl or $C_1$-$C_8$haloalkyl;

each Z is independently halogen, cyano, $C_1$-$C_8$alkyl or $C_1$-$C_8$alkyl substituted by one to five $R^{12}$, nitro, hydroxyl, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;

k is 0, 1, or 2;

n is 1 or 2;

p is 0, 1, 2, 3, 4, or 5;

or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds. For example, a tautomer of $C_1$-$C_6$alkyl-O—N=CH—NH—C(=O)— is $C_1$-$C_6$alkyl-O—NH—CH=N—C(=O)—.

The compounds of the invention include N-oxides and salts. The compounds of the invention may contain one or more additional asymmetric carbon atoms and may exist as enantiomers (or as pairs of diastereoisomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —CH$_2$—, —CH$_2$—CH$_2$—, —CH(CH$_3$)—, —CH$_2$—CH$_2$—CH$_2$—, —CH(CH$_3$)—CH$_2$—, or —CH(CH$_2$CH$_3$)—. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. 1.2.4 triazoyl), furanyl, thiophenyl, oxazolyl, isoxazolyl, oxadiazolyl, thiazolyl, isothiazolyl, tetrazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene-) are defined to include heteroaryl groups and in addition their unsaturated or partially unsaturated analogues. Examples of monocyclic groups include isoxazolyl, thietanyl, pyrrolidinyl, tetrahydrofuranyl, [1,3]dioxolanyl, piperidinyl, piperazinyl, [1,4]dioxanyl, morpholinyl, thiolanyl, oxetanyl, tetrahydropyranyl, 3-oxo-isoxazolidinyl-, 2,5-dioxo-1-pyrrolidinyl-, 2-oxo-1-pyrrolidinyl-, 4-oxo-1,3-oxazinanyl, 1-oxa-3,4-diazolyl, including their oxidised versions such as 1-oxo-thietanyl and 1,1-dioxo-thietanyl, thiolanyl 1-oxide, thiolanyl 1,1-dioxide, Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents. Heterocyclyl groups (and heteroaryl groups) according to the present invention do not contain adjacent oxygen atoms, adjacent sulphur atoms, or adjacent sulphur and oxygen atoms;

Preferred values of P, $Y^1$, $Y^2$, $Y^3$, $Y^4$, $G^1$, Z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, k, n, p, and q are, in any combination (including combinations of preferred values with the original values) as set out below.

Preferably H is H2 or H6, most preferably H6.

Preferably $Y^1$ is C—H, C—$R^5$ or nitrogen, $Y^2$ and $Y^3$ are independently C—H or nitrogen, wherein no more than two of $Y^1$, $Y^2$ and $Y^3$ are nitrogen, $Y^2$ and $Y^3$ are not both nitrogen and when $Y^1$ is C—$R^5$ the two adjacent $R^5$ together form a —CH=CH—CH=CH— bridge or a —N=CH—CH=CH— bridge, more preferably $Y^1$ is C—H or nitrogen, $Y^2$ and $Y^3$ are independently C—H or nitrogen, wherein no more than two of $Y^1$, $Y^2$ and $Y^3$ are nitrogen and wherein $Y^2$ and $Y^3$ are not both nitrogen, more preferably $Y^1$ is C—H, $Y^2$ is C—H or nitrogen, $Y^3$ is C—H or nitrogen, wherein $Y^2$ and $Y^3$ are not both nitrogen, most preferably $Y^1$ is C—H, $Y^2$ is C—H, and $Y^3$ is C—H.

Preferably $G^1$ is oxygen.

Preferably $G^2$ is oxygen.

Preferably $G^3$ is oxygen.

Preferably $G^1$, $G^2$ and $G^3$ are oxygen.

Preferably $R^1$ is hydrogen, methyl, ethyl, methylcarbonyl, or methoxycarbonyl, more preferably hydrogen, methyl or ethyl, most preferably hydrogen.

Preferably $R^2$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-C($R^{17}$)($R^{18}$)— or $C_3$-$C_{10}$cycloalkyl-C($R^{17}$)($R^{18}$)— wherein the cycloalkyl is substituted by one to five $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)— or heterocyclyl-C($R^{17}$)($R^{18}$)— wherein the heterocyclyl is substituted by one to five $R^{14}$, aryl or aryl substituted by one to five $R^{14}$, heterocyclyl or heterocyclyl substituted by one to five $R^{14}$, $C_1$-$C_8$alkylaminocarbonyl-$CH_2$—, $C_1$-$C_8$haloalkylaminocarbonyl-$CH_2$—, $C_3$-$C_8$cycloalkylaminocarbonyl-$CH_2$—, aryl-$CH_2$-aminocarbonyl-$CH_2$— or aryl-$CH_2$-aminocarbonyl-$CH_2$— wherein the aryl is substituted by one to five $R^{14}$, $C_1$-$C_8$alkylaminocarbonyl, $C_1$-$C_8$haloalkylaminocarbonyl, $C_3$-$C_6$cycloalkylaminocarbonyl, $C_1$-$C_6$alkyl-O—N=CH—, or $C_1$-$C_6$haloalkyl-O—N=CH—;

wherein heterocyclyl is a 4 to 7-membered heterocyclic ring containing one to three heteroatoms independently selected from O, S, SO, $SO_2$, N, and N($R^{20}$) as ring atoms.

wherein aryl is phenyl;

wherein $R^{17}$ and $R^{18}$ are independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl;

or $R^{17}$ and $R^{18}$ together form a three to six membered carbocycle;

and wherein $R^{20}$ is hydrogen or $R^{14}$.

More preferably $R^2$ is $C_1$-$C_6$alkyl or $C_1$-$C_6$alkyl substituted by one to five $R^{12}$, $C_3$-$C_8$cycloalkyl or $C_3$-$C_8$cycloalkyl substituted by one to five $R^{13}$, $C_3$-$C_8$cycloalkyl-C($R^{17}$)($R^{18}$)— or $C_3$-$C_8$cycloalkyl-C($R^{17}$)($R^{18}$)— wherein the cycloalkyl is substituted by one to five $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, heterocyclyl, $C_1$-$C_6$alkylaminocarbonyl-$CH_2$—, $C_1$-$C_6$haloalkylaminocarbonyl-$CH_2$—, $C_3$-$C_8$cycloalkyl-aminocarbonyl-$CH_2$—, aryl-$CH_2$-aminocarbonyl-$CH_2$— or aryl-$CH_2$-aminocarbonyl-$CH_2$— wherein the aryl is substituted by one to five $R^{14}$, $C_1$-$C_6$alkylaminocarbonyl, $C_1$-$C_6$haloalkylaminocarbonyl, $C_3$-$C_6$cycloalkylaminocarbonyl-, $C_1$-$C_4$alkyl-O—N=CH— or $C_1$-$C_4$haloalkyl-O—N=CH—;

wherein heterocyclyl is a 4- to 6-membered saturated or partially saturated heterocyclic ring containing one or two heteroatoms independently selected from O, S, SO, $SO_2$, N and N($R^{20}$) as ring atoms, wherein one or two carbon ring atoms are optionally substituted by oxo, and wherein the ring is optionally substituted by one or two $R^{14}$, or heterocyclyl is a 5- or 6-membered heteroaryl ring containing one to three heteroatoms selected from O, N and S as ring atoms, wherein the ring is optionally substituted by one to three $R^{14}$;

wherein aryl is phenyl;
wherein $R^{17}$ is hydrogen or $C_1$-$C_4$alkyl;
wherein $R^{18}$ is independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl;
or $R^{17}$ and $R^{18}$ together form a 3- to 6-membered carbocycle;
and wherein $R^{20}$ is hydrogen or $R^{14}$.

More preferably $R^2$ is $C_1$-$C_6$alkyl or $C_1$-$C_6$alkyl substituted by one to five $R^{12}$, $C_3$-$C_8$cycloalkyl or $C_3$-$C_8$cycloalkyl substituted by one to five $R^{13}$, $C_3$-$C_8$cycloalkyl-C($R^{17}$)($R^{18}$)— or $C_3$-$C_8$cycloalkyl-C($R^{17}$)($R^{18}$)— wherein the cycloalkyl is substituted by one to five $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, heterocyclyl, $C_1$-$C_6$alkylaminocarbonyl-$CH_2$—, $C_1$-$C_6$haloalkylaminocarbonyl-$CH_2$—, $C_3$-$C_8$cycloalkyl-aminocarbonyl-$CH_2$—, aryl-$CH_2$-aminocarbonyl-$CH_2$— or aryl-$CH_2$-aminocarbonyl-$CH_2$— wherein the aryl is substituted by one to five $R^{14}$, $C_1$-$C_6$alkylaminocarbonyl-, $C_3$-$C_6$cycloalkylaminocarbonyl-, $C_1$-$C_4$alkyl-O—N=CH—, or $C_1$-$C_4$haloalkyl-O—N=CH—;

wherein heterocyclyl is a 4- or 5-membered saturated heterocyclic ring containing one heteroatom independently selected from O, S, SO, and $SO_2$ as ring atoms, wherein the ring is optionally substituted by one or two methyl;

or heterocyclyl is a 5 or 6-membered saturated or partially saturated heterocyclic ring containing one or two heteroatoms selected from N($R^{20}$), N, S and O as ring atoms, wherein one or two carbon ring atoms are optionally substituted by oxo;

or heterocycyl is a 6-membered heteroaryl ring containing one to three heteroatoms selected from O, N and S as ring atoms, wherein the ring is optionally substituted by one to three groups independently selected from halogen, cyano, $C_1$-$C_4$alkyl, $C_1$-$C_4$haloalkyl, $C_1$-$C_4$alkoxy, $C_1$-$C_4$haloalkoxy and $C_3$-$C_6$cycloalkyl;

wherein each $R^{12}$ is independently halogen, $C_1$-$C_8$alkoxy, $C_1$-$C_8$haloalkoxy-mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;

wherein each $R^{13}$ is independently halogen, cyano, $C_1$-$C_4$alkyl, or two $R^{13}$ are together $R^{19}$—O—N=;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen or $C_1$-$C_4$alkyl;

wherein $R^{18}$ is independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl;

or $R^{17}$ and $R^{18}$ together form a three to six membered carbocycle;

wherein $R^{19}$ is H or $C_1$-$C_4$alkyl;

and wherein $R^{20}$ is hydrogen, $C_1$-$C_4$alkyl, $C_2$-$C_4$alkenyl, $C_2$-$C_4$alkynyl, $C_3$-$C_6$cycloalkyl, $C_3$-$C_6$cycloalkyl-$CH_2$, $C_1$-$C_4$haloalkyl, $C_1$-$C_4$alkoxyalkyl, $C_1$-$C_4$haloalkoxyalkyl, $C_1$-$C_4$alkoxy-$C_1$-$C_4$alkyl, $C_1$-$C_4$alkoxy, $C_1$-$C_4$alkylcarbonyl, $C_1$-$C_4$haloalkylcarbonyl, phenyl-$CH_2$-alkyl- or phenyl-$CH_2$— wherein the phenyl moiety is substituted by one to three groups independently selected from halogen, cyano, methyl, halomethyl, methoxy and halomethoxy, furanyl or furanyl substituted by one to three groups independently selected from halogen, cyano, methyl, halomethyl, methoxy and halomethoxy, thietanyl, oxetanyl, 1-oxo-thietanyl, or 1,1-dioxo-thietanyl.

More preferably $R^2$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_8$cycloalkyl or $C_3$-$C_8$cycloalkyl substituted by one to three $R^{13}$, $C_3$-$C_8$cycloalkyl-C($R^{17}$)($R^{18}$)— or $C_3$-$C_8$cycloalkyl-C($R^{17}$)($R^{18}$)— wherein the cycloalkyl is substituted by one to three groups $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, heterocyclyl, $C_1$-$C_4$alkylaminocarbonyl-$CH_2$—, $C_1$-$C_4$haloalkylaminocarbonyl-$CH_2$—, $C_1$-$C_6$alkylaminocarbonyl-, $C_1$-$C_4$alkyl-O—N=CH—, or $C_1$-$C_4$haloalkyl-O—N=CH—;

wherein heterocyclyl is a 4- or 5-membered saturated heterocyclic ring containing one heteroatom independently selected from O, S, SO, and $SO_2$ as ring atoms, wherein the ring is optionally substituted by one or two methyl;

or heterocyl is a 5- or 6-membered saturated heterocyclic ring containing N($R^{20}$) and optionally an O atom as ring atoms, wherein one carbon ring atom is substituted by oxo;

or heterocycyl is a 6-membered heteroaryl ring containing one or two N atoms as ring atoms, wherein the ring is optionally substituted by one to three groups independently selected from halogen, cyano, methyl, halomethyl, methoxy and halomethoxy;

wherein each $R^{13}$ is independently halogen, cyano, $C_1$-$C_4$alkyl, or two $R^{13}$ are together $R^{19}$—O—N=;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen;

wherein $R^{18}$ is hydrogen or methyl;

wherein $R^{19}$ is hydrogen or $C_1$-$C_4$alkyl;

and wherein $R^{20}$ is hydrogen, $C_1$-$C_4$alkyl, $C_2$-$C_4$alkenyl, $C_2$-$C_4$alkynyl, $C_3$-$C_6$cycloalkyl, $C_3$-$C_6$cycloalkyl-$CH_2$—, $C_1$-$C_4$haloalkyl or $C_1$-$C_4$alkoxy.

In another group of compounds $R^2$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by substituted by one to three $R^{13}$, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by substituted by one to three $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)— or heterocyclyl-C($R^{17}$)($R^{18}$)— wherein the heterocyclyl is substituted by one to five $R^{14}$, aryl or aryl substituted by one to five $R^{14}$, heterocyclyl or heterocyclyl substituted by one to five $R^{14}$, $C_1$-$C_4$alkylaminocarbonyl-$CH_2$—, $C_1$-$C_4$haloalkylaminocarbonyl-$CH_2$—, $C_1$-$C_6$alkylaminocarbonyl-, $C_1$-$C_4$alkyl-O—N=CH—, or $C_1$-$C_4$haloalkyl-O—N=CH—;

wherein heterocyclyl is pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, thiolanyl, thiolanyl 1-oxide, thiolanyl 1,1-dioxide, oxetanyl, thietanyl, 1-oxo-thietanyl, 1,1-dioxo-thietanyl, pyrrolidinyl, tetrahydrofuranyl, [1,3]dioxolanyl, piperidinyl, piperazinyl, [1,4]dioxanyl, morpholinyl, 2,3-dihydro-benzofuranyl, benzo[1,3]dioxolanyl, 2,3-dihydro-benzo[1,4]dioxinyl, 3-oxo-isoxazolidinyl, 2,5-dioxo-1-pyrrolidinyl, 2-oxo-1-pyrrolidinyl, 4-oxo-1,3-oxazinanyl, tetrahydropyranyl, or 1-oxa-3,4-diazolyl, and wherein an N atom in heterocycyl is optionally substituted by $R^{20}$;

wherein aryl is phenyl;

wherein each $R^{13}$ is independently halogen, cyano, $C_1$-$C_4$alkyl, or two $R^{13}$ are together $R^{19}$—O—N=;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen;

wherein $R^{18}$ is hydrogen or methyl;

wherein $R^{19}$ is hydrogen or $C_1$-$C_4$alkyl;

and wherein $R^{20}$ is hydrogen, $C_1$-$C_4$alkyl, $C_2$-$C_4$alkenyl, $C_2$-$C_4$alkynyl, $C_3$-$C_6$cycloalkyl, $C_3$-$C_6$cycloalkyl-$CH_2$—, $C_1$-$C_4$haloalkyl or $C_1$-$C_4$alkoxy.

More preferably $R^2$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-$C(R^{17})(R^{18})$— or $C_3$-$C_6$cycloalkyl-$C(R^{17})(R^{18})$— wherein the cycloalkyl is substituted by one to three groups independently selected from halogen and methyl, aryl-$C(R^{17})(R^{18})$— or aryl-$C(R^{17})(R^{18})$— wherein the aryl is substituted by one to five $R^{14}$, heterocyclyl-$C(R^{17})(R^{18})$—, aryl or aryl substituted by one to five $R^{14}$, heterocyclyl, $C_1$-$C_4$alkylaminocarbonyl-$CH_2$—, $C_1$-$C_4$haloalkylaminocarbonyl-$CH_2$—, $C_1$-$C_6$alkylaminocarbonyl-, $C_1$-$C_4$alkyl-O—N=CH—, or $C_1$-$C_4$haloalkyl-O—N=CH—;

wherein heterocyclyl is selected from tetrahydrofuranyl, thiolanyl, thiolanyl 1-oxide, thiolanyl 1,1-dioxide, oxetanyl, thietanyl, 1-oxo-thietanyl, 1,1,-dioxothietanyl each optionally substituted by methyl;

or heterocyclyl is 3-oxo-isoxazolidinyl, 2,5-dioxo-1-pyrrolidinyl, 2-oxo-1-pyrrolidinyl, wherein each is substituted on the nitrogen atom by $C_1$-$C_4$alkyl, $C_3$-$C_6$cycloalkyl, $C_3$-$C_6$cycloalkyl-$CH_2$ or $C_1$-$C_4$haloalkyl;

or heterocyl is 4-oxo-1,3-oxazinanyl, piperidinyl, tetrahydropyranyl, thiazolinyl, pyrimidyl, 1-oxa-3,4-diazolyl, pyridyl, and thiazolyl, each optionally substituted by one to three groups independently selected from halogen, cyano, methyl, halomethyl, methoxy and halomethoxy;

wherein aryl is phenyl;
wherein $R^{17}$ is hydrogen;
and wherein $R^{18}$ is hydrogen or methyl.

More preferably $R^2$ is $C_1$-$C_4$alkyl or $C_1$-$C_4$alkyl wherein a terminal carbon atom is substituted by one to three halogen or substituted by one group selected from methoxy, methylthio, methylsulfinyl and methylsulfonyl, $C_3$-$C_6$cycloalkyl or $C_3$-$C_6$cycloalkyl substituted by one to three groups independently selected from halogen and methyl, $C_3$-$C_6$cycloalkyl-$C(R^{17})(R^{18})$— or $C_3$-$C_6$cycloalkyl-$C(R^{17})(R^{18})$— wherein the cycloalkyl is substituted by one to three groups independently selected from halogen and methyl, aryl-$C(R^{17})(R^{18})$— or aryl-$C(R^{17})(R^{18})$— wherein the aryl is substituted by one to five $R^{14}$, aryl or aryl substituted by one to five $R^{14}$, pyridyl or pyridyl substituted by one to four $R^{14}$, $C_1$-$C_4$alkylaminocarbonyl-$CH_2$—, $C_1$-$C_4$haloalkylaminocarbonyl-$CH_2$—, $C_1$-$C_4$alkylaminocarbonyl, $C_1$-$C_4$alkyl-O—N=CH—, or $C_1$-$C_4$haloalkyl-O—N=CH—, or $R^2$ is selected from groups A1-A12 and B1-B6 (preferably A2, A8 and B1)

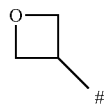

A1

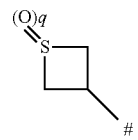

A2

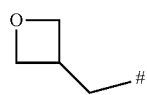

A3

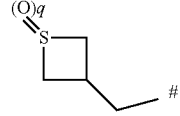

A4

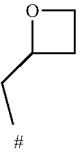

A5

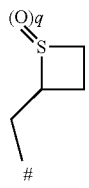

A6

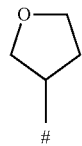

A7

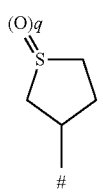 A8

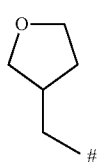 A9

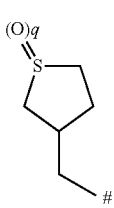 A10

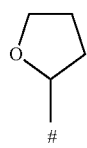 A11

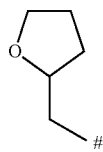 A12

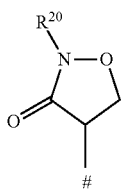 B1

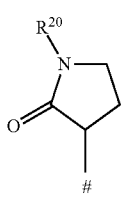 B2

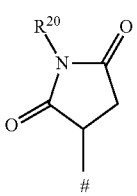 B3

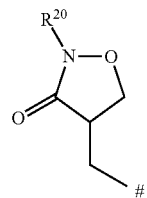 B4

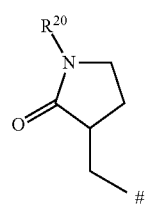 B5

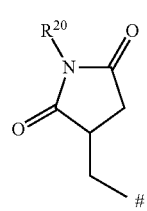 B6 wherein each $R^{14}$ is independently halogen, cyano, methyl, halomethyl, methoxy or halomethoxy;
wherein $R^{17}$ is hydrogen;
wherein $R^{18}$ is hydrogen or methyl;
wherein $R^{20}$ is $C_1$-$C_4$alkyl, $C_3$-$C_6$cycloalkyl, $C_3$-$C_6$cycloalkyl-$CH_2$—, or $C_1$-$C_4$haloalkyl;
wherein q is 0, 1 or 2.

Most preferably $R^2$ is $C_4$-$C_5$cycloalkyl, pyridyl-$CH_2$—, $C_1$-$C_4$alkylaminocarbonyl-$CH_2$—, $C_1$-$C_4$haloalkylaminocarbonyl-$CH_2$—, group A2, A6, A14, A16 or B1 (preferably A2, A8 and B1);
wherein $R^{20}$ is $C_1$-$C_4$alkyl, or $C_1$-$C_4$haloalkyl.

Preferably $R^3$ is trifluoromethyl, difluoromethyl or chlorodifluoromethyl, most preferably trifluoromethyl.

Preferably $R^4$ is aryl or aryl substituted by one to five $R^{15}$, more preferably aryl substituted by one to three $R^{15}$, more preferably phenyl substituted by one to three $R^{15}$.

In one group of compounds $R^4$ is group (C)

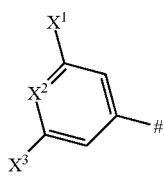 (C)

wherein $X^2$ is C—$X^6$ or nitrogen (preferably C—$X^6$); $X^1$, $X^3$ and $X^6$ are independently hydrogen, halogen or trihalomethyl, e.g. wherein at least two of $X^1$, $X^3$ and $X^6$ are not hydrogen.

Preferably $R^4$ is 3,5-dichlorophenyl, 3-chloro-4-fluorophenyl, 3-fluoro-4-chlorophenyl, 3,4-dichlorophenyl, 3-chloro-4-bromophenyl, 3,5-dichloro-4-fluorophenyl, 3,4,5-trichlorophenyl, 3,5-dichloro-4-iodophenyl, 3,4,5-trifluorophenyl, 3-chloro-5-bromophenyl, 3-chloro-5-fluorophenyl, 3-chloro-5-(trifluoromethyl)phenyl, 3,4-dichloro-5-

(trifluoromethyl)phenyl, 3,5-bis(trifluoromethyl)phenyl, 4-chloro-3,5-bis(trifluoromethyl)phenyl, 3-(trifluoromethyl)phenyl, 2,6-dichloro-4-pyridyl, 2,6-bis(trifluoromethyl)-4-pyridyl, 2-chloro-4-pyridyl-, 2-trifluoromethyl-4-pyridyl, more preferably 3,5-dichloro-phenyl, 3-chloro-5-bromophenyl, 3-chloro-5-(trifluoromethyl)phenyl, 3,5-dichloro-4-fluorophenyl, 3,4,5-trichlorophenyl, 3,5-bis(trifluoromethyl)phenyl, 3-(trifluoromethyl)phenyl, 2,6-dichloro-4-pyridyl, 2,6-bis(trifluoromethyl)-4-pyridyl, 3,5-dichloro-4-bromophenyl, 3-bromo-5-(trifluoromethyl)phenyl, 3,5-dibromophenyl, or 3,4-dichlorophenyl, 2-chloro-4-pyridyl-, 2-trifluoromethyl-4-pyridyl, even more preferably 3,5-dichloro-phenyl, 3,5-dichloro-4-fluorophenyl, 3,4,5-trichlorophenyl, 3-(trifluoromethyl)phenyl, 3,5-bis(trifluoromethyl)phenyl, most preferably 3,5-dichloro-phenyl, 3,5-dichloro-4-fluorophenyl, or 3,4,5-trichlorophenyl-. In one group of compounds $R^4$ is 3,5-dichloro-phenyl. In one group of compounds $R^4$ is 3,5-dichloro-4-fluorophenyl-. In one group of compounds $R^4$ is 3,4,5-trichlorophenyl-. In one group of compounds $R^4$ is 3,5-bis(trifluoromethyl)phenyl.

Preferably each $R^5$ is independently hydrogen, halogen, cyano, nitro, $NH_2$, $C_1$-$C_8$alkyl, $C_1$-$C_8$haloalkyl, $C_3$-$C_5$cycloalkyl, $C_3$-$C_5$halocycloalkyl, $C_1$-$C_8$alkenyl, $C_1$-$C_8$haloalkenyl, $C_1$-$C_8$alkoxy, or $C_1$-$C_8$haloalkoxy, preferably halogen, cyano, nitro, $NH_2$, $C_1$-$C_2$alkyl, $C_1$-$C_2$haloalkyl, $C_3$-$C_5$cycloalkyl, $C_3$-$C_5$halocycloalkyl, $C_1$-$C_2$alkoxy, $C_1$-$C_2$haloalkoxy, more preferably hydrogen, chloro, bromo, fluoro, trifluoromethyl, methyl, ethyl, methoxy, nitro, trifluoromethoxy, cyano, cyclopropyl, even more preferably hydrogen, chloro, bromo, fluoro, methyl, ethyl or trifluoromethyl, even more preferably hydrogen, chloro, bromo, fluoro, methyl or trifluoromethyl, more preferably chloro, bromo or methyl, most preferably methyl. In one group of compounds $R^5$ is chloro. In one group of compounds $R^5$ is bromo. In one group of compounds $R^5$ is methyl. In one group of compounds $R^5$ is halogen.

Preferably at least one of $R^{6a}$ and $R^{6b}$ is hydrogen or $C_1$-$C_8$alkyl, and the other is selected from hydrogen, halogen, cyano, $C_1$-$C_8$alkyl, $C_1$-$C_8$haloalkyl and $C_3$-$C_8$cycloalkyl, or $R^{6a}$ and $R^{6b}$ together from a 3- to 6-membered carbocyclic ring, more preferably at least one of $R^{6a}$ and $R^{6b}$ is hydrogen or methyl and the other is hydrogen, methyl, ethyl or cyclopropyl or $R^{6a}$ and $R^{6b}$ together form a 3- to 4-membered carbocyclic ring, most preferably one of $R^{6a}$ and $R^{6b}$ is hydrogen and the other is hydrogen or methyl.

Preferably $R^7$ is hydrogen, methyl, ethyl, methylcarbonyl, or methoxycarbonyl, more preferably hydrogen, methyl or ethyl, most preferably hydrogen.

Preferably $R^8$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-$C(R^{17})(R^{18})$— or $C_3$-$C_{10}$cycloalkyl-$C(R^{17})(R^{18})$— wherein the cycloalkyl is substituted by one to five $R^{13}$, aryl-$C(R^{17})(R^{18})$— or aryl-$C(R^{17})(R^{18})$— wherein the aryl is substituted by one to five $R^{14}$, heterocyclyl-$C(R^{17})(R^{18})$— or heterocyclyl-$C(R^{17})(R^{18})$— wherein the heterocyclyl is substituted by one to five $R^{14}$, aryl or aryl substituted by one to five $R^{14}$, or heterocyclyl or heterocyclyl substituted by one to five $R^{14}$;
wherein heterocyclyl is a 4- to 7-membered heterocyclic ring containing one to three heteroatoms independently selected from O, S, SO, $SO_2$, N, and $N(R^{14})$ as ring atoms;
wherein aryl is phenyl;
and wherein $R^{17}$ and $R^{18}$ are independently selected from hydrogen, cyano, halogen, $C_1$-$C_4$alkyl, $C_1$-$C_4$haloalkyl, $C_1$-$C_4$alkoxy, $C_1$-$C_4$haloalkoxy and $C_3$-$C_6$cycloalkyl.

More preferably $R^8$ is $C_1$-$C_6$alkyl or $C_1$-$C_6$alkyl substituted by one to five $R^{12}$, $C_3$-$C_6$cycloalkyl or $C_3$-$C_6$cycloalkyl substituted by one to five $R^{13}$, $C_3$-$C_6$cycloalkyl-$C(R^{17})(R^{18})$— or $C_3$-$C_{10}$cycloalkyl-$C(R^{17})(R^{18})$— wherein the cycloalkyl is substituted by one to five $R^{13}$, aryl-$C(R^{17})(R^{18})$— or aryl-$C(R^{17})(R^{18})$— wherein the aryl is substituted by one to five $R^{14}$, heterocyclyl-$C(R^{17})(R^{18})$—, aryl or aryl substituted by one to five $R^{14}$, or heterocyclyl;
wherein heterocyclyl is a 4- to 6-membered saturated heterocyclic ring containing one or two heteroatoms independently selected from O, S, SO, $SO_2$ and $N(R^{20})$ as ring atoms, wherein one or two carbon ring atoms are optionally substituted by oxo, and wherein the ring is optionally substituted by one or two $R^{14}$;
or heterocyclyl is a 5- or 6-membered heteroaryl ring containing one to three heteroatoms selected from O, N and S as ring atoms, wherein the ring is optionally substituted by one to three $R^{14}$;
wherein aryl is phenyl;
wherein $R^{17}$ is hydrogen;
and wherein $R^{18}$ is independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl;
and wherein $R^{20}$ is hydrogen or $R^{14}$.

More preferably $R^8$ is $C_1$-$C_6$alkyl or $C_1$-$C_6$alkyl substituted by one to five $R^{12}$, $C_3$-$C_6$cycloalkyl or $C_3$-$C_6$cycloalkyl substituted by one to five $R^{13}$, $C_3$-$C_6$cycloalkyl-$C(R^{17})(R^{18})$— or $C_3$-$C_6$cycloalkyl-$C(R^{17})(R^{18})$— wherein the cycloalkyl is substituted by one to five $R^{13}$, aryl-$C(R^{17})(R^{18})$— or aryl-$C(R^{17})(R^{18})$— wherein the aryl is substituted by one to five $R^{14}$, heterocyclyl-$C(R^{17})(R^{18})$—, aryl or aryl substituted by one to five $R^{14}$, or heterocyclyl;
wherein heterocyclyl is a 4- to 6-membered saturated heterocyclic ring containing one heteroatom independently selected from O, S, SO, $SO_2$ and $N(R^{20})$ as ring atoms, wherein the ring is optionally substituted by one or two methyl;
or heterocyl is a 6-membered heteroaryl ring containing one or two N atoms as ring atoms, wherein the ring is optionally substituted by one to three groups independently selected from halogen, cyano, $C_1$-$C_4$alkyl, $C_1$-$C_4$haloalkyl, $C_1$-$C_4$alkoxy, $C_1$-$C_4$haloalkoxy;
wherein each $R^{12}$ is independently halogen, $C_1$-$C_8$alkoxy, $C_1$-$C_8$haloalkoxy-mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;
wherein each $R^{13}$ is independently halogen, cyano, or $C_1$-$C_4$alkyl;
wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;
wherein $R^{17}$ is hydrogen;
wherein $R^{18}$ is independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl;
wherein $R^{19}$ is hydrogen or $C_1$-$C_4$alkyl;
and wherein $R^{20}$ is hydrogen or $R^{14}$.

More preferably $R^8$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-$C(R^{17})(R^{18})$— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is a 4- or 5-membered saturated heterocyclic ring containing one heteroatom independently selected from O, S, SO, and $SO_2$ as ring atoms, and wherein the ring is optionally substituted by one or two methyl;

or heterocycyl is a 6-membered heteroaryl ring containing one or two N atoms as ring atoms, wherein the ring is optionally substituted by one to three groups independently selected from halogen, cyano, methyl, halomethyl, methoxy and halomethoxy;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen;

and wherein $R^{18}$ is hydrogen or methyl.

In another group of compounds $R^8$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)— or heterocyclyl-C($R^{17}$)($R^{18}$)— wherein the heterocyclyl is substituted by one to five $R^{14}$, aryl or aryl substituted by one to five $R^{14}$, heterocyclyl or heterocyclyl substituted by one to five $R^{14}$;

wherein heterocyclyl is pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, thiolanyl, thiolanyl 1-oxide, thiolanyl 1,1-dioxide, oxetanyl, thietanyl, 1-oxo-thietanyl, 1,1-dioxo-thietanyl, pyrrolidinyl, tetrahydrofuranyl, [1,3]dioxolanyl, piperidinyl, piperazinyl, [1,4]dioxanyl, morpholinyl, 2,3-dihydro-benzofuranyl, benzo[1,3]dioxolanyl, 2,3-dihydro-benzo[1,4]dioxinyl, 3-oxo-isoxazolidinyl, 2,5-dioxo-1-pyrrolidinyl, 2-oxo-1-pyrrolidinyl, 4-oxo-1,3-oxazinanyl, tetrahydropyranyl, or 1-oxa-3,4-diazolyl;

wherein aryl is phenyl;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen;

and wherein $R^{18}$ is hydrogen or methyl.

More preferably $R^8$ is $C_1$-$C_4$alkyl or $C_1$-$C_4$alkyl wherein a terminal carbon atom is substituted by one to three halogen or substituted by one group selected from methoxy, methylthio, methylsulfinyl and methysulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is tetrahydrofuranyl, thiolanyl, thiolanyl 1-oxide, thiolanyl 1,1-dioxide, oxetanyl, thietanyl, 1-oxo-thietanyl, 1,1,-dioxothietanyl each optionally substituted by methyl;

or heterocycyl is piperidinyl, tetrahydropyranyl, pyridyl, or thiazolyl, each optionally substituted by one to three groups independently selected from halogen, cyano, methyl, halomethyl, methoxy and halomethoxy;

wherein aryl is phenyl;

wherein $R^{17}$ is hydrogen;

and wherein $R^{18}$ is hydrogen or methyl.

Most preferably $R^8$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, aryl or aryl substituted by one to five $R^{14}$, pyridyl or pyridyl substituted by one to four $R^{14}$, or $R^8$ is selected from groups A1-A12 (preferably A2 or A8);

wherein each $R^{14}$ is independently halogen, cyano methyl, halomethyl, methoxy or halomethoxy;

wherein $R^{17}$ is hydrogen;

wherein $R^{18}$ is hydrogen or methyl;

wherein q is 0, 1 or 2.

Preferably $R^9$ is hydrogen, methyl, ethyl, methylcarbonyl, or methoxycarbonyl, more preferably hydrogen, methyl or ethyl, most preferably hydrogen.

Preferably $R^{10}$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-C($R^{17}$)($R^{18}$)— or $C_3$-$C_{10}$cycloalkyl-C($R^{17}$)($R^{18}$)— wherein the cycloalkyl is substituted by one to five $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)— or heterocyclyl-C($R^{17}$)($R^{18}$)— wherein the heterocyclyl is substituted by one to five $R^{14}$, aryl or aryl substituted by one to five $R^{14}$, or heterocyclyl or heterocyclyl substituted by one to five $R^{14}$;

wherein heterocyclyl is a 4- to 7-membered heterocyclic ring containing one to three heteroatoms independently selected from O, S, SO, $SO_2$, N, and N($R^{14}$) as ring atoms;

wherein aryl is phenyl;

and wherein $R^{17}$ and $R^{18}$ are independently selected from hydrogen, cyano, halogen, $C_1$-$C_4$alkyl, $C_1$-$C_4$haloalkyl, $C_1$-$C_4$alkoxy, $C_1$-$C_4$haloalkoxy and $C_3$-$C_6$cycloalkyl.

More preferably $R^{10}$ is $C_1$-$C_6$alkyl or $C_1$-$C_6$alkyl substituted by one to five $R^{12}$, $C_3$-$C_6$cycloalkyl or $C_3$-$C_6$cycloalkyl substituted by one to five $R^{13}$, $C_3$-$C_6$cycloalkyl-C($R^{17}$)($R^{18}$)— or $C_3$-$C_{10}$cycloalkyl-C($R^{17}$)($R^{18}$)— wherein the cycloalkyl is substituted by one to five $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is a 4- to 6-membered saturated heterocyclic ring containing one or two heteroatoms independently selected from O, S, SO, $SO_2$ and N($R^{14}$) as ring atoms, wherein one or two carbon ring atoms are optionally substituted by oxo, and wherein the ring is optionally substituted by one or two $R^{14}$;

or heterocyclyl is a 5- or 6-membered heteroaryl ring containing one to three heteroatoms selected from O, N and S as ring atoms, wherein the ring is optionally substituted by one to three $R^{14}$;

wherein aryl is phenyl;
wherein $R^{17}$ is hydrogen;
and wherein $R^{18}$ is independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl.

More preferably $R^{10}$ is $C_1$-$C_6$alkyl or $C_1$-$C_6$alkyl substituted by one to five $R^{12}$, $C_3$-$C_6$cycloalkyl or $C_3$-$C_6$cycloalkyl substituted by one to five $R^{13}$, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to five $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is a 4 or 5-membered saturated heterocyclic ring containing one heteroatom independently selected from O, S, SO, and $SO_2$ as ring atoms, wherein the ring is optionally substituted by one or two methyl;

or heterocyyl is a 6-membered heteroaryl ring containing one or two N atoms as ring atoms, wherein the ring is optionally substituted by one to three groups independently selected from halogen, cyano, $C_1$-$C_4$alkyl, $C_1$-$C_4$haloalkyl, $C_1$-$C_4$alkoxy, $C_1$-$C_4$haloalkoxy;

wherein each $R^{12}$ is independently halogen, $C_1$-$C_8$alkoxy, $C_1$-$C_8$haloalkoxy-mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;

wherein each $R^{13}$ is independently halogen, cyano, or $C_1$-$C_4$alkyl;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen;
wherein $R^{18}$ is independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl;
and wherein $R^{19}$ is hydrogen or $C_1$-$C_4$alkyl.

More preferably $R^{10}$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is a 4- or 5-membered saturated heterocyclic ring containing one heteroatom independently selected from O, S, SO, and $SO_2$ as ring atoms, and wherein the ring is optionally substituted by one or two methyl;

or heterocyyl is a 6-membered heteroaryl ring containing one or two N atoms as ring atoms, wherein the ring is optionally substituted by one to three groups independently selected from halogen, cyano, methyl, halomethyl, methoxy and halomethoxy;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen;
and wherein $R^{18}$ is hydrogen or methyl.

In another group of compounds $R^{10}$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)— or heterocyclyl-C($R^{17}$)($R^{18}$)— wherein the heterocyclyl is substituted by one to five $R^{14}$, aryl or aryl substituted by one to five $R^{14}$, heterocyclyl or heterocyclyl substituted by one to five $R^{14}$;

wherein heterocyclyl is pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, thiolanyl, thiolanyl 1-oxide, thiolanyl 1,1-dioxide, oxetanyl, thietanyl, 1-oxo-thietanyl, 1,1-dioxo-thietanyl, pyrrolidinyl, tetrahydrofuranyl, [1,3]dioxolanyl, piperidinyl, piperazinyl, [1,4]dioxanyl, morpholinyl, 2,3-dihydro-benzofuranyl, benzo[1,3]dioxolanyl, 2,3-dihydro-benzo[1,4]dioxinyl, 3-oxo-isoxazolidinyl, 2,5-dioxo-1-pyrrolidinyl, 2-oxo-1-pyrrolidinyl, 4-oxo-1,3-oxazinanyl, tetrahydropyranyl, or 1-oxa-3,4-diazolyl;

wherein aryl is phenyl;
wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;
wherein $R^{17}$ is hydrogen;
and wherein $R^{18}$ is hydrogen or methyl.

More preferably $R^{10}$ is $C_1$-$C_4$alkyl or $C_1$-$C_4$alkyl wherein a terminal carbon atom is substituted by one to three halogen or substituted by one group selected from methoxy, methylthio, methylsulfinyl and methysulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is tetrahydrofuranyl, thiolanyl, thiolanyl 1-oxide, thiolanyl 1,1-dioxide, oxetanyl, thietanyl, 1-oxo-thietanyl, 1,1,-dioxothietanyl each optionally substituted by methyl;

or heterocyyl is piperidinyl, tetrahydropyranyl, pyridyl, or thiazolyl, each optionally substituted by one to three groups independently selected from halogen, cyano, methyl, halomethyl, methoxy and halomethoxy;

wherein aryl is phenyl;
wherein $R^{17}$ is hydrogen;
and wherein $R^{18}$ is hydrogen or methyl.

Most preferably $R^{10}$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-$C(R^{17})(R^{18})$— wherein the cycloalkyl is substituted by one to three groups independently selected from halogen and methyl, aryl-$C(R^{17})(R^{18})$— or aryl-$C(R^{17})(R^{18})$— wherein the aryl is substituted by one to five $R^{14}$, aryl or aryl substituted by one to five $R^{14}$, pyridyl or pyridyl substituted by one to four $R^{14}$, or $R^{16}$ is selected from groups A1-A12 (preferably A2 or A8);

wherein each $R^{14}$ is independently halogen, cyano methyl, halomethyl, methoxy or halomethoxy;

wherein $R^{17}$ is hydrogen;

wherein $R^{18}$ is hydrogen or methyl;

wherein q is 0, 1 or 2.

Preferably each $R^{11}$ is independently hydrogen, halogen, cyano, $C_1$-$C_4$alkyl, $C_1$-$C_4$haloalkyl, $C_1$-$C_4$alkoxy, or $C_1$-$C_4$haloalkoxy, more preferably hydrogen, bromo, chloro, fluoro, cyano, nitro, methyl, ethyl, trifluoromethyl, methoxy, difluoromethoxy, or trifluoromethoxy, more preferably hydrogen, bromo, chloro, fluoro, cyano or methyl, most preferably hydrogen.

Preferably each $R^{12}$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl, more preferably halogen, cyano, nitro, hydroxy, $C_1$-$C_8$alkoxy, $C_1$-$C_8$haloalkoxy, mercapto, $C_1$-$C_8$alkylthio, or $C_1$-$C_8$haloalkylthio, more preferably halogen, cyano, $C_1$-$C_8$alkoxy, $C_1$-$C_8$haloalkoxy, mercapto, $C_1$-$C_8$alkylthio, or $C_1$-$C_8$haloalkylthio, even more preferably halogen, $C_1$-$C_4$alkoxy, $C_1$-$C_4$alkylthio, $C_1$-$C_4$ alkylsulfinyl or $C_1$-$C_4$alkylsulfonyl, most preferably halogen, methoxy, methylthio, methylsulfinyl or methysulfonyl.

Preferably each $R^{13}$ is independently halogen, cyano, or $C_1$-$C_4$alkyl, or two $R^{13}$ are together $R^{19}$—O—N=, more preferably halogen or methyl, even more preferably chloro, fluoro or methyl, most preferably fluoro or methyl.

Preferably each $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{16}$, or heterocyclyl or heterocyclyl substituted by one to five $R^{16}$, more preferably halogen, cyano, nitro, $C_1$-$C_4$alkyl, $C_1$-$C_4$haloalkyl, $C_1$-$C_4$alkoxy, or $C_1$-$C_4$haloalkoxy, even more preferably halogen, cyano, methyl, halomethyl, methoxy, or halomethoxy; most preferably bromo, chloro, fluoro, methyl, halomethyl, methoxy or halomethoxy.

Preferably each $R^{15}$ is independently halogen, $C_1$-$C_8$alkyl, $C_1$-$C_8$haloalkyl, $C_1$-$C_8$alkoxy, $C_1$-$C_8$haloalkoxy, $C_1$-$C_8$alkylthio, or $C_1$-$C_8$haloalkylthio, more preferably bromo, chloro, fluoro, trifluoromethyl, methoxy, or methylthio, most preferably trifluoromethyl, fluoro or chloro.

Preferably each $R^{16}$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, most preferably hydrogen, halogen, cyano, methyl, halomethyl, methoxy or halomethoxy.

Preferably k is 0 or 1, preferably 0 when H is H6.

Preferably n is 1;

Preferably p is 0, 1, or 2, preferably 0 or 1, most preferably 0;

In one embodiment (E1) n is 1 and p is 0.

In one embodiment (E2) P is P1.

In another Embodiment (E3) P is P2.

In another embodiment (E4) P and $R^5$ together are P3.

In another embodiment (E5) P is a heterocycle H.

In another embodiment (E6) $Y^1$ is CH, $Y^2$ is CH, and $Y^3$ is CH.

In another embodiment (E7) $Y^1$ is CH, $Y^2$ is CH, and $Y^3$ is CH and P is P1.

In another embodiment (E8) $Y^1$ is CH, $Y^2$ is CH, and $Y^3$ is CH and P is P2.

In another embodiment (E9) $Y^1$ is CH, $Y^2$ is CH, and $Y^3$ is CH and P and $R^5$ together are P3.

In another embodiment (E10) $Y^1$ is CH, $Y^2$ is CH, and $Y^3$ is CH and P is heterocycle H.

In another embodiment (E11) $Y^1$ is C—$R^5$, $Y^2$ is CH, $Y^3$ is CH and both $R^5$ together form a —CH=CH—CH=CH— bridge.

In another embodiment (E12) $Y^1$ is C—$R^5$, $Y^2$ is CH, $Y^3$ is CH and both $R^5$ together form a —CH=CH—CH=CH— bridge and P is P1.

In another embodiment (E13) $Y^1$ is C—$R^5$, $Y^2$ is CH, $Y^3$ is CH and both $R^5$ together form a —CH=CH—CH=CH— bridge and P is P2.

In another embodiment (E14) $Y^1$ is C—$R^5$, $Y^2$ is CH, $Y^3$ is CH and both $R^5$ together form a —CH=CH—CH=CH— bridge and P and $R^5$ together are P3.

In another embodiment (E15) $Y^1$ is C—$R^5$, $Y^2$ is CH, $Y^3$ is CH and both $R^5$ together form a —CH=CH—CH=CH— bridge and P is heterocycle H.

In another embodiment (E16) P is selected from P1 and P2, or P and $R^5$ together are P3, or H2 or H6;

$G^1$, $G^2$ and $G^3$ are oxygen;

$Y^1$, $Y^2$, and $Y^3$ are C—H;

$R^1$, $R^7$ and $R^9$ are hydrogen;

$R^2$ is $C_1$-$C_6$alkyl or $C_1$-$C_6$alkyl substituted by one to five $R^{12}$, $C_3$-$C_8$cycloalkyl or $C_3$-$C_8$cycloalkyl substituted by one to five $R^{13}$, $C_3$-$C_8$cycloalkyl-$C(R^{17})(R^{18})$— or $C_3$-$C_8$cycloalkyl-$C(R^{17})(R^{18})$— wherein the cycloalkyl is substituted by one to five $R^{13}$, aryl-$C(R^{17})(R^{18})$— or aryl-$C(R^{17})(R^{18})$— wherein the aryl is substituted by one to five $R^{14}$, heterocyclyl-$C(R^{17})(R^{18})$—, aryl or aryl substituted by one to five $R^{14}$, heterocyclyl, $C_1$-$C_6$alkylaminocarbonyl-$CH_2$—, $C_1$-$C_6$haloalkylaminocarbonyl-$CH_2$—, $C_3$-$C_8$cycloalkyl-aminocarbonyl-$CH_2$—, aryl-$CH_2$-aminocarbonyl-$CH_2$— or aryl-$CH_2$-aminocarbonyl-$CH_2$— wherein the aryl is substituted by one to five $R^{14}$, $C_1$-$C_6$alkylaminocarbonyl-, $C_3$-$C_6$cycloalkylaminocarbonyl-, $C_1$-$C_4$alkyl-O—N=CH—, or $C_1$-$C_4$haloalkyl-O—N=CH—;

wherein heterocyclyl is a 4 or 5-membered saturated heterocyclic ring containing one heteroatom independently selected from O, S, SO, and $SO_2$ as ring atoms, wherein the ring is optionally substituted by one or two methyl;

or heterocyclyl is a 5 or 6-membered saturated or partially saturated heterocyclic ring containing one or two heteroatoms selected from, $N(R^{20})$, N, S and O as ring atoms, wherein one or two carbon ring atoms are optionally substituted by oxo;

or heterocycyl is a 6-membered heteroaryl ring containing one to three heteroatoms selected from O, N and S as ring atoms, wherein the ring is optionally substituted by one to three groups independently selected from halogen, cyano, $C_1$-$C_4$alkyl, $C_1$-$C_4$haloalkyl, $C_1$-$C_4$alkoxy, $C_1$-$C_4$haloalkoxy and $C_3$-$C_6$cycloalkyl;

$R^3$ is trifluoromethyl or chlorodifluoromethyl;
$R^4$ is group (C)

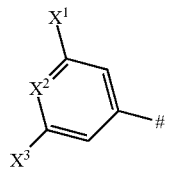

(C)

wherein $X^2$ is C—$X^6$ or nitrogen (preferably C—$X^6$); $X^1$, $X^3$ and $X^6$ are independently hydrogen, halogen or trihalomethyl, wherein at least one of $X^1$, $X^3$ and $X^6$ is not hydrogen;

$R^5$ is hydrogen, chloro, bromo, fluoro, methyl, ethyl or trifluoromethyl;

at least one of $R^{6a}$ and $R^{6b}$ is hydrogen or methyl and the other is hydrogen, methyl, ethyl or cyclopropyl or $R^{6a}$ and $R^{6b}$ together form a 3- to 4-membered carbocyclic ring, $R^8$ is $C_1$-$C_6$alkyl or $C_1$-$C_6$alkyl substituted by one to five $R^{12}$, $C_3$-$C_6$cycloalkyl or $C_3$-$C_6$cycloalkyl substituted by one to five $R^{13}$, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to five $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is a 4- to 6-membered saturated heterocyclic ring containing one heteroatom independently selected from O, S, SO, $SO_2$ and N($R^{20}$) as ring atoms, wherein the ring is optionally substituted by one or two methyl;

or heterocycyl is a 6-membered heteroaryl ring containing one or two N atoms as ring atoms, wherein the ring is optionally substituted by one to three groups independently selected from halogen, cyano, $C_1$-$C_4$alkyl, $C_1$-$C_4$haloalkyl, $C_1$-$C_4$alkoxy, $C_1$-$C_4$haloalkoxy;

$R^{10}$ is $C_1$-$C_6$alkyl or $C_1$-$C_6$alkyl substituted by one to five $R^{12}$, $C_3$-$C_6$cycloalkyl or $C_3$-$C_6$cycloalkyl substituted by one to five $R^{13}$, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to five $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is a 4- to 6-membered saturated heterocyclic ring containing one heteroatom independently selected from O, S, SO, $SO_2$ and N($R^{20}$) as ring atoms, wherein the ring is optionally substituted by one or two methyl;

or heterocycyl is a 6-membered heteroaryl ring containing one or two N atoms as ring atoms, wherein the ring is optionally substituted by one to three groups independently selected from halogen, cyano, $C_1$-$C_4$alkyl, $C_1$-$C_4$haloalkyl, $C_1$-$C_4$alkoxy, $C_1$-$C_4$haloalkoxy;

herein each $R^{12}$ is independently halogen, $C_1$-$C_8$alkoxy, $C_1$-$C_8$haloalkoxy-mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;

wherein each $R^{13}$ is independently halogen, cyano, $C_1$-$C_4$alkyl, or two $R^{13}$ are together $R^{19}$—O—N=;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen or $C_1$-$C_4$alkyl;

wherein $R^{18}$ is independently hydrogen, cyano, halogen, $C_1$-$C_4$alkyl, $C_1$-$C_4$haloalkyl, $C_1$-$C_4$alkoxy, $C_1$-$C_4$haloalkoxy or $C_3$-$C_6$cycloalkyl;

or $R^{17}$ and $R^{18}$ together form a three to six membered carbocycle;

wherein $R^{19}$ is H or $C_1$-$C_4$alkyl;

and wherein $R^{20}$ is hydrogen, $C_1$-$C_4$alkyl, $C_2$-$C_4$alkenyl, $C_2$-$C_4$alkynyl, $C_3$-$C_6$cycloalkyl, $C_3$-$C_6$cycloalkyl-$CH_2$, $C_1$-$C_4$haloalkyl, $C_1$-$C_4$alkoxyalkyl, $C_1$-$C_4$haloalkoxyalkyl, $C_1$-$C_4$alkoxy-$C_1$-$C_4$alkyl, $C_1$-$C_4$alkoxy, $C_1$-$C_4$alkylcarbonyl, $C_1$-$C_4$haloalkylcarbonyl, phenyl-$CH_2$-alkyl- or phenyl-$CH_2$— wherein the phenyl moiety is substituted by one to three groups independently selected from halogen, cyano, methyl, halomethyl, methoxy and halomethoxy, furanyl or furanyl substituted by one to three groups independently selected from halogen, cyano, methyl, halomethyl, methoxy and halomethoxy, thietanyl, oxetanyl, 1-oxo-thietanyl, or 1,1-dioxo-thietanyl.

each Z is independently hydrogen, halogen, cyano, methyl, halomethyl, methoxy or halomethoxy;

and n is 1 or 2, p is 0; k is 0 or 1.

In another embodiment (E17):

P is selected from P1 and P2, or P and $R^5$ together are P3, or H2 or H6;

$G^1$, $G^2$ and $G^3$ are oxygen;

$Y^1$, $Y^2$, and $Y^3$ are C—H;

$R^1$, $R^7$ and $R^9$ are hydrogen;

$R^2$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_8$cycloalkyl or $C_3$-$C_8$cycloalkyl substituted by one to three $R^{13}$, $C_3$-$C_8$cycloalkyl-C($R^{17}$)($R^{18}$)— or $C_3$-$C_8$cycloalkyl-C($R^{17}$)($R^{18}$)— wherein the cycloalkyl is substituted by one to three groups $R^{13}$, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, heterocyclyl, $C_1$-$C_4$alkylaminocarbonyl-$CH_2$—, $C_1$-$C_4$haloalkylaminocarbonyl-$CH_2$—, $C_1$-$C_6$alkylaminocarbonyl-, $C_1$-$C_4$alkyl-O—N=CH—, or $C_1$-$C_4$haloalkyl-O—N=CH—;

wherein heterocyclyl is a 4- or 5-membered saturated heterocyclic ring containing one heteroatom independently selected from O, S, SO, and $SO_2$ as ring atoms, wherein the ring is optionally substituted by one or two methyl;

or heterocycyl is a 5- or 6-membered saturated heterocyclic ring containing N($R^{20}$) and optionally an O atom as ring atoms, wherein one carbon ring atom is substituted by oxo;

or heterocycyl is a 6-membered heteroaryl ring containing one or two N atoms as ring atoms, wherein the ring is optionally substituted by one to three groups independently selected from halogen, cyano, methyl, halomethyl, methoxy and halomethoxy;

$R^3$ is trifluoromethyl or chlorodifluoromethyl;
$R^4$ is group (C)

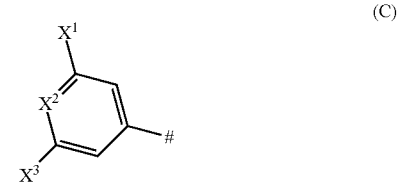

(C)

wherein $X^2$ is C—$X^6$ or nitrogen (preferably C—$X^6$); $X^1$, $X^3$ and $X^6$ are independently hydrogen, halogen or trihalomethyl, wherein at least one of $X^1$, $X^3$ and $X^6$ is not hydrogen;

$R^5$ is hydrogen, chloro, bromo, fluoro, or methyl;

$R^{6a}$ and $R^{6b}$ are independently hydrogen or methyl;

$R^8$ is $R^8$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is a 4- or 5-membered saturated heterocyclic ring containing one heteroatom independently selected from O, S, SO, and $SO_2$ as ring atoms, and wherein the ring is optionally substituted by one or two methyl;

or heterocycyl is a 6-membered heteroaryl ring containing one or two N atoms as ring atoms, wherein the ring is optionally substituted by one to three groups independently selected from halogen, cyano, methyl, halomethyl, methoxy and halomethoxy.

$R^{10}$ is $R^8$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, heterocyclyl-C($R^{17}$)($R^{18}$)—, aryl or aryl substituted by one to five $R^{14}$, or heterocyclyl;

wherein heterocyclyl is a 4- or 5-membered saturated heterocyclic ring containing one heteroatom independently selected from O, S, SO, and $SO_2$ as ring atoms, and wherein the ring is optionally substituted by one or two methyl;

or heterocycyl is a 6-membered heteroaryl ring containing one or two N atoms as ring atoms, wherein the ring is optionally substituted by one to three groups independently selected from halogen, cyano, methyl, halomethyl, methoxy and halomethoxy.

wherein each $R^{13}$ is independently halogen, cyano, $C_1$-$C_4$alkyl, or two $R^{13}$ are together $R^{19}$—O—N=;

wherein each $R^{14}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

wherein $R^{17}$ is hydrogen;

wherein $R^{18}$ is hydrogen or methyl;

wherein $R^{19}$ is hydrogen or $C_1$-$C_4$alkyl;

and wherein $R^{20}$ is hydrogen, $C_1$-$C_4$alkyl, $C_2$-$C_4$alkenyl, $C_2$-$C_4$alkynyl, $C_3$-$C_6$cycloalkyl, $C_3$-$C_6$cycloalkyl-$CH_2$—, $C_1$-$C_4$haloalkyl or $C_1$-$C_4$alkoxy.

each Z is independently hydrogen, halogen, cyano, methyl, halomethyl, methoxy or halomethoxy;

and n is 1, p is 0; k is 0 or 1.

In another embodiment (E18):

P is selected from P1 and P2, or P and $R^5$ together are P3, or H2 or H6;

$G^1$, $G^2$ and $G^3$ are oxygen;

$Y^1$, $Y^2$, and $Y^3$ are C—H;

$R^1$, $R^7$ and $R^9$ are hydrogen;

$R^2$ is $C_1$-$C_4$alkyl or $C_1$-$C_4$alkyl wherein a terminal carbon atom is substituted by one to three halogen or substituted by one group selected from methoxy, methylthio, methylsulfinyl and methysulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, aryl or aryl substituted by one to five $R^{14}$, pyridyl or pyridyl substituted by one to four $R^{14}$, $C_1$-$C_4$alkylaminocarbonyl-$CH_2$—, $C_1$-$C_4$haloalkylaminocarbonyl-$CH_2$—, $C_1$-$C_4$alkylaminocarbonyl, $C_1$-$C_4$alkyl-O—N=CH—, or $C_1$-$C_4$haloalkyl-O—N=CH—, or $R^2$ is selected from groups A1-A12 and B1-B6 (preferably A2, A8 and B1)

$R^3$ is trifluoromethyl or chlorodifluoromethyl;

$R^4$ is group (C)

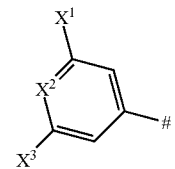

(C)

wherein $X^2$ is C—$X^6$ or nitrogen (preferably C—$X^6$); $X^1$, $X^3$ and $X^6$ are independently hydrogen, halogen or trihalomethyl, wherein at least one of $X^1$, $X^3$ and $X^6$ is not hydrogen;

$R^5$ is hydrogen, chloro, bromo, fluoro, or methyl;

$R^{6a}$ and $R^{6b}$ are independently hydrogen or methyl;

$R^8$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, aryl or aryl substituted by one to five $R^{14}$, pyridyl or pyridyl substituted by one to four $R^{14}$, or $R^8$ is selected from groups A1-A12 (preferably A2 or A8);

$R^{10}$ is $C_1$-$C_4$alkyl or $C_1$-$C_4$alkyl wherein a terminal carbon atom is substituted by one to three halogen or substituted by one group selected from $C_1$-$C_4$alkoxy, $C_1$-$C_4$alkylthio, $C_1$-$C_4$ alkylsulfinyl and $C_1$-$C_4$alkylsulfonyl, $C_3$-$C_6$cycloalkyl or $C_3$-$C_6$cycloalkyl substituted by one to three groups independently selected from halogen and methyl, $C_3$-$C_6$cycloalkyl-C($R^{17}$)($R^{18}$)— or $C_3$-$C_6$cycloalkyl-C($R^{17}$)($R^{18}$)— wherein the cycloalkyl is substituted by one to three groups independently selected from halogen and methyl, aryl-C($R^{17}$)($R^{18}$)— or aryl-C($R^{17}$)($R^{18}$)— wherein the aryl is substituted by one to five $R^{14}$, aryl or aryl substituted by one to five $R^{14}$, pyridyl or pyridyl substituted by one to four $R^{14}$, or $R^{10}$ is selected from groups A1-A12 (preferably A2 or A8);

each $R^{14}$ is independently halogen, cyano, methyl, halomethyl, methoxy or halomethoxy;

$R^{17}$ is hydrogen;

$R^{18}$ is hydrogen or methyl;

$R^{20}$ is $C_1$-$C_4$alkyl, $C_3$-$C_6$cycloalkyl, $C_3$-$C_6$cycloalkyl-$CH_2$—, or $C_1$-$C_4$haloalkyl;

each Z is independently hydrogen, halogen, cyano, methyl, halomethyl, methoxy or halomethoxy;

and n is 1, p is 0; q is 0, 1 or 2; k is 0 or 1.

In one embodiment (E19) P is $P^1$ and $R^1$, $R^2$, $G^1$, $R^3$, $R^4$, $R^5$, $Y^1$, $Y^2$, $Y^3$, are as defined in embodiment E16.

In another Embodiment (E20) P is P2 and $R^5$, $R^{6a}$, $R^{6b}$, $R^7$, $R^8$, $R^3$, $R^4$, $R^5$, $Y^1$, $Y^2$, $Y^3$ are as defined in embodiment E16.

In another embodiment (E21) P and $R^5$ together are P3 and $R^9$, $R^{10}$, $R^{11}$, p, n, $R^3$, $R^4$, $R^5$, $Y^1$, $Y^2$, $Y^3$ are as defined in embodiment E16.

In another Embodiment (E22) P is a heterocycle H, selected from H2 and H6 and Z, k, $R^3$, $R^4$, $R^5$, $Y^1$, $Y^2$, $Y^3$ are as defined in embodiment E16.

In one embodiment (E23) P is $P^1$ and $R^1$, $R^2$, $G^1$, $R^3$, $R^4$, $R^5$, $Y^1$, $Y^2$, $Y^3$ are as defined in embodiment E17.

In another Embodiment (E24) P is P2 and $R^5$, $R^{6a}$, $R^{6b}$, $R^7$, $R^8$, $R^3$, $R^4$, $R^5$, $Y^1$, $Y^2$, $Y^3$ are as defined in embodiment E17.

In another embodiment (E25) P and $R^5$ together are P3 and $R^9$, $R^{10}$, $R^{11}$, p, n, $R^3$, $R^4$, $R^5$, $Y^1$, $Y^2$, $Y^3$ are as defined in embodiment E17.

In another Embodiment (E26) P is a heterocycle H, selected from H2 and H6 and Z, k, $R^3$, $R^4$, $R^5$, $Y^1$, $Y^2$, $Y^3$ are as defined in embodiment E17.

In one embodiment (E27) P is $P^1$ and $R^1$, $R^2$, $G^1$, $R^3$, $R^4$, $R^5$, $Y^1$, $Y^2$, $Y^3$ are as defined in embodiment E18.

In another embodiment (E28) P is P2 and $R^5$, $R^{6a}$, $R^{6b}$, $R^7$, $R^8$, $R^3$, $R^4$, $R^5$, $Y^1$, $Y^2$, $Y^3$ are as defined in embodiment E18.

In another embodiment (E29) P and $R^5$ together are P3 and $R^9$, $R^{10}$, $R^{11}$, p, n, $R^3$, $R^4$, $R^5$, $Y^1$, $Y^2$, $Y^3$ are as defined in embodiment E18.

In another Embodiment (E30) P is a heterocycle H, selected from H2 and H6 and Z, k, $R^3$, $R^4$, $R^5$, $Y^1$, $Y^2$, $Y^3$ are as defined in embodiment E18.

The present invention also provides intermediates useful for the preparation of compounds of formula I. One group of novel intermediates are compounds of formula (Int-I)

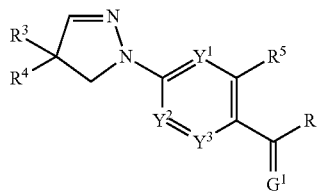

(Int-I)

wherein $Y^1$, $Y^2$, $Y^3$, $G^1$, $R^3$, $R^4$, $R^5$ are as defined for compounds of formula I and R is hydroxy, $C_1$-$C_{15}$alkoxy or halogen, such as bromo, chloro or fluoro; or a salt or N-oxide thereof. The preferred definitions of $Y^1$, $Y^2$, $Y^3$, $G^1$, $R^3$, $R^4$ and $R^5$ are as defined for compounds of formula I. Preferably R is hydroxy, $C_1$-$C_6$alkoxy or chloro.

A further group of novel intermediates are compounds of formula Int-II

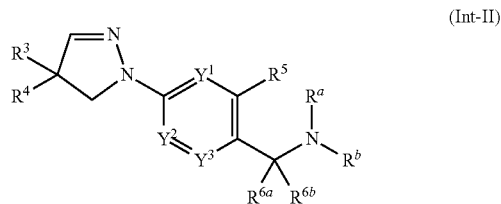

(Int-II)

wherein $Y^1$, $Y^2$, $Y^3$, $R^3$, $R^4$, $R^5$, $R^{6a}$ and $R^{6b}$ are as defined for compounds of formula I and $R^a$ and $R^b$ are independently selected from hydrogen, $C_1$-$C_8$carbonyl, $C_1$-$C_8$alkoxycarbonyl, or $R^a$ and $R^b$ together are —C(=O)—(CH$_2$)$_r$—C(=O)— wherein r is 1 to 4, —C(C$_1$-C$_3$alkyl)=C—C=(C$_1$-C$_3$alkyl)C—, or group D

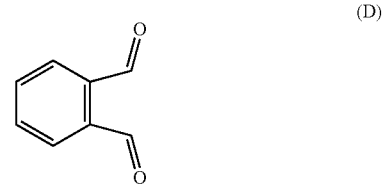

(D)

or a salt or N-oxide thereof. The preferred definitions of $Y^1$, $Y^2$, $Y^3$, $R^3$, $R^4$, $R^5$, $R^{6a}$ and $R^{6b}$ are as defined for compounds of formula I. Preferably $R^a$ and $R^b$ are independently hydrogen, $C_1$-$C_4$carbonyl, $C_1$-$C_4$alkoxycarbonyl, or $R^a$ together are —C(=O)—(CH$_2$)$_2$—C(=O)—, —C(CH$_3$)=C—C=(CH$_3$)C—, or group D. Most preferably $R^a$ and $R^b$ are independently hydrogen, tert-butoxycarbonyl or $R^a$ and $R^b$ together form group D. Preferably at least one of $R^a$ and $R^b$ is not hydrogen.

A further group of novel intermediates are compounds of formula Int-III

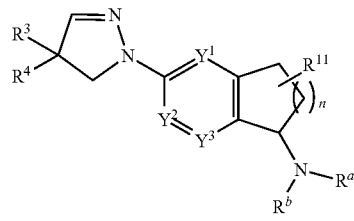

(Int-III)

wherein $Y^1$, $Y^2$, $Y^3$, $R^3$, $R^4$, $R^{11}$ and n are as defined for compounds of formula I and $R^a$ and $R^b$, are as defined for the compounds of formula Int-II. or a salt or N-oxide thereof. The preferred definitions of $Y^1$, $Y^2$, $Y^3$, $R^3$, $R^4$ and $R^{11}$ are as defined for compounds of formula I. The preferred definitions of $R^a$ and $R^b$ are as defined for the compounds of formula Int-H.

A further group of novel intermediates are compounds of formula Int-IV

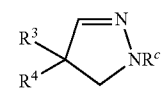

(Int-IV)

wherein $R^3$ and $R^4$ are as defined for compounds of formula I and $R^e$ is hydrogen or a salt or N-oxide thereof. The preferred definitions of $R^3$ and $R^4$ are as defined for compounds of formula I.

A further group of novel intermediates are compounds of formula Int-IV

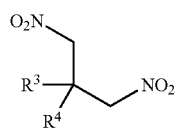
(Int-V)

wherein $R^3$ and $R^4$ are as defined for compounds of formula I or a salt or N-oxide thereof. The preferred definitions of $R^3$ and $R^4$ are as defined for compounds of formula I.

Compounds of formula I include at least one chiral centre and may exist as compounds of formula I* or compounds of formula I**:

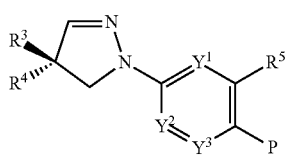
I*

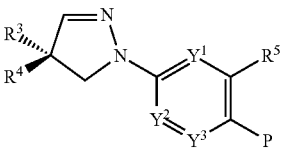
I**

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula I*, the molar proportion of the compound of formula I* compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred. Each compound disclosed in Tables 1 to 176 represents a disclosure of a compound according to the compound of formula I*, and a disclosure according to the compound of formula I**.

Likewise compounds of formula I include compounds of formula Ia and Ib

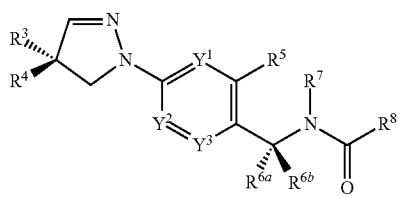
I**a

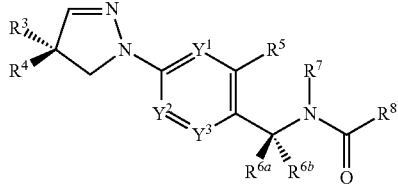
I**b

Each compound disclosed in Tables 138 to 176 includes a disclosure of a compound according to the compound of formula Ia, and a disclosure according to the compound of formula Ib.

Likewise compounds of formula I include compounds of formula Ic and Id

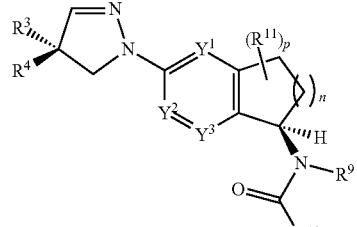
I**c

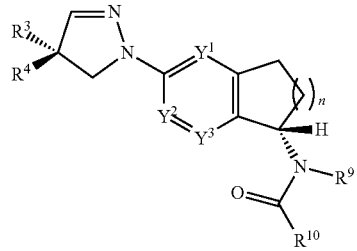
I**d

Each compound disclosed in Tables 96 to 134 includes a disclosure of a compound according to the compound of formula Ic, and a disclosure according to the compound of formula Id.

The tables below illustrate compounds of the invention.

TABLE P

| | R3 | R4 | R5 |
|---|---|---|---|
| 1 | CF3 | 3,5-dichlorophenyl- | Br |
| 2 | CClCF2 | 3,5-dichlorophenyl- | Br |
| 3 | CF3 | 3,4,5-trichlorophenyl- | Br |
| 4 | CClCF2 | 3,4,5-trichlorophenyl- | Br |
| 5 | CF3 | 3,5-dichloro-4-fluorophenyl- | Br |
| 6 | CClCF2 | 3,5-dichloro-4-fluorophenyl- | Br |
| 7 | CF3 | 3-trifluoromethylphenyl- | Br |
| 8 | CClCF2 | 3-trifluoromethylphenyl- | Br |
| 9 | CF3 | 3,5-bis(trifluoromethyl)phenyl- | Br |
| 10 | CClCF2 | 3,5-bis(trifluoromethyl)phenyl- | Br |

TABLE P-continued

|  | R3 | R4 | R5 |
|---|---|---|---|
| 11 | CF3 | 3-chloro-5-trifluoromethylphenyl- | Br |
| 12 | CClCF2 | 3-chloro-5-trifluoromethylphenyl- | Br |
| 13 | CF3 | 3,4-dichlorophenyl- | Br |
| 14 | CClCF2 | 3,4-dichlorophenyl- | Br |
| 15 | CF3 | 2-chloropyrid-4-yl- | Br |
| 16 | CClCF2 | 2-chloropyrid-4-yl- | Br |
| 17 | CF3 | 2,6-dichloropyrid-4-yl- | Br |
| 18 | CClCF2 | 2,6-dichloropyrid-4-yl- | Br |
| 19 | CF3 | 3,5-dichlorophenyl- | Cl |
| 20 | CClCF2 | 3,5-dichlorophenyl- | Cl |
| 21 | CF3 | 3,4,5-trichlorophenyl- | Cl |
| 22 | CClCF2 | 3,4,5-trichlorophenyl- | Cl |
| 23 | CF3 | 3,5-dichloro-4-fluorophenyl- | Cl |
| 24 | CClCF2 | 3,5-dichloro-4-fluorophenyl- | Cl |
| 25 | CF3 | 3-trifluoromethylphenyl- | Cl |
| 26 | CClCF2 | 3-trifluoromethylphenyl- | Cl |
| 27 | CF3 | 3,5-bis(trifluoromethyl)phenyl- | Cl |
| 28 | CClCF2 | 3,5-bis(trifluoromethyl)phenyl- | Cl |
| 29 | CF3 | 3-chloro-5-trifluoromethylphenyl- | Cl |
| 30 | CClCF2 | 3-chloro-5-trifluoromethylphenyl- | Cl |
| 31 | CF3 | 3,4-dichlorophenyl- | Cl |
| 32 | CClCF2 | 3,4-dichlorophenyl- | Cl |
| 33 | CF3 | 2-chloropyrid-4-yl- | Cl |
| 34 | CClCF2 | 2-chloropyrid-4-yl- | Cl |
| 35 | CF3 | 2,6-dichloropyrid-4-yl- | Cl |
| 36 | CClCF2 | 2,6-dichloropyrid-4-yl- | Cl |
| 37 | CF3 | 3,5-dichlorophenyl- | CH3 |
| 38 | CClCF2 | 3,5-dichlorophenyl- | CH3 |
| 39 | CF3 | 3,4,5-trichlorophenyl- | CH3 |
| 40 | CClCF2 | 3,4,5-trichlorophenyl- | CH3 |
| 41 | CF3 | 3,5-dichloro-4-fluorophenyl- | CH3 |
| 42 | CClCF2 | 3,5-dichloro-4-fluorophenyl- | CH3 |
| 43 | CF3 | 3-trifluoromethylphenyl- | CH3 |
| 44 | CClCF2 | 3-trifluoromethylphenyl- | CH3 |
| 45 | CF3 | 3,5-bis(trifluoromethyl)phenyl- | CH3 |
| 46 | CClCF2 | 3,5-bis(trifluoromethyl)phenyl- | CH3 |
| 47 | CF3 | 3-chloro-5-trifluoromethylphenyl- | CH3 |
| 48 | CClCF2 | 3-chloro-5-trifluoromethylphenyl- | CH3 |
| 49 | CF3 | 3,4-dichlorophenyl- | CH3 |
| 50 | CClCF2 | 3,4-dichlorophenyl- | CH3 |
| 51 | CF3 | 2-chloropyrid-4-yl- | CH3 |
| 52 | CClCF2 | 2-chloropyrid-4-yl- | CH3 |
| 53 | CF3 | 2,6-dichloropyrid-4-yl- | CH3 |
| 54 | CClCF2 | 2,6-dichloropyrid-4-yl- | CH3 |
| 55 | CF3 | 3,5-dichlorophenyl- | CH3CH2 |
| 56 | CClCF2 | 3,5-dichlorophenyl- | CH3CH2 |
| 57 | CF3 | 3,4,5-trichlorophenyl- | CH3CH2 |
| 58 | CClCF2 | 3,4,5-trichlorophenyl- | CH3CH2 |
| 59 | CF3 | 3,5-dichloro-4-fluorophenyl- | CH3CH2 |
| 60 | CClCF2 | 3,5-dichloro-4-fluorophenyl- | CH3CH2 |
| 61 | CF3 | 3-trifluoromethylphenyl- | CH3CH2 |
| 62 | CClCF2 | 3-trifluoromethylphenyl- | CH3CH2 |
| 63 | CF3 | 3,5-bis(trifluoromethyl)phenyl- | CH3CH2 |
| 64 | CClCF2 | 3,5-bis(trifluoromethyl)phenyl- | CH3CH2 |
| 65 | CF3 | 3-chloro-5-trifluoromethylphenyl- | CH3CH2 |
| 66 | CClCF2 | 3-chloro-5-trifluoromethylphenyl- | CH3CH2 |
| 67 | CF3 | 3,4-dichlorophenyl- | CH3CH2 |
| 68 | CClCF2 | 3,4-dichlorophenyl- | CH3CH2 |
| 69 | CF3 | 2-chloropyrid-4-yl- | CH3CH2 |
| 70 | CClCF2 | 2-chloropyrid-4-yl- | CH3CH2 |
| 71 | CF3 | 2,6-dichloropyrid-4-yl- | CH3CH2 |
| 72 | CClCF2 | 2,6-dichloropyrid-4-yl- | CH3CH2 |
| 73 | CF3 | 3,5-dichlorophenyl- | CF3 |
| 74 | CClCF2 | 3,5-dichlorophenyl- | CF3 |
| 75 | CF3 | 3,4,5-trichlorophenyl- | CF3 |
| 76 | CClCF2 | 3,4,5-trichlorophenyl- | CF3 |
| 77 | CF3 | 3,5-dichloro-4-fluorophenyl- | CF3 |
| 78 | CClCF2 | 3,5-dichloro-4-fluorophenyl- | CF3 |
| 79 | CF3 | 3-trifluoromethylphenyl- | CF3 |
| 80 | CClCF2 | 3-trifluoromethylphenyl- | CF3 |
| 81 | CF3 | 3,5-bis(trifluoromethyl)phenyl- | CF3 |
| 82 | CClCF2 | 3,5-bis(trifluoromethyl)phenyl- | CF3 |
| 83 | CF3 | 3-chloro-5-trifluoromethylphenyl- | CF3 |
| 84 | CClCF2 | 3-chloro-5-trifluoromethylphenyl- | CF3 |
| 85 | CF3 | 3,4-dichlorophenyl- | CF3 |
| 86 | CClCF2 | 3,4-dichlorophenyl- | CF3 |
| 87 | CF3 | 2-chloropyrid-4-yl- | CF3 |
| 88 | CClCF2 | 2-chloropyrid-4-yl- | CF3 |
| 89 | CF3 | 2,6-dichloropyrid-4-yl- | CF3 |
| 90 | CClCF2 | 2,6-dichloropyrid-4-yl- | CF3 |
| 91 | CF3 | 3,5-dichlorophenyl- | F |
| 92 | CClCF2 | 3,5-dichlorophenyl- | F |
| 93 | CF3 | 3,4,5-trichlorophenyl- | F |
| 94 | CClCF2 | 3,4,5-trichlorophenyl- | F |
| 95 | CF3 | 3,5-dichloro-4-fluorophenyl- | F |
| 96 | CClCF2 | 3,5-dichloro-4-fluorophenyl- | F |
| 97 | CF3 | 3-trifluoromethylphenyl- | F |
| 98 | CClCF2 | 3-trifluoromethylphenyl- | F |
| 99 | CF3 | 3,5-bis(trifluoromethyl)phenyl- | F |
| 100 | CClCF2 | 3,5-bis(trifluoromethyl)phenyl- | F |
| 101 | CF3 | 3-chloro-5-trifluoromethylphenyl- | F |
| 102 | CClCF2 | 3-chloro-5-trifluoromethylphenyl- | F |
| 103 | CF3 | 3,4-dichlorophenyl- | F |
| 104 | CClCF2 | 3,4-dichlorophenyl- | F |
| 105 | CF3 | 2-chloropyrid-4-yl- | F |
| 106 | CClCF2 | 2-chloropyrid-4-yl- | F |
| 107 | CF3 | 2,6-dichloropyrid-4-yl- | F |
| 108 | CClCF2 | 2,6-dichloropyrid-4-yl- | F |

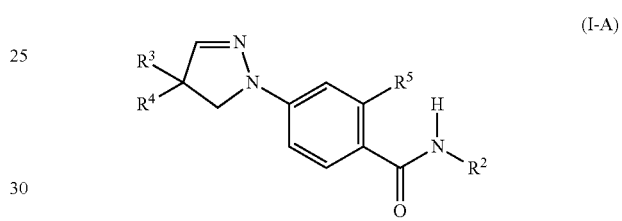

(I-A)

Table 1
Table 1 provides 108 compounds of formula I-A wherein R2 is 1-oxo-tetrahydrofuran-3-yl- and R3, R4 and R5 are as defined in Table P.
Table 2
Table 2 provides 108 compounds of formula I-A wherein R2 is 1-oxo-thietan-3-yl- and R3, R4 and R5 are as defined in Table P.
Table 3
Table 3 provides 108 compounds of formula I-A wherein R2 is 1,1-dioxo-tetrahydrofuran-3-yl- and R3, R4 and R5 are as defined in Table P.
Table 4
Table 4 provides 108 compounds of formula I-A wherein R2 is 1,1-dioxo-thietan-3-yl- and R3, R4 and R5 are as defined in Table P.
Table 5
Table 5 provides 108 compounds of formula I-A wherein R2 is (1,1-dioxo-thietan-2-yl)methyl- and R3, R4 and R5 are as defined in Table P.
Table 6
Table 6 provides 108 compounds of formula I-A wherein R2 is 4-oxo-2-(trifluoromethyl)-1,3-oxazinan-5-yl- and R3, R4 and R5 are as defined in Table P.
Table 7
Table 7 provides 108 compounds of formula I-A wherein R2 is 3-oxo-2-(cyclopropylmethyl)-isoxazolidin-4-yl- and R3, R4 and R5 are as defined in Table P.
Table 8
Table 8 provides 108 compounds of formula I-A wherein R2 is 2,5-dioxo-1-(2,2,2-trifluoroethyl)pyrrolidin-3-yl- and R3, R4 and R5 are as defined in Table P.
Table 9
Table 9 provides 108 compounds of formula I-A wherein R2 is N-(3,3,3-trifluoropropyl)acetamid-2-yl- and R3, R4 and R5 are as defined in Table P.

Table 10
Table 10 provides 108 compounds of formula I-A wherein R2 is N-(2,2,2-trifluoroethyl)acetamid-2-yl- and R3, R4 and R5 are as defined in Table P.

Table 11
Table 11 provides 108 compounds of formula I-A wherein R2 is 2-methoxy-ethyl- and R3, R4 and R5 are as defined in Table P.

Table 12
Table 12 provides 108 compounds of formula I-A wherein R2 is 3-chloroprop-1-yl- and R3, R4 and R5 are as defined in Table P.

Table 13
Table 13 provides 108 compounds of formula I-A wherein R2 is 3,3,3-trifluoro-propyl- and R3, R4 and R5 are as defined in Table P.

Table 14
Table 14 provides 108 compounds of formula I-A wherein R2 is (thietan-2-yl)methyl- and R3, R4 and R5 are as defined in Table P.

Table 15
Table 15 provides 108 compounds of formula I-A wherein R2 is 1-oxo-thietan-3-yl-methyl- and R3, R4 and R5 are as defined in Table P.

Table 16
Table 16 provides 108 compounds of formula I-A wherein R2 is (oxetan-2-yl)-methyl- and R3, R4 and R5 are as defined in Table P.

Table 17
Table 17 provides 108 compounds of formula I-A wherein R2 is (thiazol-4-yl)methyl- and R3, R4 and R5 are as defined in Table P.

Table 18
Table 18 provides 108 compounds of formula I-A wherein R2 is (2-pyrimid-2-yl)methyl- and R3, R4 and R5 are as defined in Table P.

Table 19
Table 19 provides 108 compounds of formula I-A wherein R2 is (thietan-3-yl)methyl- and R3, R4 and R5 are as defined in Table P.

Table 20
Table 20 provides 108 compounds of formula I-A wherein R2 is (1,1-dioxo-thietan-3-yl)methyl- and R3, R4 and R5 are as defined in Table P.

Table 21
Table 21 provides 108 compounds of formula I-A wherein R2 is (N-methoxypiperid-4-yl)methyl- and R3, R4 and R5 are as defined in Table P.

Table 22
Table 22 provides 108 compounds of formula I-A wherein R2 is (tetrahydrofuran-2-yl)-methyl- and R3, R4 and R5 are as defined in Table P.

Table 23
Table 23 provides 108 compounds of formula I-A wherein R2 is (2-pyridyl)methyl- and R3, R4 and R5 are as defined in Table P.

Table 24
Table 24 provides 108 compounds of formula I-A wherein R2 is phenylmethyl- and R3, R4 and R5 are as defined in Table P.

Table 25
Table 25 provides 108 compounds of formula I-A wherein R2 is (cyclobutyl)methyland R3, R4 and R5 are as defined in Table P.

Table 26
Table 26 provides 108 compounds of formula I-A wherein R2 is (2-fluorophenyl)methyl- and R3, R4 and R5 are as defined in Table P.

Table 27
Table 27 provides 108 compounds of formula I-A wherein R2 is N-ethylacetamid-2-yl- and R3, R4 and R5 are as defined in Table P.

Table 28
Table 28 provides 108 compounds of formula I-A wherein R2 is N-(but-2-yl)acetamid-2-yl- and R3, R4 and R5 are as defined in Table P.

Table 29
Table 29 provides 108 compounds of formula I-A wherein R2 is 2,2,2-trifluoro-ethyl- and R3, R4 and R5 are as defined in Table P.

Table 30
Table 30 provides 108 compounds of formula I-A wherein R2 is tetrahydrofuran-2-yl- and R3, R4 and R5 are as defined in Table P.

Table 31
Table 31 provides 108 compounds of formula I-A wherein R2 is thietan-3-yl- and R3, R4 and R5 are as defined in Table P.

Table 32
Table 32 provides 108 compounds of formula I-A wherein R2 is 3-oxo-2-(3,3,3-trifluoro-propyl)-isoxazolidin-4-yl- and R3, R4 and R5 are as defined in Table P.

Table 33
Table 33 provides 108 compounds of formula I-A wherein R2 is 3-oxetanyl- and R3, R4 and R5 are as defined in Table P.

Table 34
Table 34 provides 108 compounds of formula I-A wherein R2 is tetrahydrofuran-2-yl- and R3, R4 and R5 are as defined in Table P.

Table 35
Table 35 provides 108 compounds of formula I-A wherein R2 is 2-oxo-1-(2,2,2-trifluoroethyl)pyrrolidin-3-yl- and R3, R4 and R5 are as defined in Table P.

Table 36
Table 36 provides 108 compounds of formula I-A wherein R2 is cyclobutyl- and R3, R4 and R5 are as defined in Table P.

Table 37
Table 37 provides 108 compounds of formula I-A wherein R2 is 2-norbornyl- and R3, R4 and R5 are as defined in Table P.

Table 38
Table 38 provides 108 compounds of formula I-A wherein R2 is cyclopropyl- and R3, R4 and R5 are as defined in Table P.

Table 39
Table 39 provides 108 compounds of formula I-A wherein R2 is 3-(hydroxyimino)-cyclobutyl- and R3, R4 and R5 are as defined in Table P.

Table 40
Table 40 provides 108 compounds of formula I-A wherein R2 is 3-(ethoxyimino)-cyclobutyl- and R3, R4 and R5 are as defined in Table P.

Table 41
Table 41 provides 108 compounds of formula I-A wherein R2 is 2-oxopyrrolidin-3-yl- and R3, R4 and R5 are as defined in Table P.

Table 42
Table 42 provides 108 compounds of formula I-A wherein R2 is 3-oxo-2-(2,2,2-trifluoro-ethyl)-isoxazolidin-4-yl- and R3, R4 and R5 are as defined in Table P.

Table 43
Table 43 provides 108 compounds of formula I-A wherein R2 is 3-oxo-2-(2,2-difluoro-ethyl)-isoxazolidin-4-yl- and R3, R4 and R5 are as defined in Table P.
Table 44
Table 44 provides 108 compounds of formula I-A wherein R2 is 3-methyloxetan-3-yl- and R3, R4 and R5 are as defined in Table P.
Table 45
Table 45 provides 108 compounds of formula I-A wherein R2 is 1-phenyleth-1-yl- and R3, R4 and R5 are as defined in Table P.
Table 46
Table 46 provides 108 compounds of formula I-A wherein R2 is 1-cyanocyclopropyl- and R3, R4 and R5 are as defined in Table P.
Table 47
Table 47 provides 108 compounds of formula I-A wherein R2 is 2-fluoro-cycloprop-1-yl- and R3, R4 and R5 are as defined in Table P.
Table 48
Table 48 provides 108 compounds of formula I-A wherein R2 is 1,1,1-trifluoroprop-2-yl- and R3, R4 and R5 are as defined in Table P.
Table 49
Table 49 provides 108 compounds of formula I-A wherein R2 is 2-methylsulfanyl-ethyl- and R3, R4 and R5 are as defined in Table P.
Table 50
Table 50 provides 108 compounds of formula I-A wherein R2 is N-methoxyethaniminyland R3, R4 and R5 are as defined in Table P.
Table 51
Table 51 provides 108 compounds of formula I-A wherein R2 is 3-(methoxyimino)-cyclobutyl- and R3, R4 and R5 are as defined in Table P.
Table 52
Table 52 provides 108 compounds of formula I-A wherein R2 is N-ethoxyethaniminyland R3, R4 and R5 are as defined in Table P.
Table 53
Table 53 provides 108 compounds of formula I-A wherein R2 is 3-oxo-2-ethylisoxazolidin-4-yl- and R3, R4 and R5 are as defined in Table P.
Table 54
Table 54 provides 108 compounds of formula I-A wherein R2 is 2-oxo-1-(ethyl)pyrrolidin-3-yl- and R3, R4 and R5 are as defined in Table P.
Table 55
Table 55 provides 108 compounds of formula I-A wherein R2 is but-1-yl- and R3, R4 and R5 are as defined in Table P.
Table 56
Table 56 provides 108 compounds of formula I-A wherein R2 is but-2-yl- and R3, R4 and R5 are as defined in Table P.
Table 57
Table 57 provides 108 compounds of formula I-A wherein R2 is 1-methoxy-prop-2-yl- and R3, R4 and R5 are as defined in Table P.
Table 58
Table 58 provides 108 compounds of formula I-A wherein R2 is 2-oxo-1-methylpyrrolidin-3-yl- and R3, R4 and R5 are as defined in Table P.
Table 59
Table 59 provides 108 compounds of formula I-A wherein R2 is 3-oxo-2-methylisoxazolidin-4-yl- and R3, R4 and R5 are as defined in Table P.
Table 60
Table 60 provides 108 compounds of formula I-A wherein R2 is prop-2-yl- and R3, R4 and R5 are as defined in Table P.
Table 61
Table 61 provides 108 compounds of formula I-A wherein R2 is methyl- and R3, R4 and R5 are as defined in Table P.
Table 62
Table 62 provides 108 compounds of formula I-A wherein R2 is ethyl- and R3, R4 and R5 are as defined in Table P.
Table 63
Table 63 provides 108 compounds of formula I-A wherein R2 is prop-1-yl and R3, R4 and R5 are as defined in Table P.
Table 64
Table 64 provides 108 compounds of formula I-A wherein R2 is 2,2-difluoro-ethyl- and R3, R4 and R5 are as defined in Table P.
Table 65
Table 65 provides 108 compounds of formula I-A wherein R2 is 1-oxo-thietan-3-yl-ethyl- and R3, R4 and R5 are as defined in Table P.
Table 66
Table 66 provides 108 compounds of formula I-A wherein R2 is tetrahydropyran-4-yl- and R3, R4 and R5 are as defined in Table P.
Table 67
Table 67 provides 108 compounds of formula I-A wherein R2 is 2-fluoro-ethyl- and R3, R4 and R5 are as defined in Table P.
Table 68
Table 68 provides 108 compounds of formula I-A wherein R2 is thietan-3-yl-ethyl- and R3, R4 and R5 are as defined in Table P.
Table 69
Table 69 provides 108 compounds of formula I-A wherein R2 is cyclopentyl- and R3, R4 and R5 are as defined in Table P.
Table 70
Table 70 provides 108 compounds of formula I-A wherein R2 is (2-cyclopropyl-1-oxa-3,4-diazol-5-yl)methyl- and R3, R4 and R5 are as defined in Table P.
Table 71
Table 71 provides 108 compounds of formula I-A wherein R2 is 2-thiazolinyl and R3, R4 and R5 are as defined in Table P.
Table 72
Table 72 provides 108 compounds of formula I-A wherein R2 is 4-cyanopyrimid-2-yl- and R3, R4 and R5 are as defined in Table P.
Table 73
Table 73 provides 108 compounds of formula I-A wherein R2 is (pyrimidin-5-yl)methyl- and R3, R4 and R5 are as defined in Table P.
Table 74
Table 74 provides 108 compounds of formula I-A wherein R2 is 2-chloropyrid-5-yl- and R3, R4 and R5 are as defined in Table P.
Table 75
Table 75 provides 108 compounds of formula I-A wherein R2 is (pyrazin-2-yl)methyl- and R3, R4 and R5 are as defined in Table P.
Table 76
Table 76 provides 108 compounds of formula I-A wherein R2 is (2-chlorothiazol-5-yl)methyl- and R3, R4 and R5 are as defined in Table P.

Table 77
Table 77 provides 108 compounds of formula I-A wherein R2 is 2-methylsulfinyl-ethyl- and R3, R4 and R5 are as defined in Table P.
Table 78
Table 78 provides 108 compounds of formula I-A wherein R2 is 2-(methylsulfonyl)-ethyl- and R3, R4 and R5 are as defined in Table P.
Table 79
Table 79 provides 108 compounds of formula I-A wherein R2 is N-methylpiperidin-4-yl- and R3, R4 and R5 are as defined in Table P.
Table 80
Table 80 provides 108 compounds of formula I-A wherein R2 is N-(3,3,3-trifluoropropanoyl)piperidin-4-yl- and R3, R4 and R5 are as defined in Table P.
Table 81
Table 81 provides 108 compounds of formula I-A wherein R2 is 1-(2-chloro-pyrid-5-yl)eth-1-yl- and R3, R4 and R5 are as defined in Table P.
Table 82
Table 82 provides 108 compounds of formula I-A wherein R2 is N-cyclopropylacetamid-2-yl- and R3, R4 and R5 are as defined in Table P.
Table 83
Table 83 provides 108 compounds of formula I-A wherein R2 is (2-chloro-pyrid-3-yl)-methyl- and R3, R4 and R5 are as defined in Table P.
Table 84
Table 84 provides 108 compounds of formula I-A wherein R2 is 3-oxo-2-propargylisoxazolidin-4-yl- and R3, R4 and R5 are as defined in Table P.
Table 85
Table 85 provides 108 compounds of formula I-A wherein R2 is (3-fluorophenyl)methyl- and R3, R4 and R5 are as defined in Table P.
Table 86
Table 86 provides 108 compounds of formula I-A wherein R2 is (2-fluorophenyl)methyl- and R3, R4 and R5 are as defined in Table P.
Table 87
Table 87 provides 108 compounds of formula I-A wherein R2 is (1-oxo-thietan-3-yl)methyl- and R3, R4 and R5 are as defined in Table P.
Table 88
Table 88 provides 108 compounds of formula I-A wherein R2 is N-(cyclopropyl)acetamid-2-yl- and R3, R4 and R5 are as defined in Table P.
Table 89
Table 89 provides 108 compounds of formula I-A wherein R2 is (4-chlorophenyl)methyl- and R3, R4 and R5 are as defined in Table P.
Table 90
Table 90 provides 108 compounds of formula I-A wherein R2 is 1-methyl-1-(pyrid-2-yl)eth-1-yl- and R3, R4 and R5 are as defined in Table P.
Table 91
Table 91 provides 108 compounds of formula I-A wherein R2 is 1-(2-pyridyl)cyclopropyl- and R3, R4 and R5 are as defined in Table P.
Table 92
Table 92 provides 108 compounds of formula I-A wherein R2 is (2-chloro-pyrid-5-yl)-methyl- and R3, R4 and R5 are as defined in Table P.
Table 93
Table 93 provides 108 compounds of formula I-A wherein R2 is (2-chloro-pyrid-4-yl)-methyl- and R3, R4 and R5 are as defined in Table P.
Table 94
Table 94 provides 108 compounds of formula I-A wherein R2 is N-(benzyl)acetamid-2-yl- and R3, R4 and R5 are as defined in Table P.
Table 95
Table 95 provides 108 compounds of formula I-A wherein R2 is N-(2-fluorobenzyl)acetamid-2-yl- and R3, R4 and R5 are as defined in Table P.

TABLE Q

| | R3 | R4 |
|---|---|---|
| 1 | CF3 | 3,5-dichlorophenyl- |
| 2 | CClF2 | 3,5-dichlorophenyl- |
| 3 | CF3 | 3,4,5-trichlorophenyl- |
| 4 | CClF2 | 3,4,5-trichlorophenyl- |
| 5 | CF3 | 3,5-dichloro-4-fluorophenyl- |
| 6 | CClF2 | 3,5-dichloro-4-fluorophenyl- |
| 7 | CF3 | 3-trifluoromethylphenyl- |
| 8 | CClF2 | 3-trifluoromethylphenyl- |
| 9 | CF3 | 3,5-bis(trifluoromethyl)phenyl- |
| 10 | CClF2 | 3,5-bis(trifluoromethyl)phenyl- |
| 11 | CF3 | 3-chloro-5-trifluoromethylphenyl- |
| 12 | CClF2 | 3-chloro-5-trifluoromethylphenyl- |
| 13 | CF3 | 3,4-dichlorophenyl- |
| 14 | CClF2 | 3,4-dichlorophenyl- |
| 15 | CF3 | 2-chloropyrid-4-yl- |
| 16 | CClF2 | 2-chloropyrid-4-yl- |
| 17 | CF3 | 2,6-dichloropyrid-4-yl- |
| 18 | CClF2 | 2,6-dichloropyrid-4-yl- |

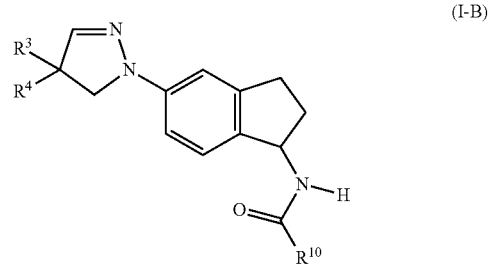

(I-B)

Table 96
Table 96 provides 18 compounds of formula I-B wherein R10 is 2-methoxy-ethyl- and R3 and R4 are as defined in Table Q.
Table 97
Table 97 provides 18 compounds of formula I-B wherein R10 is 2-(methylsulfonyl)-ethyl- and R3 and R4 are as defined in Table Q.
Table 98
Table 98 provides 18 compounds of formula I-B wherein R10 is 2-methylsulfinyl-ethyl- and R3 and R4 are defined in Table Q.
Table 99
Table 99 provides 18 compounds of formula I-B wherein R10 is 2-methylsulfanyl-ethyl- and R3 and R4 are defined in Table Q.
Table 100
Table 100 provides 18 compounds of formula I-B wherein R10 is 1-methoxy-prop-2-yl- and R3 and R4 are defined in Table Q.

Table 101
Table 101 provides 18 compounds of formula I-B wherein R10 is 1-cyanocyclopropyl- and R3 and R4 are as defined in Table Q.
Table 102
Table 102 provides 18 compounds of formula I-B wherein R10 is 2-fluoro-ethyl- and R3 and R4 are as defined in Table Q.
Table 103
Table 103 provides 18 compounds of formula I-B wherein R10 is 3-chloroprop-1-yl- and R3 and R4 are as defined in Table Q.
Table 104
Table 104 provides 18 compounds of formula I-B wherein R10 is 3,3,3-trifluoro-propyl- and R3 and R4 are as defined in Table Q.
Table 105
Table 105 provides 18 compounds of formula I-B wherein R10 is 2,2,2-trifluoro-ethyl- and R3 and R4 are as defined in Table Q.
Table 106
Table 106 provides 18 compounds of formula I-B wherein R10 is 1,1,1-trifluoroprop-2-yl- and R3 and R4 are as defined in Table Q.
Table 107
Table 107 provides 18 compounds of formula I-B wherein R10 is 2,2-difluoro-ethyl- and R3 and R4 are as defined in Table Q.
Table 108
Table 108 provides 18 compounds of formula I-B wherein R10 is methyl- and R3 and R4 are as defined in Table Q.
Table 109
Table 109 provides 18 compounds of formula I-B wherein R10 is ethyl- and R3 and R4 are as defined in Table Q.
Table 110
Table 110 provides 18 compounds of formula I-B wherein R10 is prop-1-yl and R3 and R4 are as defined in Table Q.
Table 111
Table 111 provides 18 compounds of formula I-B wherein R10 is but-1-yl- and R3 and R4 are as defined in Table Q.
Table 112
Table 112 provides 18 compounds of formula I-B wherein R10 is but-2-yl- and R3 and R4 are as defined in Table Q.
Table 113
Table 113 provides 18 compounds of formula I-B wherein R10 is prop-2-yl- and R3 and R4 are as defined in Table Q.
Table 114
Table 114 provides 18 compounds of formula I-B wherein R10 is 4-cyanophen-1-yl- and R3 and R4 are as defined in Table Q.
Table 115
Table 115 provides 18 compounds of formula I-B wherein R10 is (4-chlorophenyl)methyl- and R3 and R4 are as defined in Table Q.
Table 116
Table 116 provides 18 compounds of formula I-B wherein R10 is 2-fluoro-cycloprop-1-yl- and R3 and R4 are as defined in Table Q.
Table 117
Table 117 provides 18 compounds of formula I-B wherein R10 is cyclobutyl- and R3 and R4 are as defined in Table Q.
Table 118
Table 118 provides 18 compounds of formula I-B wherein R10 is cyclopropyl- and R3 and R4 are as defined in Table Q.
Table 119
Table 119 provides 18 compounds of formula I-B wherein R10 is cyclopentyl- and R3 and R4 are as defined in Table Q.
Table 120
Table 120 provides 18 compounds of formula I-B wherein R10 is (N-methoxypiperid-4-yl)methyl- and R3 and R4 are as defined in Table Q.
Table 121
Table 121 provides 18 compounds of formula I-B wherein R10 is 1-oxo-tetrahydrofuran-3-yl- and R3 and R4 are as defined in Table Q.
Table 122
Table 122 provides 18 compounds of formula I-B wherein R10 is 1-oxo-thietan-3-yl- and R3 and R4 are as defined in Table Q.
Table 123
Table 123 provides 18 compounds of formula I-B wherein R10 is 1,1-dioxo-tetrahydrofuran-3-yl- and R3 and R4 are as defined in Table Q.
Table 124
Table 124 provides 18 compounds of formula I-B wherein R10 is 1,1-dioxo-thietan-3-yl- and R3 and R4 are as defined in Table Q.
Table 125
Table 125 provides 18 compounds of formula I-B wherein R10 is tetrahydrofuran-2-yl- and R3 and R4 are as defined in Table Q.
Table 126
Table 126 provides 18 compounds of formula I-B wherein R10 is thietan-3-yl- and R3 and R4 are as defined in Table Q.
Table 127
Table 127 provides 18 compounds of formula I-B wherein R10 is 3-oxetanyl- and R3 and R4 are as defined in Table Q.
Table 128
Table 128 provides 18 compounds of formula I-B wherein R10 is tetrahydrofuran-2-yl- and R3 and R4 are as defined in Table Q.
Table 129
Table 129 provides 18 compounds of formula I-B wherein R10 is tetrahydropyran-4-yl- and R3 and R4 are as defined in Table Q.
Table 130
Table 130 provides 18 compounds of formula I-B wherein R10 is 2-chloropyrid-4-yl and R3 and R4 are as defined in Table Q.
Table 131
Table 131 provides 18 compounds of formula I-B wherein R10 is 2-chloropyrid-5-yl- and R3 and R4 are as defined in Table Q.
Table 132
Table 132 provides 18 compounds of formula I-B wherein R10 is pyrid-4-yl and R3 and R4 are as defined in Table Q.
Table 133
Table 133 provides 18 compounds of formula I-B wherein R10 is pyrid-3-yl and R3 and R4 are as defined in Table Q.
Table 134
Table 134 provides 18 compounds of formula I-B wherein R10 is 1-oxo-pyrid-4-yl and R3 and R4 are as defined in Table Q.

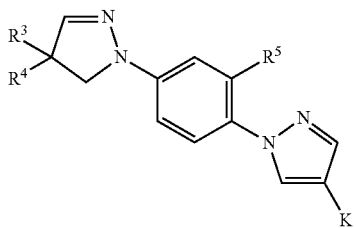
(I-C)

Table 135
Table 135 provides 108 compounds of formula I-C wherein k is CN and R3, R4 and R5 are as defined in Table P.
Table 136
Table 136 provides 108 compounds of formula I-C wherein k is CF3 and R3, R4 and R5 are as defined in Table P.

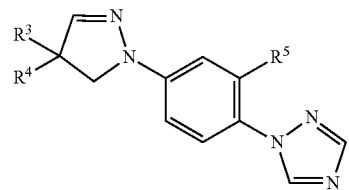
(I-D)

Table 137
Table 137 provides 108 compounds of formula I-D and R3, R4 and R5 are as defined in Table P.

TABLE R

|    | R3    | R4                              | R5     | R6a |
|----|-------|---------------------------------|--------|-----|
| 1  | CF3   | 3,5-dichlorophenyl-             | Br     | H   |
| 2  | CClF2 | 3,5-dichlorophenyl-             | Br     | H   |
| 3  | CF3   | 3,4,5-trichlorophenyl-          | Br     | H   |
| 4  | CClF2 | 3,4,5-trichlorophenyl-          | Br     | H   |
| 5  | CF3   | 3,5-dichloro-4-fluorophenyl-    | Br     | H   |
| 6  | CClF2 | 3,5-dichloro-4-fluorophenyl-    | Br     | H   |
| 7  | CF3   | 3-trifluoromethylphenyl-        | Br     | H   |
| 8  | CClF2 | 3-trifluoromethylphenyl-        | Br     | H   |
| 9  | CF3   | 3,5-bis(trifluoromethyl)phenyl- | Br     | H   |
| 10 | CClF2 | 3,5-bis(trifluoromethyl)phenyl- | Br     | H   |
| 11 | CF3   | 3-chloro-5-trifluoromethylphenyl- | Br   | H   |
| 12 | CClF2 | 3-chloro-5-trifluoromethylphenyl- | Br   | H   |
| 13 | CF3   | 3,5-dichlorophenyl-             | Cl     | H   |
| 14 | CClF2 | 3,5-dichlorophenyl-             | Cl     | H   |
| 15 | CF3   | 3,4,5-trichlorophenyl-          | Cl     | H   |
| 16 | CClF2 | 3,4,5-trichlorophenyl-          | Cl     | H   |
| 17 | CF3   | 3,5-dichloro-4-fluorophenyl-    | Cl     | H   |
| 18 | CClF2 | 3,5-dichloro-4-fluorophenyl-    | Cl     | H   |
| 19 | CF3   | 3-trifluoromethylphenyl-        | Cl     | H   |
| 20 | CClF2 | 3-trifluoromethylphenyl-        | Cl     | H   |
| 21 | CF3   | 3,5-bis(trifluoromethyl)phenyl- | Cl     | H   |
| 22 | CClF2 | 3,5-bis(trifluoromethyl)phenyl- | Cl     | H   |
| 23 | CF3   | 3-chloro-5-trifluoromethylphenyl- | Cl   | H   |
| 24 | CClF2 | 3-chloro-5-trifluoromethylphenyl- | Cl   | H   |
| 25 | CF3   | 3,5-dichlorophenyl-             | CH3    | H   |
| 26 | CClF2 | 3,5-dichlorophenyl-             | CH3    | H   |
| 27 | CF3   | 3,4,5-trichlorophenyl-          | CH3    | H   |
| 28 | CClF2 | 3,4,5-trichlorophenyl-          | CH3    | H   |
| 29 | CF3   | 3,5-dichloro-4-fluorophenyl-    | CH3    | H   |
| 30 | CClF2 | 3,5-dichloro-4-fluorophenyl-    | CH3    | H   |
| 31 | CF3   | 3-trifluoromethylphenyl-        | CH3    | H   |
| 32 | CClF2 | 3-trifluoromethylphenyl-        | CH3    | H   |
| 33 | CF3   | 3,5-bis(trifluoromethyl)phenyl- | CH3    | H   |
| 34 | CClF2 | 3,5-bis(trifluoromethyl)phenyl- | CH3    | H   |
| 35 | CF3   | 3-chloro-5-trifluoromethylphenyl- | CH3  | H   |
| 36 | CClF2 | 3-chloro-5-trifluoromethylphenyl- | CH3  | H   |
| 37 | CF3   | 3,5-dichlorophenyl-             | CH3CH2 | H   |
| 38 | CClF2 | 3,5-dichlorophenyl-             | CH3CH2 | H   |
| 39 | CF3   | 3,4,5-trichlorophenyl-          | CH3CH2 | H   |
| 40 | CClF2 | 3,4,5-trichlorophenyl-          | CH3CH2 | H   |
| 41 | CF3   | 3,5-dichloro-4-fluorophenyl-    | CH3CH2 | H   |
| 42 | CClF2 | 3,5-dichloro-4-fluorophenyl-    | CH3CH2 | H   |
| 43 | CF3   | 3-trifluoromethylphenyl-        | CH3CH2 | H   |
| 44 | CClF2 | 3-trifluoromethylphenyl-        | CH3CH2 | H   |
| 45 | CF3   | 3,5-bis(trifluoromethyl)phenyl- | CH3CH2 | H   |
| 46 | CClF2 | 3,5-bis(trifluoromethyl)phenyl- | CH3CH2 | H   |
| 47 | CF3   | 3-chloro-5-trifluoromethylphenyl- | CH3CH2 | H |
| 48 | CClF2 | 3-chloro-5-trifluoromethylphenyl- | CH3CH2 | H |
| 49 | CF3   | 3,5-dichlorophenyl-             | Br     | CH3 |
| 50 | CClF2 | 3,5-dichlorophenyl-             | Br     | CH3 |
| 51 | CF3   | 3,4,5-trichlorophenyl-          | Br     | CH3 |
| 52 | CClF2 | 3,4,5-trichlorophenyl-          | Br     | CH3 |
| 53 | CF3   | 3,5-dichloro-4-fluorophenyl-    | Br     | CH3 |
| 54 | CClF2 | 3,5-dichloro-4-fluorophenyl-    | Br     | CH3 |
| 55 | CF3   | 3-trifluoromethylphenyl-        | Br     | CH3 |
| 56 | CClF2 | 3-trifluoromethylphenyl-        | Br     | CH3 |
| 57 | CF3   | 3,5-bis(trifluoromethyl)phenyl- | Br     | CH3 |
| 58 | CClF2 | 3,5-bis(trifluoromethyl)phenyl- | Br     | CH3 |
| 59 | CF3   | 3-chloro-5-trifluoromethylphenyl- | Br   | CH3 |
| 60 | CClF2 | 3-chloro-5-trifluoromethylphenyl- | Br   | CH3 |
| 61 | CF3   | 3,5-dichlorophenyl-             | Cl     | CH3 |
| 62 | CClF2 | 3,5-dichlorophenyl-             | Cl     | CH3 |
| 63 | CF3   | 3,4,5-trichlorophenyl-          | Cl     | CH3 |
| 64 | CClF2 | 3,4,5-trichlorophenyl-          | Cl     | CH3 |
| 65 | CF3   | 3,5-dichloro-4-fluorophenyl-    | Cl     | CH3 |
| 66 | CClF2 | 3,5-dichloro-4-fluorophenyl-    | Cl     | CH3 |
| 67 | CF3   | 3-trifluoromethylphenyl-        | Cl     | CH3 |
| 68 | CClF2 | 3-trifluoromethylphenyl-        | Cl     | CH3 |
| 69 | CF3   | 3,5-bis(trifluoromethyl)phenyl- | Cl     | CH3 |
| 70 | CClF2 | 3,5-bis(trifluoromethyl)phenyl- | Cl     | CH3 |
| 71 | CF3   | 3-chloro-5-trifluoromethylphenyl- | Cl   | CH3 |
| 72 | CClF2 | 3-chloro-5-trifluoromethylphenyl- | Cl   | CH3 |
| 73 | CF3   | 3,5-dichlorophenyl-             | CH3    | CH3 |
| 74 | CClF2 | 3,5-dichlorophenyl-             | CH3    | CH3 |
| 75 | CF3   | 3,4,5-trichlorophenyl-          | CH3    | CH3 |
| 76 | CClF2 | 3,4,5-trichlorophenyl-          | CH3    | CH3 |
| 77 | CF3   | 3,5-dichloro-4-fluorophenyl-    | CH3    | CH3 |
| 78 | CClF2 | 3,5-dichloro-4-fluorophenyl-    | CH3    | CH3 |
| 79 | CF3   | 3-trifluoromethylphenyl-        | CH3    | CH3 |
| 80 | CClF2 | 3-trifluoromethylphenyl-        | CH3    | CH3 |
| 81 | CF3   | 3,5-bis(trifluoromethyl)phenyl- | CH3    | CH3 |
| 82 | CClF2 | 3,5-bis(trifluoromethyl)phenyl- | CH3    | CH3 |
| 83 | CF3   | 3-chloro-5-trifluoromethylphenyl- | CH3  | CH3 |
| 84 | CClF2 | 3-chloro-5-trifluoromethylphenyl- | CH3  | CH3 |
| 85 | CF3   | 3,5-dichlorophenyl-             | CH3CH2 | CH3 |
| 86 | CClF2 | 3,5-dichlorophenyl-             | CH3CH2 | CH3 |
| 87 | CF3   | 3,4,5-trichlorophenyl-          | CH3CH2 | CH3 |
| 88 | CClF2 | 3,4,5-trichlorophenyl-          | CH3CH2 | CH3 |
| 89 | CF3   | 3,5-dichloro-4-fluorophenyl-    | CH3CH2 | CH3 |
| 90 | CClF2 | 3,5-dichloro-4-fluorophenyl-    | CH3CH2 | CH3 |
| 91 | CF3   | 3-trifluoromethylphenyl-        | CH3CH2 | CH3 |
| 92 | CClF2 | 3-trifluoromethylphenyl-        | CH3CH2 | CH3 |
| 93 | CF3   | 3,5-bis(trifluoromethyl)phenyl- | CH3CH2 | CH3 |
| 94 | CClF2 | 3,5-bis(trifluoromethyl)phenyl- | CH3CH2 | CH3 |
| 95 | CF3   | 3-chloro-5-trifluoromethylphenyl- | CH3CH2 | CH3 |
| 96 | CClF2 | 3-chloro-5-trifluoromethylphenyl- | CH3CH2 | CH3 |

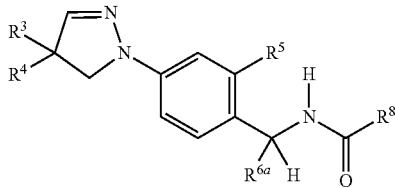
(I-E)

Table 138
Table 138 provides 96 compounds of formula I-E wherein R8 is 2-methoxy-ethyl- and R3, R4, R5, and R6a are as defined in Table R.
Table 139
Table 139 provides 96 compounds of formula I-E wherein R8 is 2-(methylsulfonyl)-ethyl- and R3, R4, R5, and R6a are as defined in Table R.
Table 140
Table 140 provides 96 compounds of formula I-E wherein R8 is 2-methylsulfinyl-ethyl- and R3, R4, R5, and R6a are as defined in Table R.
Table 141
Table 141 provides 96 compounds of formula I-E wherein R8 is 2-methylsulfanyl-ethyl- and R3, R4, R5, and R6a are as defined in Table R.
Table 142
Table 142 provides 96 compounds of formula I-E wherein R8 is 1-methoxy-prop-2-yl- and R3, R4, R5, and R6a are as defined in Table R.
Table 143
Table 143 provides 96 compounds of formula I-E wherein R8 is 1-cyanocyclopropyl- and R3, R4, R5, and R6a are as defined in Table R.
Table 144
Table 144 provides 96 compounds of formula I-E wherein R8 is 2-fluoro-ethyl- and R3, R4, R5, and R6a are as defined in Table R.
Table 145
Table 145 provides 96 compounds of formula I-E wherein R8 is 3-chloroprop-1-yl- and R3, R4, R5, and R6a are as defined in Table R.
Table 146
Table 146 provides 96 compounds of formula I-E wherein R8 is 3,3,3-trifluoro-propyl- and R3, R4, R5, and R6a are as defined in Table R.
Table 147
Table 147 provides 96 compounds of formula I-E wherein R8 is 2,2,2-trifluoro-ethyl- and R3, R4, R5, and R6a are as defined in Table R.
Table 148
Table 148 provides 96 compounds of formula I-E wherein R8 is 1,1,1-trifluoroprop-2-yl- and R3, R4, R5, and R6a are as defined in Table R.
Table 149
Table 149 provides 96 compounds of formula I-E wherein R8 is 2,2-difluoro-ethyl- and R3, R4, R5, and R6a are as defined in Table R.
Table 150
Table 150 provides 96 compounds of formula I-E wherein R8 is methyl- and R3, R4, R5, and R6a are as defined in Table R.
Table 151
Table 151 provides 96 compounds of formula I-E wherein R8 is ethyl- and R3, R4, R5, and R6a are as defined in Table R.
Table 152
Table 152 provides 96 compounds of formula I-E wherein R8 is prop-1-yl and R3, R4, R5, and R6a are as defined in Table R.
Table 153
Table 153 provides 96 compounds of formula I-E wherein R8 is but-1-yl- and R3, R4, R5, and R6a are as defined in Table R.
Table 154
Table 154 provides 96 compounds of formula I-E wherein R8 is but-2-yl- and R3, R4, R5, and R6a are as defined in Table R.
Table 155
Table 155 provides 96 compounds of formula I-E wherein R8 is prop-2-yl- and R3, R4, R5, and R6a are as defined in Table R.
Table 156
Table 156 provides 96 compounds of formula I-E wherein R8 is 4-cyanophen-1-yl- and R3, R4, R5, and R6a are as defined in Table R.
Table 157
Table 157 provides 96 compounds of formula I-E wherein R8 is (4-chlorophenyl)methyl- and R3, R4, R5, and R6a are as defined in Table R.
Table 158
Table 158 provides 96 compounds of formula I-E wherein R8 is 2-fluoro-cycloprop-1-yl- and R3, R4, R5, and R6a are as defined in Table R.
Table 159
Table 159 provides 96 compounds of formula I-E wherein R8 is cyclobutyl- and R3, R4, R5, and R6a are as defined in Table R.
Table 160
Table 160 provides 96 compounds of formula I-E wherein R8 is cyclopropyl- and R3, R4, R5, and R6a are as defined in Table R.
Table 161
Table 161 provides 96 compounds of formula I-E wherein R8 is cyclopentyl- and R3, R4, R5, and R6a are as defined in Table R.
Table 162
Table 162 provides 96 compounds of formula I-E wherein R8 is (N-methoxypiperid-4-yl)methyl- and R3, R4, R5, and R6a are as defined in Table R.
Table 163
Table 163 provides 96 compounds of formula I-E wherein R8 is 1-oxo-tetrahydrofuran-3-yl- and R3, R4, R5, and R6a are as defined in Table R.
Table 164
Table 164 provides 96 compounds of formula I-E wherein R8 is 1-oxo-thietan-3-yl- and R3, R4, R5, and R6a are as defined in Table R.
Table 165
Table 165 provides 96 compounds of formula I-E wherein R8 is 1,1-dioxo-tetrahydrofuran-3-yl- and R3, R4, R5, and R6a are as defined in Table R.
Table 166
Table 166 provides 96 compounds of formula I-E wherein R8 is 1,1-dioxo-thietan-3-yl- and R3, R4, R5, and R6a are as defined in Table R.
Table 167
Table 167 provides 96 compounds of formula I-E wherein R8 is tetrahydrofuran-2-yl- and R3, R4, R5, and R6a are as defined in Table R.
Table 168
Table 168 provides 96 compounds of formula I-E wherein R8 is thietan-3-yl- and R3, R4, R5, and R6a are as defined in Table R.
Table 169
Table 169 provides 96 compounds of formula I-E wherein R8 is 3-oxetanyl- and R3, R4, R5, and R6a are as defined in Table R.

Table 170
Table 170 provides 96 compounds of formula I-E wherein R8 is tetrahydrofuran-2-yl- and R3, R4, R5, and R6a are as defined in Table R.
Table 171
Table 171 provides 96 compounds of formula I-E wherein R8 is tetrahydropyran-4-yl- and R3, R4, R5, and R6a are as defined in Table R.
Table 172
Table 172 provides 96 compounds of formula I-E wherein R8 is 2-chloropyrid-4-yl and R3, R4, R5, and R6a are as defined in Table R.
Table 173
Table 173 provides 96 compounds of formula I-E wherein R8 is 2-chloropyrid-5-yl- and R3, R4, R5, and R6a are as defined in Table R.
Table 174
Table 174 provides 96 compounds of formula I-E wherein R8 is pyrid-4-yl and R3, R4, R5, and R6a are as defined in Table R.
Table 175
Table 175 provides 96 compounds of formula I-E wherein R8 is pyrid-3-yl and R3, R4, R5, and R6a are as defined in Table R.
Table 176
Table 176 provides 96 compounds of formula I-E wherein R8 is 1-oxo-pyrid-4-yl and R3, R4, R5, and R6a are as defined in Table R.
The compounds of the invention may be made as shown in the following Scheme.

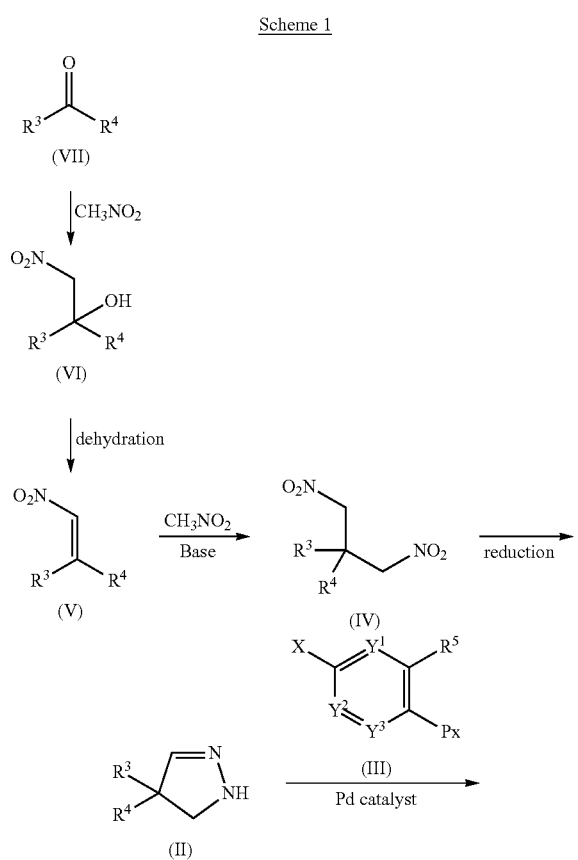

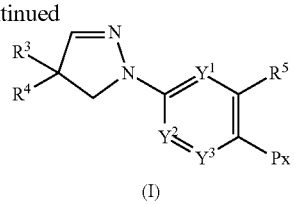

1) Compounds of formula I wherein Px is P as defined in the claims, a leaving group for example a halogen, such as bromo, a cyano or C(O)R wherein R is halogen, OH or $C_1$-$C_{15}$alkoxy, can be prepared by reacting compounds of formula III wherein Px is P as defined in the claims, a leaving group for example a halogen, such as bromo, a cyano or C(O)R wherein R is halogen, OH or $C_1$-$C_{15}$alkoxy and X is a leaving group, for example a halogen or a sulfonate such as chloro, bromo, or a triflate, with a compound of formula II, in a Buchwald-Hartwig coupling reaction, in the presence of a palladium catalyst, such as palladium acetate, [1,3-Bis(2,6-Diisopropylphenyl)imidazol-2-ylidene](3-chloropyridyl)palladium(II) dichloride, tris(dibenzylideneacetone)dipalladium(0) or tetrakis(triphenylphosphine)palladium in combination with a suitable monodentate ligand, such as 2-dicyclohexylphosphino-2',4',6'-triisopropylbiphenyl, 1,3-Bis(2,6-diisopropylphenyl)imidazol-2-ylidene, or bidentate ligand such as 4,5-bis(diphenylphosphino)-9,9-dimethylxanthene, 1,1'-bis(diphenylphosphanyl) ferrocene, 2,2'-bis(diphenylphosphino)-1,1'-binaphthyl in a suitable solvent, such as tert-butyl alcohol, tert-amylalcohol, anisole, 1,4-dioxane, toluene, acetonitrile or N, N-dimethylformamide, preferred solvents are toluene, tert-butyl alcohol and dioxane in presence of a base such as MOH, $M_2CO_3$, $M_3PO_4$, AlkOM where M is alkali metal such as sodium, potassium, cesium, barium, preferred bases are $K_2CO_3$, $K_3PO_4$, tBuOK. The reaction is carried out at a temperature of from −20° C. to 150° C., preferably from ambient temperature to 100° C.

2) Compounds of formula II can be prepared by reacting compounds of formula IV in presence of a reducing metal such as iron, zinc, magnesium, indium, preferably using zinc or iron in the presence of proton source such a HXa, where Xa is a halogen for example HCl, a carboxylic acid, for example acetic acid, or an ammonium salt, for example $NH_4Cl$ in a protic solvent such as alcohols, for example ethanol or methanol, or water. The reaction is carried out at a temperature of from −20° C. to 150° C., preferably from ambient temperature to 100° C.

3) Compounds of formula IV can be prepared by reacting compounds of formula V with nitromethane in presence of a base such as DBU, DBN, DABCO, MOH, $M_2CO_3$, $M_3PO_4$, AlkOM where M is alkali metal such as sodium, potassium, cesium, barium, preferred bases are DBU, NaOEt, $K_2CO_3$, $K_3PO_4$, tBuOK in a suitable solvents such a toluene, dichloroethane, dioxane, ethanol, methanol, 2-propanol. The reaction is carried out at a temperature of from −20° C. to 150° C., preferably from ambient temperature to 120° C.

4) Compounds of formula V can be prepared by reacting compounds of formula VI by reacting them with a suitable activating agent for example, $SOCl_2$, $CH_3SO_2Cl$, $(COCl)_2$, $POCl_3$ in presence of a base for example pyridine, $Et_3N$, DBU in a suitable aprotic solvent for example toluene, dioxane, acetonitrile. The reaction is carried out at a temperature of from −20° C. to 150° C., preferably from ambient temperature to 100° C.

5) Compounds of formula VI can be prepared by reacting compounds of formula VII by reacting them V with nitromethane in presence of a suitable base for example piperidine, diethyl amine, DBU, tetrabutyl ammonium fluoride, diethylzinc, activated alumina in a suitable solvent for example toluene or without solvents.

6) In the above descriptions reference to leaving groups includes leaving groups such as halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. the leaving group may be selected from —$N_2^+Cl^-$, —$N_2^+BF_4^-$, —$N_2^+Br^-$, —$N_2^+PF_6^-$) and phosphonate esters (e.g. —OP(O)(OR)$_2$, wherein R is methyl or ethyl).

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars.

Furthermore, the compounds of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount applied, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by the compounds of formula (I) include: coleopterans, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus otyzophilus, Lyctus bruneus, Aulacophora femoralis*; lepidopterans, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella*; hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental*; orthopterans, for example, *Blatella germanica, Periplaneta americana, Gtyllotalpa Africana, Locusta migratoria migratoriodes*; isopterans, for example, *Reticulitermes speratus, Coptotermes formosanus*; dipterans, for example, *Musca domestica, Aedes aegypti, Hylemia platura, Culex pipiens, Anopheles sinensis, Culex tritaeniorhynchus, Liriomyza trifolii*; acari, for example, *Tetranychus cinnabarinus, Tetranychus urticae, Panonychus citri, Aculops pelekassi, Tarsonemus* spp.; nematodes, for example, *Meloidogyne incognita, Bursaphelenchus lignicolus Mamiya et Kiyohara, Aphelenchoides besseyi, Heterodera glycines, Pratylenchus* spp.

Examples of further pest species which may be controlled by the compounds of formula (I) include: from the order of the Anoplura (Phthiraptera), for example, *Damalinia* spp., *Haematopinus* spp., *Linognathus* spp., *Pediculus* spp., *Trichodectes* spp.; from the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Blyobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*; from the class of the Bivalva, for example, *Dreissena* spp.; from the order of the Chilopoda, for example, *Geophilus* spp., *Scutigera* spp.; from the order of the Coleoptera, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Ctyptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus otyzophilus, Lixus* spp., *Lyctus* spp., *Meligethes aeneus, Melolontha melolontha, Migdolus* spp., *Monochamus* spp., *Naupactus xanthographus, Niptus hololeucus, Otyctes rhinoceros, Otyzaephilus surinamensis, Otiorrhynchus sulcatus, Oxycetonia jucunda, Phaedon cochleariae, Phyllophaga* spp., *Popillia japonica, Premnottypes* spp., *Psylliodes chtysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.; from the order of the Collembola, for example, *Onychiurus armatus*; from the order of the Dermaptera, for example, *Forficula auricularia*; from the order of the Diplopoda, for example, *Blaniulus guttulatus*; from the order of the Diptera, for example, *Aedes* spp., *Anopheles* spp., *Bibio hortulanus, Calliphora etythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp.,

*Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.; from the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale*, *Ancylostoma ceylanicum*, *Acylostoma braziliensis*, *Ancylostoma* spp., *Ascaris lumbricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichiura*, *Wuchereria bancrofti*; ft may be furthermore possible to control protozoa, such as *Eimeria*; from the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eutygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.; from the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicotyne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chtysomphalus ficus*, *Cicadulina mbila*, *Coccomytilus halli*, *Coccus* spp., *Ctyptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Etythroneura* spp., *Euscelis bilobatus*, *Geococcus coffeae*, *Homalodisca coagulata*, *Hyalopterus arundinis*, *ketya* spp., *Idiocerus* spp., *Idioscopus* spp., *Laodelphax striatellus*, *Lecanium* spp., *Lepidosaphes* spp., *Lipaphis etysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*; from the order of the Hymenoptera, for example, *Diprion* spp., *Hoplocampa* spp., *Lasius* spp., *Mono-morium pharaonic*, *Vespa* spp.; from the order of the Isopoda, for example, *Armadillidium vulgare*, *Oniscus asellus*, *Porcellio scaber*; from the order of the Isoptera, for example, *Reticulitermes* spp., *Odontotermes* spp.; from the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chtysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema otyzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.; from the order of the Orthoptera, for example, *Acheta domesticus*, *Blatta orientalis*, *Blattella germanica*, *Gtyllotalpa* spp., *Leucophaea maderae*, *Locusta* spp., *Melanoplus* spp., *Periplaneta americana*, *Schistocerca gregaria*; from the order of the Siphonaptera, for example, *Ceratophyllus* spp., *Xenopsylla cheopis*. From the order of the Symphyla, for example, *Scutigerella immaculata*; from the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.; from the order of the Thysanura, for example, *Lepisma saccharina*. The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

In particular, the compounds of the invention may be used to control the following pest species:

*Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniellaoccidentalis* (thrip), *Thrips* spp. (thrips), *Leptinotarsadecemlineata* (Colorado potato beetle), *Anthonomusgrandis* (boll weevil), *Aonidiella* spp. (scale insects), *Trialeurodes* spp. (white flies), *Bemisia tabaci* (white fly), *Ostrinianubilalis* (European corn borer), *Spodopteralittoralis* (cotton leafworm), *Heliothisvirescens* (tobacco budworm), *Helicoverpaarmigera* (cotton bollworm), *Helicoverpazea* (cotton bollworm), *Sylepta derogata* (cotton leaf roller), *Pierisbrassicae* (white butterfly), *Plutellaxylostella* (diamond back moth), *Agrotis* spp. (cutworms), *Chilosuppressalis* (rice stem borer), *Locustamigratoria* (locust), *Chortiocetesterminifera* (locust), *Diabrotica* spp. (rootworms), *Panonychu-*

*sulmi* (European red mite), *Panonychuscitri* (citrus red mite), *Tetranychusurticae* (two-spotted spider mite), *Tetranychuscinnabarinus* (carmine spider mite), *Phyllocoptrutaoleivora* (citrus rust mite), *Polyphagotarsonemuslatus* (broad mite), *Brevipalpus* spp. (flat mites), *Boophilus microplus* (cattle tick), *Dermacentorvariabilis* (American dog tick), *Ctenocephalidesfelis* (cat flea), *Liriomyza* spp. (leafminer), *Muscadomestica* (housefly), *Aedesaegypti* (mosquito), *Anopheles* spp. (mosquitoes), *Culex* spp. (mosquitoes), *Lucillia* spp. (blowflies), *Blattellagermanica* (cockroach), *Periplanetaamericana* (cockroach), *Blattaorientalis* (cockroach), termites of the Mastotermitidae (for example *Mastotermes* spp.), the Kalotermitidae (for example *Neotermes* spp.), the Rhinotermitidae (for example *Coptotermesformosanus, Reticulitermes flavipes, R. speratu, R. virginicus, R. hesperus,* and *R. santonensis*) and the Termitidae (for example *Globiter messulfureus*), Solenopsisgeminata (fire ant), *Monomoriumpharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans*(vinegar eelworm), *Trichostrongylus* spp. (gastro intestinal nematodes) and *Deroceras reticulatum* (slug).

The compound of formula I may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables, cucurbits and pulses (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables, cucurbits and pulses (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and cereals.

The compounds of the invention may be used on soybean to control, for example, *Elasmopalpus lignosellus, Diloboderus abderus, Diabrotica speciosa, Trialeurodes* spp., *Bemisia* spp., aphids, *Sternechus subsignatus*, Formicidae, *Agrotis ipsilon, Julus* spp., *Murgantia* spp., *Halyomorpha* spp., *Thyanta* spp., *Megascelis* ssp., *Procornitermes* ssp., Gtyllotalpidae, *Nezara viridula, Piezodorus* spp., *Acrosternum* spp., *Neomegalotomus* spp., *Cerotoma trifurcata, Popillia japonica, Edessa* spp., *Liogenys fuscus, Euschistus heros,* stalk borer, *Scaptocoris castanea, phyllophaga* spp., *Migdolus* spp., *Pseudoplusia includens, Anticarsia gemmatalis, Epinotia* spp., *Rachiplusia* spp., *Spodoptera* spp., *Bemisia tabaci, Tetranychus* spp., *Agriotes* spp., *Euschistus* spp. The compounds of the invention are preferably used on soybean to control *Diloboderus abderus, Diabrotica speciosa, Trialeurodes* spp., *Bemisia* spp., *Nezara viridula, Piezodorus* spp., *Acrosternum* spp., *Cerotoma trifurcata, Popillia japonica, Euschistus heros, Scaptocoris castanea, phyllophaga* spp., *Migdolus* spp., *Agriotes* spp., *Euschistus* spp.

The compounds of the invention may be used on corn to control, for example, *Euschistus heros, Euschistus* spp., *Dichelops furcatus, Diloboderus abderus, Thyanta* spp., *Elasmopalpus lignosellus, Halyomorpha* spp., *Spodoptera frugiperda, Nezara viridula, Cerotoma trifurcata, Popillia japonica, Agrotis ipsilon, Diabrotica speciosa,* aphids, Heteroptera, *Procornitermes* spp., *Scaptocoris castanea,* Formicidae, *Julus* ssp., *Dalbulus maidis, Diabrotica virgifera, Diabrotica* spp., *Mocis latipes, Bemisia tabaci, heliothis* spp., *Tetranychus* spp., thrips spp., *phyllophaga* spp., *Migdolus* spp., *scaptocoris* spp., *Liogenys fuscus, Spodoptera* spp., *Ostrinia* spp., *Sesamia* spp., wireworms, *Agriotes* spp., *Halotydeus destructor*. The compounds of the invention are preferably used on corn to control *Euschistus heros, Euschistus* spp., *Dichelops furcatus, Diloboderus abderus, Nezara viridula, Cerotoma trifurcata, Popillia japonica, Diabrotica speciosa, Diabrotica virgifera, Diabrotica* spp., *Tetranychus* spp., *Thrips* spp., *Phyllophaga* spp., *Migdolus* spp., *Scaptocoris* spp., *Agriotes* spp.

The compounds of the invention may be used on sugar cane to control, for example, *Sphenophorus* spp., termites, *Migdolus* spp., *Diloboderus* spp., *Telchin licus, Diatrea saccharalis, Mahanarva* spp., Mealybugs.

The compounds of the invention may be used on alfalfa to control, for example, *Hypera brunneipennis, Hypera postica, Colias eutytheme, Collops* spp., *Empoasca solana, Epitrix* spp., *Geocoris* spp., *Lygus hesperus, Lygus lineolarzs, Spissistilus* spp., *Spodoptera* spp., Aphids, *Trichoplusia ni.* The compounds of the invention are preferably used on alfalfa to control *Hypera brunneipennis, Hypera postica, Empoasca solana, Epitrix* spp., *Lygus hesperus, Lygus lineolarzs, Trichoplusia ni.*

The compounds of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca* spp., thrips spp., *Delia* spp., *Murgantia* spp., *Trialeurodes* spp., *Bemisia* spp., *Microtheca* spp., Aphids. The compounds of the invention are preferably used on brassicas to control *Plutella xylostella, Pieris* spp., *Plusia* spp., *Trichoplusia ni, Phyllotreta* spp., *Thrips* spp.

The compounds of the invention may be used on oil seed rape, e.g. canola, to control, for example, *Meligethes* spp., *Ceutorhynchus napi, Halotydeus destructor, Psylloides* spp.

The compounds of the invention may be used on potatoes, including sweet potatoes, to control, for example, *Empoasca* spp., *Leptinotarsa* spp., *Diabrotica speciosa, Phthorimaea* spp., *Paratrioza* spp., *Maladera matrida, Agriotes* spp., Aphids, wireworms. The compounds of the invention are preferably used on potatoes, including sweet potatoes, to control *Empoasca* spp., *Leptinotarsa* spp., *Diabrotica speciosa, Phthorimaea* spp., *Paratrioza* spp., *Agriotes* spp.

The compounds of the invention may be used on cotton to control, for example, *Anthonomus grandis, Pectinophora* spp., *heliothis* spp., *Spodoptera* spp., *Tetranychus* spp., *Empoasca* spp., *Thrips* spp., *Bemisia tabaci, Trialeurodes* spp., Aphids, *Lygus* spp., *phyllophaga* spp., *Scaptocoris* spp., *Austroasca viridigrisea, Creontiades* spp., *Nezara* spp., *Piezodorus* spp., *Halotydeus destructor, Oxycaraenus hyalinipennis, Dysdercus cingulatus.* The compounds of the invention are preferably used on cotton to control *Anthonomus grandis, Tetranychus* spp., *Empoasca* spp., thrips spp., *Lygus* spp., *phyllophaga* spp., *Scaptocoris* spp.

The compounds of the invention may be used on rice to control, for example, *Leptocorisa* spp., *Cnaphalocrosis* spp., *Chilo* spp., *Scirpophaga* spp., *Lissorhoptrus* spp., *Oebalus pugnax, Scotinophara* spp., *Nephotettix malayanus, Nephotettix nigropictus, Nephotettix parvus, Nephottetix virescens, Nephotettix* spp., Mealybugs, *Sogatella furcifera, Nilaparvata lugens, Orseolia* spp., *Cnaphalocrocis medinalis, Marasmia* spp., *Stenchaetothrips biformis, Thrips* spp., *Hydrellia philippina*, Grasshoppers, *Pomacea canaliculata, Scirpophaga innotata, Chilo suppressalis, Chilo auricilius, Chilo polychtysus, Sesamia inferens, Laodelphax striatellus, Nymphula depunctalis, Oulema otyzae*, Stinkbugs. The compounds of the invention are preferably used on rice to control *Leptocorisa* spp., *Lissorhoptrus* spp., *Oebalus pugnax, Nephotettix malayanus, Nephotettix nigropictus, Nephotettix parvus, Nephottetix virescens, Nephotettix* spp., *Sogatella furcifera, Stenchaetothrips biformis, Thrips* spp., *Hydrellia philippina*, Grasshoppers, *Pomacea canaliculata, Scirpophaga innotata, Chilo suppressalis, Chilo polychtysus, Oulema otyzae*.

The compounds of the invention may be used on coffee to control, for example, *Hypothenemus Hampei, Perileucoptera Coffeella, Tetranychus* spp., *Brevipalpus* spp., Mealybugs. The compounds of the invention are preferably used on coffee to control Hypothenemus *Hampei, Perileucoptera Coffeella*.

The compounds of the invention may be used on citrus to control, for example, *Panonychus citri, Phyllocoptruta oleivora, Brevipalpus* spp., *Diaphorina citri, Scirtothrips* spp., *Thrips* spp., *Unaspis* spp., *Ceratitis capitata, Phyllocnistis* spp., Aphids, Hardscales, Softscales, Mealybugs. The compounds of the invention are preferably used on citrus to control *Panonychus citri, Phyllocoptruta oleivora, Brevipalpus* spp., *Diaphorina citri, Scirtothrips* spp., thrips spp., *Phyllocnistis* spp.

The compounds of the invention may be used on almonds to control, for example, *Amyelois transitella, Tetranychus* spp.

The compounds of the invention may be used on fruiting vegetables, cucurbits and pulses, including tomatoes, pepper, chili, eggplant, cucumber, squash etc., to control, for example, *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., *Aphids, Paratrioza* spp., *Frankliniella occidentalis, Frankliniella* spp., *Anthonomus* spp., *Phyllotreta* spp., *Amrasca* spp., *Epilachna* spp., *Halyomorpha* spp., *Scirtothrips* spp., *Leucinodes* spp., *Neoleucinodes* spp. *Maruca* spp., Fruit flies, Stinkbugs, *Lepidopteras, Coleopteras*. The compounds of the invention are preferably used on fruiting vegetables, cucurbits and pulses, including tomatoes, pepper, chili, eggplant, cucumber, squash etc., to control *Thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp.

The compounds of the invention may be used on tea to control, for example, *Pseudaulacaspis* spp., *Empoasca* spp., *Scirtothrips* spp., *Caloptilia theivora, Tetranychus* spp. The compounds of the invention are preferably used on tea to control *Empoasca* spp., *Scirtothrips* spp.

The compounds of the invention may be used on bulb vegetables, including onion, leek etc. to control, for example, *Thrips* spp., *Spodoptera* spp., *heliothis* spp. The compounds of the invention are preferably used on bulb vegetables, including onion, leek etc. to control *Thrips* spp.

The compounds of the invention may be used on grapes to control, for example, *Empoasca* spp., *Lobesia* spp., *Eupoecilia ambiguella, Frankliniella* spp., *Thrips* spp., *Tetranychus* spp., *Rhipiphorothrips Cruentatus, Eotetranychus Willamettei, Etythroneura Elegantula, Scaphoides* spp., *Scelodonta strigicollis*, Mealybugs. The compounds of the invention are preferably used on grapes to control *Frankliniella* spp., *Thrips* spp., *Tetranychus* spp., *Rhipiphorothrips Cruentatus, Scaphoides* spp.

The compounds of the invention may be used on pome fruit, including apples, pears etc., to control, for example, *Cacopsylla* spp., *Psylla* spp., *Panonychus ulmi, Cydia pomonella, Lepidopteras*, Aphids, Hardscales, Softscales. The compounds of the invention are preferably used on pome fruit, including apples, pears etc., to control *Cacopsylla* spp., *Psylla* spp., *Panonychus ulmi*.

The compounds of the invention may be used on stone fruit to control, for example, *Grapholita molesta, Scirtothrips* spp., *Thrips* spp., *Frankliniella* spp., *Tetranychus* spp., Aphids, Hardscales, Softscales, Mealybugs. The compounds of the invention are preferably used on stone fruit to control *Scirtothrips* spp., *Thrips* spp., *Frankliniella* spp., *Tetranychus* spp.

The compounds of the invention may be used on cereals to control, for example, Aphids, Stinkbugs, earthmites, *Eutygaster integriceps, Zabrus tenebrioides, Anisoplia austriaca, Chaetocnema aridula, Phyllotreta* spp., *Oulema melanopus, Oscinella* spp., *Delia* spp., *Mayetiola* spp., *Contarinia* spp., *Cephus* spp., *Steneotarsonemus* spp., *Apamea* spp.

In another embodiment compounds of formula I and mixtures of the invention may be used on rice to control *Baliothrips biformis* (*Thrips*), *Chilo* spp. (e.g. *Chilo polychtysus* (Dark headed striped borer), *Chilo suppressalis* (Rice stemborer), *Chilo indicus* (Paddy stem borer), *Chilo polychtysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema otyzae* (Rice leafbeetle), *Leptocorsia acuta* (Rice bug), *Leptocorsia oratorius* (rice bug), *Lissorhoptrus otyzophilus* (rice water weevil), *Mythemina separata* (armyworm), *Nephottetix* spp. (Green leafhopper) (e.g. *Nephotettix cincticeps, Nephotettix malayanus, Nephotettix nigropictus, Nephotettix parvus, Nephottetix virescens*), *Nilaparvata lugens* (Brown Planthopper), *Nymphula depunctalis* (Rice caseworm), *Orseolia otyzae* (Rice Gall midge), *Oulema otyzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki*.

The compounds of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, *Thrips*, Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The compounds of formula (I) and mixture of the invention, in particular those in the tables above, may be used for soil applications, including as a seed application, to target at least the following: sucking pests such as aphids, *thrips*, brown plant hopper (e.g. on rice), sting bugs, white flies (e.g. on cotton and vegetables), mites; on soil pests such as corn rootworm, wireworms, white grubs, *zabrus*, termites (e.g. on sugar cane, soy, pasture), maggots, cabbage root fly, red legged earth mite; on lepidoptera, such as *spodoptera*, cutworms, *elasmoplpus, plutella* (e.g. brassica), stem borers, leaf miners, flea beetle, *Sternechus*; on nematicides, such as *Heterodera glycines* (e.g. on soybean), *Pratylenchus brachyurus* (e.g. on corn), *P. zeae* (e.g. on corn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The compounds of formula (I) and mixture of the invention, in particular those in the tables above may be used for seed applications at least on the following: soil grubs for corn, soybeans, sugarcane: *Migdolus* spp; *Phyllophaga* spp.; *Diloboderus* spp; *Cyclocephala* spp; *Lyogenys fuscus*; sugarcane weevils: *Sphenophorus levis* & *Metamasius hemipterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn rootworm for corn and potatoes: *Diabrotica* spp., seed Maggot: *Delia platura*; soil stinkbugs: *Scaptocoris castanea*; wireworms: *Agriotes* spp; *Athous* spp *Hipnodes* bicolor; *Ctenicera destructor; Limonius* corm; *Limonius californicus*; rice water weevil: *Lissorhoptrus otyzophilus*; Red Legged earth mites: *Halotydeus destructor.*

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

The compounds of the invention may be applied to plant parts. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive ("synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful compounds, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (corn producing Cry1Ab), Agrisure®RW (corn producing mCry3A), Agrisure® Viptera (corn hybrids producing Vip3Aa); Agrisure300GT (corn hybrids producing Cry1Ab and mCry3A); YieldGard® (corn hybrids producing the Cry1Ab protein), YieldGard® Plus (corn hybrids producing Cry1Ab and Cry3Bb1), Genuity® SmartStax® (corn hybrids with Cry1A.105, Cry2Ab2, Cry1F, Cry34/35, Cry3Bb); Herculex® I (corn hybrids producing Cry1Fa) and Herculex®RW (corn hybrids producing Cry34Ab1, Cry35Ab1 and the enzyme Phosphinothricin-N-Acetyltransferase [PAT]); NuCOTN®33B (cotton cultivars producing Cry1Ac), Bollgard®I (cotton cultivars producing Cry1Ac), Bollgard®II (cotton cultivars producing Cry1Ac and Cry2Ab2) and VIPCOT® (cotton cultivars producing a Vip3Aa). Soybean Cyst Nematode resistance soybean (SCN®—Syngenta) and soybean with Aphid resistant trait (AMT®) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4 D (e.g. Enlist®) (e.g. WO 2011066384), glyphosate (e.g. Roundup Ready®, Roundup Ready 2 Yield®), sulfonylurea (e.g. STS®), glufosinate (e.g. Liberty Link®, Ignite®), Dicamba (Monsanto), HPPD tolerance (e.g. isoxaflutole herbicide) (Bayer CropScience, Syngenta). Double or triple stacks of any of the traits described here are also of interest, including glyphosate and sulfonyl-urea tolerance ((e.g. Optimum GAT®), plants stacked with STS® and Roundup Ready® or plants stacked with STS® and Roundup Ready 2 Yield®), dicamba and glyphosate tolerance (Monsanto). Of particular interest are soybean plants carrying trains conferring resistance to 2.4D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

Examples of cotton transgenic events include MON 531/757/1076 (Bollgard I®—Monsanto), MON1445 (Roundup ready Cotton®—Monsanto), MON531×MON1445 (Bollgard I+RR®—Monsanto), MON15985 (Genuity Bollgard II Cotton®—Monsanto), MON88913 (Genuity RR FLEX Cotton®—Monsanto), MON15985×MON1445 (Genuity Bollgard II+RR FLEX Cotton®—Monsanto), MON15983× MON88913 (Genuity Bollgard II+RR FLEX Cotton®—Monsanto), MON15985 (FibreMax Bollgard II Cotton®—Monsanto), LL25 (FibreMax LL Cotton®—BCS Stoneville), GHB614 (FibreMax GlyTol Cotton®—BCS Stoneville), LL25×MON15985 (FibreMax LL Bollgard II Cotton® BCS Stoneville/Monsanto), GHB614×LL25 (FibreMax LL GlyTol Cotton®—BCS Stoneville), GHB614× LL25×MON15985 (FibreMax RR GlyTol Bollgard II Cotton®—BCS Stoneville), MON88913×MON15985 (FibreMax LL GlyTol Bollgard II Cotton®—Monsanto), MON88913 (FibreMax RR Flex Cotton®—Monsanto), GHB119+T304-40 (Twinlink®—BCS Stoneville), GHB119+T304-40×LL25×GHB614 (Twinlink LL GT®—BCS Stoneville), 3006-210-23×281-24-236 (PhytoGen Widestrike Insect Protection®—Dow), 3006-210-23×281-24-236×MON88913 (PhytoGen Widestrike Insect Protection+RR FLEX®—Dow/Monsanto), 3006-210-23×281-24-236×MON1445 ((PhytoGen Widestrike Insect Protection+ RR®—Dow/Monsanto), MON1445 (PhytoGen Roundup Ready®—Monsanto), MON88913 (PhytoGen Roundup Ready FLEX®—Monsanto), COT102×COT67B (Vipcot®—Syngenta), COT102×COT67B×MON88913 (Vipcot RR FLEX®—Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701× MON89788 (Genuity Roundup ready 2 Yield Soybeans®— Monsanto), MON89788 (Roundup Ready2Yield®, RR2Y®—Monsanto), MON87708 (Monsanto), 40-3-2 (Roundup Ready®, RR1®—Monsanto), MON87701 (Monsanto), DAS-68416 (Enlist Weed Control System®—Dow), DP356043 (Optimum GAT®—Pioneer), A5547-127 (LibertyLink Soybean®—Bayercropscience), A2704-12 (Bayercropscience), GU262 (Bayercropscience), W62 W98 (Bayercropscience), CRV127 (Cultivance®—BASF/EMBRAPA) SYHT0H2 (WO2012/082548).

Examples of Maize transgenic events include T25 (LibertyLink®, LL®—Bayerscropscience), DHT-1 (Dow), TC1507 (Herculex I®—Dow), DAS59122-7 (Herculex RW®—Dow), TC1507+DAS59122-7—Herculex Xtra®—Dow), TC1507×DAS-59122-7×NK603 (Herculex Xtra+ RR®—Dow), TC1507×DAS-59122-×MON88017× MON89034 (Genuity Smartstax corn®, Genuity Smartstax RIB Complete®—Monsanto/Dow), MON89034×NK603 (Genuity VT double PRO®—Monsanto), MON89034+ MON88017 (Genuity VT Triple PRO®—Monsanto), NK603 (Roundup Ready 2®, RR2®—Monsanto), MON810 (YieldGard BT®, Yieldgard Cornborer®—Monsanto), MON810×NK603 (YieldGard cornborer RR Corn 2®—Monasnto), MON810×MON863 (YieldGard Plus®—Monsanto), MON863×MON810×NK603 (YieldGard Plus+ RR Corn2®/YieldGard RR Maize®—Monsanto), MON863×NK603 (YieldGard Rotworm+RR Corn 2®—Monsanto), MON863 (YieldBard RW®—Monsanto), MON89034 (YieldGard RW®—Monsanto), MON88017 (YieldGard VT RW®—Monsanto), MON810+MON88017 (YieldGard VT Triple®—Monsanto), MON88017+ MON89034 (YieldGard VT Triple Pro®—Monsanto), Bt11+MIR604+GA21 (Agrisure 3000®—Syngenta), Bt11+ TC1507+MIR604+5307+GA21 (Syngenta), Bt11+ TC1507+MIR604+DAS59122+GA21 (Agrisure 3122®—Syngenta), BT11 (Agrisure CB®—Syngenta), GA21 (Agrisure GT®—Syngenta), MIR604 (Agrisure RW®—Syngenta), Bt11+MIR162 (Agrisure TL VIP®—Syngenta), BT11+MIR162+GA21 (Agrisure Viptra 3110®—Syngenta), BT11+MIR162+MIR604 (Agrisure™ 3100®—Syngenta), Event3272+BT11+MIR604+GA21 (Syngenta), BT11+ MIR1692+MIR604+GA21 (Agrisure Viptera 3111®—Syngenta), BT11+MIR162+TC1507+GA21 (Agrisure Viptera 3220®—Syngenta), BT11+MIR162+TC1507+ MIR604+5307+GA21 (Agrisure Viptera 3222®—Syngenta), MIR162 (Syngenta), BT11+GA21+MIR162+ MIR604+5307 (Syngenta), 5307 (Syngenta).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin, acrinathirin, etofenprox or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron, diafenthiuron, lufeneron, novaluron, noviflumuron or chlorfluazuron;

e) Organic tin compounds, such as cyhexatin, fenbutatin oxide or azocyclotin;

f) Pyrazoles, such as tebufenpyrad, tolfenpyrad, ethiprole, pyriprole, fipronil, and fenpyroximate;

g) Macrolides, such as avermectins or milbemycins, for example abamectin, emamectin benzoate, ivermectin, milbemycin, spinosad, azadirachtin, milbemectin, lepimectin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, or nithiazine;

m) Diacylhydrazines, such as tebufenozide, chromafenozide or methoxyfenozide;

n) Diphenyl ethers, such as diofenolan or pyriproxifen;

o) Pyrazolines such as Indoxacarb or metaflumizone;

p) Ketoenols, such as Spirotetramat, spirodiclofen or spiromesifen;

q) Diamides, such as flubendiamide, chlorantraniliprole (Rynaxypyr®) or cyantraniliprole;

r) Essential oils such as Bugoil®—(PlantImpact); or s) a compound selected from buprofezine, flonicamid, acequinocyl, bifenazate, cyenopyrafen, cyflumetofen, etoxazole, flometoquin, fluacrypyrim, fluensulfone, flufenerim, flupyradifuone, harpin, iodomethane, dodecadienol, pyridaben, pyridalyl, pyrimidifen, flupyradifurone, 4-[(6-Chloro-pyridin-3-ylmethyl)-(2,2-difluoro-ethyl)-amino]-5H-furan-2-one (DE 102006015467), CAS: 915972-17-7 (WO 2006129714; WO2011/147953; WO2011/147952), CAS: 26914-55-8 (WO 2007020986), chlorfenapyr, pymetrozine, sulfoxaflor and pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap) or hopper specific insecticides (combinations such as buprofezin) for use in rice may be employed. Alternatively insecticides or acaricides specific for particular insect species/stages may also be included in the compositions (for example acaricidal ovo-larvicides, to give combinations such as clofentezine, flubenzimine, hexythiazox or tetradifon; acaricidal motilicides, to give combinations such as dicofol or propargite; acaricides, to give combinations such as bromopropylate or chlorbenzilate; or growth regulators, such as hydramethylnon, cyromazine, methoprene, chlorfluazuron or diflubenzuron).

Examples of fungicidal compounds and combinations which may be included in the composition of the invention are (E)-N-methyl-2-[2-(2,5-dimethylphenoxymethyl) phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704) (e.g. acibenzolar-S-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim, chlorhydrate, carboxin, carpropamid, carvone, CGA41396, CGA41397, chinomethionate, chlorothalonil, chlorozolinate, clozylacon, copper containing compounds to give combinations such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)—N-benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-A1, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, N-[9-(dichloromethylene)-1,2,3,4-tetrahydro-1,4-methanonaphthalen-5-yl]-3-(difluoromethyl)-1-methyl-1H-pyrazole-4-carboxamide[1072957-71-1], 1-methyl-3-difluoromethyl-1H-pyrazole-4-carboxylic acid (2-dichloromethylene-3-ethyl-1-methyl-indan-4-yl)-amide, and 1-methyl-3-difluoromethyl-4H-pyrazole-4-carboxylic acid [2-(2,4-dichloro-phenyl)-2-methoxy-1-methyl-ethyl]-amide.

The active ingredients combinations described above comprising a compound selected of the invention, in particularly from Tables 1 to 176 and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

In addition, biological agents may be included in the composition of the invention e.g. *Baciullus* species such as *Bacillus firmus, Bacillus cereus, Bacillus subtilis*, and *Pasteuria* species such as *Pasteuria penetrans* and *Pasteuria nishizawae*. A suitable *Bacillus firmus* strain is strain CNCM I-1582 which is commercially available as BioNem™. A suitable *Bacillus cereus* strain is strain CNCM I-1562. Of both *Bacillus* strains more details can be found in U.S. Pat. No. 6,406,690. Other biological organisms that may be included in the compositions of the invention are bacteria such as *Streptomyces* spp. such as *S. avermitilis*, and fungi such as *Pochonia* spp. such as *P. chlamydosporia*. Also of interest are *Metarhizium* spp. such as *M. anisopliae*; *Pochonia* spp. such as *P. chlamydosporia*.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin ((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, Buprofezine pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following: imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide; more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone; even more preferably enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

Examples of ratios of the compound of formula I to any mixing partner described herein include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool), cultured fish, honeybees. By combating parasites, fatalities and performance reduction (in terms of meat, milk, wool, skins, eggs, etc.) are reduced, so that applying the compounds of the invention allows more economic and simple husbandry of animals.

By controlling these pests it is intended to reduce deaths and improve performance (in the case of meat, milk, wool, hides, eggs, honey and the like) and health of the host animal. Also, controlling parasites may help to prevent the transmittance of infectious agents, the term "controlling" referring to the veterinary field, meaning that the active compounds are effective in reducing the incidence of the respective parasite in an animal infected with such parasites to innocuous levels, e.g. the active compound is effective in killing the respective parasite, inhibiting its growth, or inhibiting its proliferation.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc. and protozoae, such as coccidia).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., Cimicidae or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites, e.g. insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like. These include e.g. flies such as *Haematobia* (Lyperosia) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola (Damalinia) bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Examples of species of animal health pests include those from the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eutysternus, Haematopinus suis, Pediculus humanus capitis, Pediculus humanus corporis, Phylloera vastatrix, Phthirus pubis, Solenopotes capillatus*; from the order of the Mallophagida and the suborders *Amblycerina* and *Ischnocerina*, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chtysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora etythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydro-* taea irritans, Hydrotaea albipuncta, Chtysomya chloropyga, Chtysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis*; from the order of the Heteropterida, for example *Cimex* spp., *Triatoma* spp., *Rhodnius* spp., *Panstrongylus* spp; from the order of the Blattarida, for example *Blatta orientalis, Periplaneta americana, Blattela germanica, Supella* spp. (e.g. *Suppella longipalpa*); from the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodoros moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae* (*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi; Gasterophilus* spp., *Stomoxys* spp., *Trichodectes* spp., *Rhodnius* spp., *Ctenocephalides canis, Cimx lecturius, Ctenocephalides felis, Lucilia cuprina*; examples of acari include *Ornithodoros* spp., *Ixodes* spp., *Boophilus* spp.

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration; or by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such as BHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The invention is now described by way of non-limiting Examples.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

The following abbreviations were used in this section: DMF: dimethylformamide; THF: tetrahydrofuran; EtOAc: ethyl acetate; s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, $[M+H]^+$=molecular mass of the molecular cation, $[M-H]^-$=molecular mass of the molecular anion.

The following LC-MS methods were used to characterize the s:

Method A

| MS | ACQUITY SQD Mass Spectrometer from Waters (Single quadrupole mass spectrometer) |
|---|---|
| | Ionisation method: Electrospray |
| | Polarity: positive ions |
| | Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700 |
| | Mass range: 100 to 800 Da |
| | DAD Wavelength range (nm): 210 to 400 |

| LC | Method Waters ACQUITY UPLC with the following HPLC gradient conditions (Solvent A: Water/Methanol 9:1, 0.1% formic acid and Solvent B: Acetonitrile, 0.1% formic acid ) |

| Time (min) | A% | B% | Flow (mL/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Method B:

| MS | LC-20AD Mass Spectrometer from Shimadzu (Single quadrupole mass spectrometer) |
|---|---|
| | Ionisation method: Electrospray |
| | Polarity: positive and negative ions, Capillary (kV) 1.50, Cone (V) unknown, Extractor (V) 5.00, Source Temperature (° C.) 200, Desolvation Temperature (° C.) 250, |
| | Cone gas Flow (1/Hr) 90, Desolvation gas Flow (1/Hr) 90, Mass range: 50 to 1000 Da |
| | DAD Wavelength range (nm): 210 to 400 |

| LC | Method Shimadzu with the following HPLC gradient conditions Solvent Gradient: (solvent A: water, 0.1% TFA and solvent B: acetonitrile, 0.1% TFA) |

| Time (min) | A% | B% | Flow (mL/min) |
|---|---|---|---|
| 0 | 90 | 10 | 1.00 |
| 15.00 | 0 | 100 | 1.00 |
| 25.00 | 0 | 100 | 1.00 |
| 27.00 | 90 | 10 | 1.00 |
| 36.00 | 90 | 10 | 1.00 |

EXAMPLE 1

4-[4-(3,5-dichlorophenyl)-4-(trifluoromethyl)-3H-pyrazol-2-yl]-2-methyl-N-[2-oxo-2-(2,2,2-trifluoro-ethylamino)ethyl]benzamide (A1)

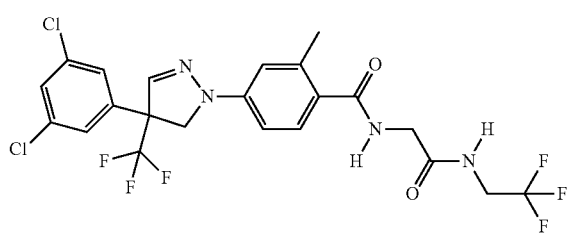 [SMILES: Cc1cc(N2CC(c3cc(Cl)cc(Cl)c3)(C(F)(F)F)C=N2)ccc1C(=O)NCC(=O)NCC(F)(F)F]

Step A: 2-(3,5-dichlorophenyl)-1,1,1-trifluoro-3-nitro-propan-2-ol

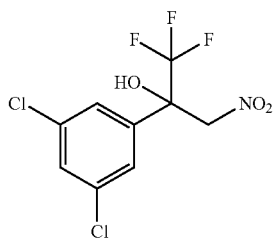 [SMILES: O=[N+]([O-])CC(O)(c1cc(Cl)cc(Cl)c1)C(F)(F)F]

A mixture of 1-(3,5-dichlorophenyl)-2,2,2-trifluoro-ethanone (12.1 g, 50 mmol), $CH_3NO_2$ (9.15 g, 150 mmol) and piperidine (0.85 g, 10 mmol) was stirred at 90° C. for 16 h. Then, the reaction mixture was poured into diluted hydrochloric acid and extracted with ethyl acetate three times. The combined organic layers were dried over Na$_2$SO$_4$, filtered and concentrated under reduced pressure. The residue was purified by column chromatography on silica gel to give 2-(3,5-dichlorophenyl)-1,1,1-trifluoro-3-nitro-propan-2-ol (9.09 g, 60%). $^1$H NMR (300 MHz, DMSO-d$_6$): δ5.13 (d, J=13.5 Hz, 1H), 5.82 (d, J=13.5 Hz, 1H), 7.70-7.71 (m, 1H), 7.75 (s, 2H), 8.12 (s, 1H); $^{19}$F NMR (282 MHz, DMSO-d$_6$): δ-72.4 s, 3F).

Step B: 1,3-dichloro-5-[(Z)-2-nitro-1-(trifluoromethyl)vinyl]benzene

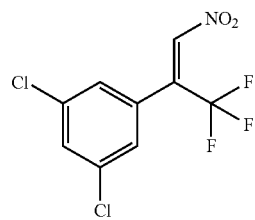 [SMILES: O=[N+]([O-])/C=C(/c1cc(Cl)cc(Cl)c1)C(F)(F)F]

To a solution of 2-(3,5-dichlorophenyl)-1,1,1-trifluoro-3-nitro-propan-2-ol (3.04 g, 10 mmol) in 100 mL of toluene at 0° C. was added SOCl$_2$ (5.95 g, 50 mmol) and then pyridine (1.58 g, 20 mmol). The mixture was then slowly warmed to room temperature. After stirring for another 3 h, the mixture was filtered. The filtrate was poured into diluter hydrochloric acid and extracted three times with ethyl acetate. The combined organic layers were washed with brine, dried over Na$_2$SO$_4$, filtered and concentrated under reduced pressure. The residue was purified by flash column chromatography on silica gel to give 1,3-dichloro-5-[(Z)-2-nitro-1-(trifluoromethyl)vinyl]benzene (1.71 g, 60% yield). $^1$H NMR (300 MHz, DMSO-d$_6$): δ 7.59 (s, 2H), 7.82-7.84 (m, 1H), 8.42-8.43 (m, 1H); $^{19}$F NMR (282 MHz, DMSO-d$_6$): δ-60.3 (s, 3F).

Step C: 1,3-dichloro-5-[2,2,2-trifluoro-1,1-bis(nitromethyl)ethyl]benzene

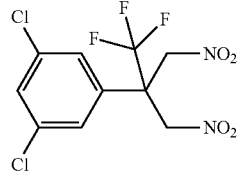 [SMILES: O=[N+]([O-])CC(C[N+](=O)[O-])(c1cc(Cl)cc(Cl)c1)C(F)(F)F]

Freshly prepared EtONa in EtOH (8 mL, 1 mol/L) was added to a solution of CH$_3$NO$_2$ (6.1 g, 100 mmol) in 40 mL of EtOH at room temperature. Then a solution of 1,3-dichloro-5-[(Z)-2-nitro-1-(trifluoromethyl)vinyl]benzene (5.7 g, 20 mmol) in 50 mL of EtOH was slowly added to the mixture. After the addition, the mixture was stirred for another 1 h and poured into diluted hydrochloric acid. The aqueous layer was extracted three times with ethyl acetate. The combined organic layers were dried over Na$_2$SO$_4$, filtered and concentrated under reduced pressure. The residue was purified by column chromatography on silica gel to give 1,3-dichloro-5-[2,2,2-trifluoro-1,1-bis(nitromethyl)ethyl]benzene (2.07 g, 30% yield). $^1$H NMR (300 MHz, DMSO-d$_6$): δ 5.69 (d, J=15.0 Hz, 2H), 5.88 (d, J=15.0 Hz, 2H), 7.77 (s, 1H), 7.86 (s, 2H); $^{19}$F NMR (282 MHz, DMSO-d$_6$): δ-64.5 (s, 3F).

Step D: 4-(3,5-dichlorophenyl)-4-(trifluoromethyl)-1,5-dihydropyrazole

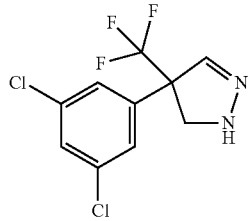 [SMILES: FC(F)(F)C1(c2cc(Cl)cc(Cl)c2)C=NNC1]

A mixture of 1,3-dichloro-5-[2,2,2-trifluoro-1,1-bis(nitromethyl)ethyl]benzene (2.77 g, 8 mmol), Zn powder (5.52 g, 80 mmol) and AcOH (4.8 g, 80 mmol) in 20 mL of MeOH was refluxed for 1 h. Then a saturated NaHCO$_3$ solution was added to the reaction mixture until the pH value reached 7. Then, ethyl acetate (100 mL) was added to the mixture. The resulting mixture was filtered and organic layer was separated. The aqueous layer was extracted with ethyl acetate twice. The combined organic layers were dried over Na$_2$SO$_4$, filtered and concentrated under reduced pressure. The residue was purified by flash column chromatography on silica gel to give 4-(3,5-dichlorophenyl)-4-(trifluoromethyl)-1,5-dihydropyrazole (246 mg, 10% yield). $^1$H NMR (300 MHz, CDCl$_3$): δ 3.75 (d, J=10.5, 1H), 3.98 (d, J=10.5, 1H), 7.01 (s, 1H), 7.24 (s, 2H), 7.38 (s, 1H); $^{19}$F NMR (282 MHz, CDCl$_3$): δ-69.5 (s, 3F); Mp: 96-98° C.

Step E. tert-butyl 4-[4-(3,5-dichlorophenyl)-4-(trifluoromethyl)-3H-pyrazol-2-yl]-2-methyl-benzoate

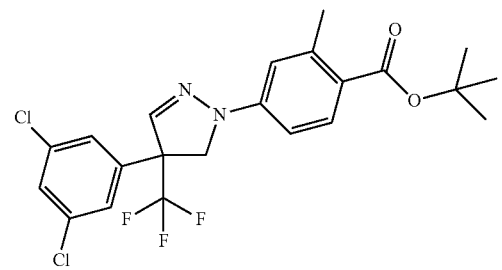 [SMILES: Cc1cc(N2CC(c3cc(Cl)cc(Cl)c3)(C(F)(F)F)C=N2)ccc1C(=O)OC(C)(C)C]

In a high-pressure vial, we introduce successively rac-2,2'-bis(diphenylphosphino)-1,1'-binaphthyl (0.002 mmol), tert-butyl 4-bromo-2-methyl-benzoate (0.03 mmol), sodium tert-butoxide (0.04 mmol), tris(dibenzylideneacetone)dipalladium (0.0007 mmol), 4-(3,5-dichlorophenyl)-4-(trifluoromethyl)-1,5-dihydropyrazole (8 mg, 0.03 mmol) and toluene (0.3 mL). After degassing by bubbling argon through the deep red solution for 15 min with stirring, the mixture was heated at 80° C. for 12 h.

After purification by column chromatography, using cyclohexane and EtOAc (0 to 20%), the tert-butyl 4-[4-(3,5-dichlorophenyl)-4-(trifluoromethyl)-3H-pyrazol-2-yl]-2-methyl-benzoate was isolated in 70% yield as a clear yellow oil. $^1$H-NMR (CDCl$_3$, 400 MHz): δ 1.52 (s, 9H), 2.50 (s, 3H), 4.05 (d, 1H), 4.30 (d, 1H), 6.97 (s, 1H), 6.81 (m, 2H), 7.20 (s, 2H), 7.36 (m, 1H), 7.80 (d, 1H). $^{19}$F-NMR (CDCl$_3$, 376 MHz): δ −70.8.

Step F: 4-[4-(3,5-dichlorophenyl)-4-(trifluoromethyl)-3H-pyrazol-2-yl]-2-methyl-benzoic acid

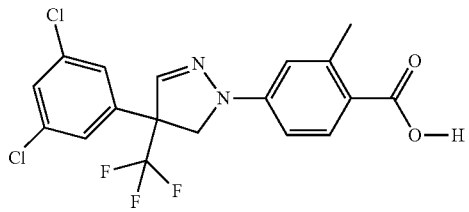 [SMILES: Cc1cc(N2CC(c3cc(Cl)cc(Cl)c3)(C(F)(F)F)C=N2)ccc1C(=O)O]

To a cooled solution (0 to 5° C.) of tert-butyl 4-[4-(3,5-dichlorophenyl)-4-(trifluoromethyl)-3H-pyrazol-2-yl]-2-methyl-benzoate (5 mg, 0.011 mmol) in dichloromethane (0.1 mol/L) was added trifluoroacetic acid (0.064 mmol). The resulting mixture was stirred for 6 h with the temperature maintained at 5° C. after which the volatile components were removed under reduced pressure. The resulting crude 4-[4-(3,5-dichlorophenyl)-4-(trifluoromethyl)-3H-pyrazol-2-yl]-2-methyl-benzoic acid (6 mg, 100% yield) was isolated as a yellow gum and used as such in the next step.

Step G: 4-[4-(3,5-dichlorophenyl)-4-(trifluoromethyl)-3H-pyrazol-2-yl]-2-methyl-N-[2-oxo-2-(2,2,2-trifluoroethylamino)ethyl]benzamide (A1)

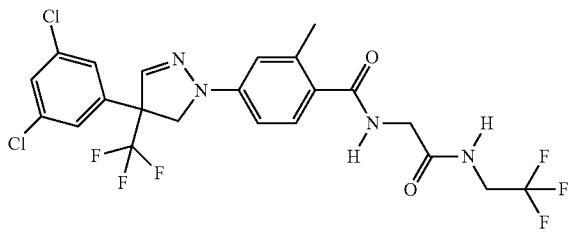 [SMILES: Cc1cc(N2CC(c3cc(Cl)cc(Cl)c3)(C(F)(F)F)C=N2)ccc1C(=O)NCC(=O)NCC(F)(F)F]

To a solution of 4-[(4S)-4-(3,5-dichlorophenyl)-4-(trifluoromethyl)-3H-pyrazol-2-yl]-2-methyl-benzoic acid (0.011 mmol) in $CH_2Cl_2$ (0.4 mL) at rt was added sequentially a catalytic amount of dimethylformamide, and oxalic chloride (0.05 mL). After stirring at rt for 3.5 h, the mixture was evaporated under reduced pressure. The resulting crude 4-[(4S)-4-(3,5-dichlorophenyl)-4-(trifluoromethyl)-3H-pyrazol-2-yl]-2-methyl-benzoyl chloride (0.0046 g, 0.011 mmol, 100% Yield) was isolated as a brown oil. To a solution of [2-oxo-2-(2,2,2-trifluoroethylamino)ethyl]ammonium; 2,2,2-trifluoroacetate (0.097 mmol, 16 mg) in $CH_2Cl_2$ (0.8 mL) at 0-5° C. was added $Et_3N$ (0.12 mL) followed by a solution of the 4-[(4S)-4-(3,5-dichlorophenyl)-4-(trifluoromethyl)-3H-pyrazol-2-yl]-2-methyl-benzoyl chloride (0.0046 g, 0.011 mmol) in $CH_2Cl_2$ (0.6 mL). After stirring for 2 h at rt, the mixture was purified directly by reverse phase column chromatography, which provided the desired 4-[4-(3,5-dichlorophenyl)-4-(trifluoromethyl)-3H-pyrazol-2-yl]-2-methyl-N-[2-oxo-2-(2,2,2-trifluoroethylamino)ethyl]benzamide as a white solid (2 mg).

LCMS (method A): RT 1.92 min, [M−H]+ 555/557; $^1$H-NMR (CDCl$_3$, 400 MHz): 2.52 (s, 3H), 3.97 (q, 2H), 4.13 (d, 1H), 4.18 (s, 2H), 4.38 (d, 1H), 6.55 (s, 1H), 6.94 (d, 1H), 6.95 (s, 1H), 7.03 (bs, 1H), 7.06 (s, 1H), 7.31 (m, 2H), 7.43 (s, 1H), 7.45 (d, 1H).
$^{19}$F-NMR (CDCl$_3$, 376 MHz): −70.8 (3F), −72.5 (3F).

EXAMPLE 2

N-cyclopropyl-4-[4-(3,5-dichlorophenyl)-4-(trifluoromethyl)-3H-pyrazol-2-yl]-2-methyl-benzamide (A2)

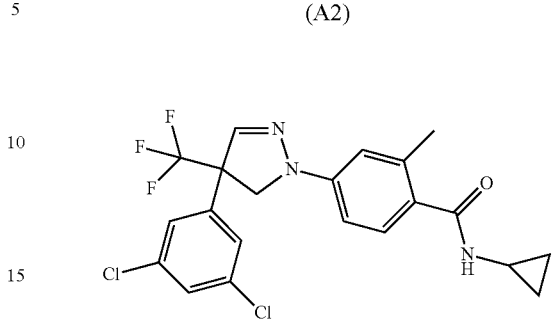

A mixture of 4-(3,5-dichlorophenyl)-4-(trifluoromethyl)-1,5-dihydropyrazole (200 mg, 0.72 mmol), 4-bromo-N-cyclopropyl-2-methyl-benzamide (213 mg, 0.84 mmol), Pd(OAc)$_2$ (16 mg, 0.07 mmol), Cs$_2$CO$_3$ (938 mg, 2.88 mmol) and 4,5-bis(diphenylphosphino)-9,9-dimethylxanthene (84 mg, 0.14 mmol) in 40 mL of toluene was stirred at 80° C. for 3 h under nitrogen protection. Then the reaction mixture was poured into water and extracted with ethyl acetate three times. The combined organic layers were dried over Na$_2$SO$_4$, filtered and concentrated under reduced pressure. The residue was purified by column chromatography on silica gel to give N-cyclopropyl-4-[4-(3,5-dichlorophenyl)-4-(trifluoromethyl)-3H-pyrazol-2-yl]-2-methyl-benzamide (75 mg, 22% yield). $^1$H NMR (300 MHz, DMSO-d$_6$): δ 0.48-0.50 (m, 2H), 0.61-0.64 (m, 2H), 2.33 (s, 3H), 2.75-2.78 (m, 1H), 4.42 (s, 2H), 6.90-6.92 (m, 2H), 7.24 (d, J=9.0 Hz, 1H), 7.72-7.74 (m, 3H), 7.85 (s, 1H), 8.06 (d, J=3.9 Hz, 1H); $^{19}$F NMR (282 MHz, CDCl$_3$): δ-66.9 (s, 3F); ESI-MS: 456 [M+H]+, 478 [M+Na]+; Mp: 85-88° C.

EXAMPLE 3

4-[4-(3,5-dichlorophenyl)-4-(trifluoromethyl)-3H-pyrazol-2-yl]-2-methyl-N-(2,2,2-trifluoroethyl)benzamide (A3)

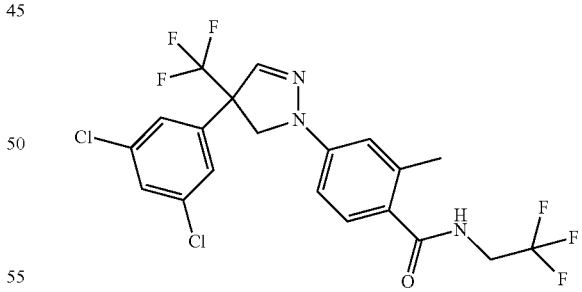

Under nitrogen, 4-(3,5-dichlorophenyl)-4-(trifluoromethyl)-4,5-dihydro-1H-pyrazole (example 1 step D, 150 mg, 0.55 mmol), 4-bromo-2-methyl-N-(2,2,2-trifluoroethyl)benzamide (187 mg, 0.63 mmol), Pd(OAc)$_2$ (12 mg, 0.05 mmol), cesium carbonate (704 mg, 2.16 mmol) and 2-dicyclohexylphosphino-2',4',6'-triisopropylbiphenyl(71 mg, 0.15 mmol) were dissolved in 30 ml of toluene. After the addition, the mixture was stirred at 80° C. for 3 h. Then, it was poured into water and extracted with ethyl acetate three times. The combined organic layers were dried over sodium sulfate, filtered and concentrated under reduced pressure.

The residue was purified by column chromatography on silica gel to provide 4-[4-(3,5-dichlorophenyl)-4-(trifluoromethyl)-3H-pyrazol-2-yl]-2-methyl-N-(2,2,2-trifluoroethyl)benzamide (140 mg, 52% yield). $^1$H NMR (300 Mz, CDCl$_3$): δ2.49 (s, 3H), 4.06-4.11 (m, 3H), 4.34-4.38 (d, 1H), 5.97 (t, 1H), 6.90-6.92 (d, 2H), 7.04 (s, 1H), 7.28 (s, 2H), 7.38-7.42 (m, 2H); $^{19}$F NMR (300 Mz, DMSO-d$_6$): δ −72.23−−72.17 (t, 3F), −70.67 (s, 3F); ESI-MS(+): 520 [M+Na]$^+$, M.p. 60-62° C.

The following compounds were prepared following a similar methods to that described in Examples 1 to 3.

TABLE A

Compounds of formal I-

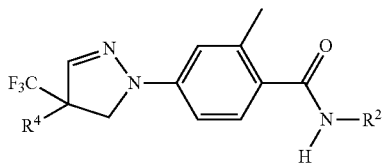

| Comp No. | R$^4$ | R$^2$ | LC/MS method | LC RT (min) | m/z (obsd) | M.P. (° C.) |
|---|---|---|---|---|---|---|
| A4 | 3,5-dichlorophenyl- | (4R)-2-ethyl-3-oxo-isoxazolidin-4-yl- | A | 1.14 | 529 [M + H]$^+$ | 153-155 |
| A5 | 3,5-dichlorophenyl- | 1-oxothietan-3-yl- | A | 1.06 | 504 [M + H]$^+$ | 100-103 |
| A6 | 3,5-dichlorophenyl- | 1,1-dioxothietan-3-yl- | A | 1.11 | 518 [M + H]$^+$ | 100-105 |
| A7 | 3,5-dichlorophenyl- | (E)-methoxyiminomethyl- | B | 16.76 | 495 [M + Na]$^+$ | 58-60 |
| A8 | 3,4,5-trichlorophenyl- | 2-oxo-2-(2,2,2-trifluoroethylamino)ethyl- | B | 16.77 | 589 [M + H]$^+$ | 88-90 |
| A9 | 3,4,5-trichlorophenyl- | (E)-methoxyiminomethyl- | B | 18.20 | 529 [M + Na]$^+$ | 100-102 |
| A10 | 3,4-dichloro-4-fluorophenyl- | 2-oxo-2-(2,2,2-trifluoroethylamino)ethyl- | B | 16.09 | 595 [M + Na]$^+$ | 156-158 |
| A11 | 3,4,5-trichlorophenyl- | 2,2,2-trifluoroethyl- | B | 17.76 | 530 [M − H]$^-$ | 72-74 |
| A12 | 3,5-dichloro-4-fluorophenyl- | (E)-methoxyiminomethyl- | B | 16.88 | 489 [M − H]$^-$ | 97-99 |
| A13 | 3,4,5-trichlorophenyl- | cyclobutyl- | B | 17.71 | 504 [M + H]$^+$ | 81-83 |
| A14 | 3,5-dichloro-4-fluorophenyl | cyclobutyl | B | 16.54 | 488 [M + H]$^+$ | 75-77 |
| A15 | 3,5-dichloro-4-fluorophenyl- | 2,2,2-trifluoroethyl- | B | 16.50 | 516 [M + H]$^+$ | 56-58 |
| A16 | 3,5-dichlorophenyl- | cyclobutyl- | B | 16.45 | 470 [M + H]$^+$ | 74-76 |

Biological Examples

*Spodoptera littoralis* (Egyptian Cotton Leafworm)

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT). Control of *Spodoptera littoralis* by a test sample is noted when at least one of mortality, antifeedant effect, and growth inhibition is higher than the untreated sample.

The following compound gave at least 80% control of *Spodoptera littoralis*: A1, A2, A3, A4, A5, A6, A7, A8, A9, A10, A11, A12, A13, A14, A15, A16

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation. Control of *Heliothis virescens* by a test sample is noted when at least one of egg mortality, larval mortality and growth inhibition is higher than the untreated sample.

The following compound gave at least 80% control of *Heliothis virescens*: A1, A2, A3, A4, A5, A6, A7, A8, A9, A10, A11, A12, A13, A14, A15, A16

*Plutella xylostella* (Diamond Back Moth):

24-well microtiter plate (MTP) with artificial diet was treated with test solutions at an application rate of 200 ppm (concentration in well 18 ppm) by pipetting. After drying, the MTPs were infested with L2 larvae (7-12 per well). After an incubation period of 6 days, samples were checked for larval mortality and growth regulation. Control of *Plutella xyllostella* by a test sample is noted when at least one of mortality and growth inhibition is higher than the untreated sample.

The following compound gave at least 80% control of *Plutella xylostella*: A1, A2, A3, A4, A5, A6, A7, A8, A9, A10, A11, A12, A13, A14, A15, A16

*Diabrotica balteata* (Corn Rootworm):

A 24-well microtiter plate (MTP) with artificial diet was treated with test solutions at an application rate of 200 ppm (concentration in well 18 ppm) by pipetting. After drying, the MTPs were infested with L2 larvae (6-10 per well). After an incubation period of 5 days, samples were checked for larval mortality and growth regulation. Control of *Diabrotica balteata* by a test sample is noted when at least one of larval mortality and growth inhibition is higher than the untreated sample.

The following compound gave at least 80% control of *Diabrotica balteata*: A1, A2, A3, A4, A5, A6, A7, A16

*Diabrotica balteata*, (Corn Rootworm)

Maize sprouts, placed on an agar layer in 24-well microtiter plates were sprayed at an application rate of 200 ppm.

After drying, the plates were infested with L2 larvae (6 to 10 per well). The samples were assessed for mortality and growth inhibition 4 days after infestation. Control of *Diabrotica balteata* by a test sample is noted when at least one of mortality and growth inhibition is higher than the untreated sample.

The following compound gave at least 80% control of *Diabrotica balteata*: A8, A9, A10, A11, A12, A13, A14, A15

*Thrips tabaci* (Onion *Thrips*):

Sunflower leaf discs were placed on agar in a 24-well microtiter plate and sprayed with test solutions at an application rate of 200 ppm. After drying, the leaf discs were infested with a *thrips* population of mixed ages. After an incubation period of 7 days, samples were checked for mortality.

The following compounds gave at least 80% control of *Thrips tabaci*: A1, A2, A3, A4, A5, A6, A7, A8, A9, A10, A11, A12, A13, A14, A15, A16

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality. Control of *Tetranychus urticae* by a test sample is noted when at least one of egg mortality, larval mortality, and adult mortality is higher than the untreated sample.

The following compound gave at least 80% control of *Tetranychus urticae*: A1, A2, A3, A4, A5, A6, A7, A8, A9, A10, A11, A12, A13, A14, A15, A16

The invention claimed is:

1. A compound of formula I

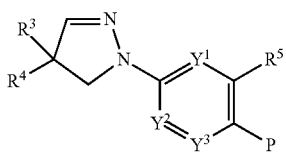

(I)

wherein
P is selected from P1 and P2, or P and $R^5$ together are P3

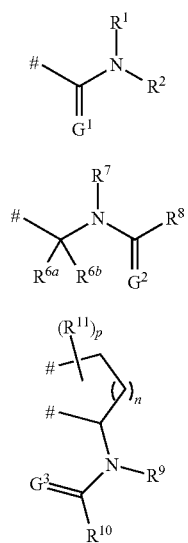

$Y^1$, $Y^2$, and $Y^3$ are independently of each other C—H, or C—$R^5$;
$G^1$ is oxygen or sulfur;
$G^2$ is oxygen or sulfur;
$G^3$ is oxygen or sulfur;
$R^1$ is hydrogen, $C_1$-$C_8$alkyl, $C_1$-$C_8$alkoxy, $C_1$-$C_6$alkylcarbonyl, or $C_1$-$C_8$alkoxycarbonyl;
$R^2$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-$C_1$-$C_4$alkylene or $C_3$-$C_{10}$cycloalkyl-$C_1$-$C_4$alkylene substituted by one to five $R^{13}$, aryl-$C_1$-$C_4$alkylene- or aryl-$C_1$-$C_4$alkylene-substituted by one to five $R^{14}$, heterocyclyl-$C_1$-$C_4$alkylene- or heterocyclyl-$C_1$-$C_4$alkylene-substituted by one to five $R^{14}$, aryl or aryl substituted by one to five $R^{14}$, heterocyclyl or heterocyclyl substituted by one to five $R^{14}$, $C_1$-$C_8$alkylaminocarbonyl-$C_1$-$C_4$alkylene, $C_1$-$C_8$haloalkylaminocarbonyl-$C_1$-$C_4$alkylene, $C_3$-$C_8$cycloalkyl-aminocarbonyl-$C_1$-$C_4$ alkylene, aryl-$CH_2$-aminocarbonyl-$C_1$-$C_4$alkylene or aryl-$CH_2$-aminocarbonyl-$C_1$-$C_4$alkylene wherein the aryl is substituted by one to five $R^{14}$, $C_1$-$C_8$alkylaminocarbonyl, $C_1$-$C_8$haloalkylaminocarbonyl, $C_3$-$C_6$cycloalkylaminocarbonyl, $C_1$-$C_6$alkyl-O—N=CH—, or $C_1$-$C_6$haloalkyl-O—N=CH—;
$R^3$ is $C_1$-$C_8$haloalkyl;
$R^4$ is aryl or aryl substituted by one to five $R^{15}$, or heteroaryl or heteroaryl substituted by one to five $R^{15}$;
each $R^5$ is independently hydrogen, halogen, cyano, nitro, $C_1$-$C_8$alkyl, $C_1$-$C_8$haloalkyl, $C_1$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl, or two $R^5$ on adjacent carbon atoms together form a —CH=CH—CH=CH— bridge or a —N=CH—CH=CH— bridge;
$R^{6a}$ and $R^{6b}$ are each independently hydrogen, halogen, cyano, $C_1$-$C_8$alkyl, $C_1$-$C_8$haloalkyl, or $C_3$-$C_8$cycloalkyl, or $R^{6a}$ and $R^{6b}$ together with the carbon atom to which they are attached may form a 3 to 6-membered carbocyclic ring;
$R^7$ is hydrogen, $C_1$-$C_8$alkyl, $C_1$-$C_8$alkoxy, $C_1$-$C_8$alkylcarbonyl, or $C_1$-$C_8$alkoxycarbonyl;
$R^8$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-$C_1$-$C_4$alkylene or $C_3$-$C_{10}$cycloalkyl-$C_1$-$C_4$alkylene substituted by one to five $R^{13}$, aryl-$C_1$-$C_4$alkylene- or aryl-$C_1$-$C_4$alkylene-substituted by one to five $R^{14}$, heterocyclyl-$C_1$-$C_4$alkylene- or heterocyclyl-$C_1$-$C_4$alkylene-substituted by one to five $R^{14}$, aryl or aryl substituted by one to five $R^{14}$, or heterocyclyl or heterocyclyl substituted by one to five $R^{14}$, each $R^9$ is independently hydrogen, $C_1$-$C_8$alkyl, $C_1$-$C_8$alkoxy, $C_1$-$C_8$alkylcarbonyl, or $C_1$-$C_8$alkoxycarbonyl;
$R^{10}$ is $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, $C_3$-$C_{10}$cycloalkyl-$C_1$-$C_4$alkylene or $C_3$-$C_{10}$cycloalkyl-$C_1$-$C_4$alkylene substituted by one to five $R^{13}$, aryl-$C_1$-$C_4$alkylene- or aryl-$C_1$-$C_4$alkylene-substituted by one to five $R^{14}$, heterocyclyl-$C_1$-$C_4$alkylene- or heterocyclyl-$C_1$-$C_4$alkylene-substituted by one to five $R^{14}$, aryl or aryl substituted by one to five $R^{14}$, heterocyclyl or heterocyclyl substituted by one to five $R^{14}$;
each $R^{11}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or $C_1$-$C_8$alkoxycarbonyl;

each $R^{12}$ is independently halogen, cyano, nitro, hydroxy, amino, $C_1$-$C_8$alkylamino, ($C_1$-$C_8$alkyl)$_2$amino, $C_1$-$C_8$alkylcarbonylamino, $C_1$-$C_8$haloalkylcarbonylamino, $C_1$-$C_8$alkoxy, $C_1$-$C_8$haloalkoxy, aryloxy or aryloxy substituted by one to five $R^{16}$, aryloxy-$C_1$-$C_4$alkylene or aryloxy-$C_1$-$C_4$alkylene wherein the aryl moiety is substituted by one to five $R^{16}$, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, aryl-$C_1$-$C_4$alkylthio or aryl-$C_1$-$C_4$alkylthio wherein the aryl moiety is substituted by one to five $R^{16}$;

each $R^{13}$ is independently halogen, cyano, $C_1$-$C_8$alkyl, $C_2$-$C_8$alkenyl, $C_2$-$C_8$alkynyl, or $C_1$-$C_8$alkoxy, $C_1$-$C_8$alkoxycarbonyl, or two $R^{13}$ are together $R^{19}$—O—N=;

each $R^{14}$ is independently halogen, cyano, nitro, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkylene, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylaminosulfonyl, ($C_1$-$C_8$alkyl)$_2$aminosulfonyl, $C_1$-$C_8$alkylcarbonyl, $C_1$-$C_8$haloalkylcarbonyl, $C_1$-$C_8$alkoxycarbonyl, $C_8$haloalkoxycarbonyl, aryl or aryl substituted by one to five $R^{16}$, heterocyclyl or heterocyclyl substituted by one to five $R^{16}$, aryl-$C_1$-$C_4$alkylene or aryl-$C_1$-$C_4$alkylene wherein the aryl moiety is substituted by one to five $R^{16}$, heterocyclyl-$C_1$-$C_4$alkylene or heterocyclyl-$C_1$-$C_4$alkylene wherein the heterocyclyl moiety is substituted by one to five $R^{16}$, aryloxy or aryloxy substituted by one to five $R^{16}$, or aryloxy-$C_1$-$C_4$alkylene or aryloxy-$C_1$-$C_4$alkylene wherein the aryl moiety is substituted by one to five $R^{16}$ or two $R^{14}$ are together =O;

each $R^{15}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or $C_1$-$C_8$alkoxycarbonyl;

each $R^{16}$ is independently halogen, cyano, nitro, $C_1$-$C_4$alkyl, $C_1$-$C_4$haloalkyl, $C_1$-$C_4$alkoxy, or $C_1$-$C_4$haloalkoxy;

each $R^{19}$ is hydrogen, $C_1$-$C_8$alkyl or $C_1$-$C_8$haloalkyl;

each Z is independently halogen, cyano, $C_1$-$C_8$alkyl or $C_1$-$C_8$alkyl substituted by one to five $R^{12}$, nitro, hydroxyl, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, or $C_1$-$C_8$haloalkylsulfonyl;

k is 0, 1, or 2;
n is 1 or 2;
p is 0, 1, 2, 3, 4, or 5;
or a salt or N-oxide thereof.

2. A compound according to claim 1, wherein P is P1.
3. A compound according to claim 1, wherein P is P2.
4. A compound according to claim 1, wherein P and $R^5$ together are P3.
5. A compound according to claim 1, wherein $Y^1$ is C—H or nitrogen, $Y^2$ and $Y^3$ are independently C—H or nitrogen; wherein no more than two of $Y^1$, $Y^2$ and $Y^3$ are nitrogen and wherein $Y^2$ and $Y^3$ are not both nitrogen.
6. A compound according to claim 1, wherein $G^1$, $G^2$ and $G^3$ are oxygen.
7. A compound according to claim 1, wherein $R^3$ is chlorodifluoromethyl or trifluoromethyl.
8. A compound according to claim 1, wherein $R^4$ is group (C)

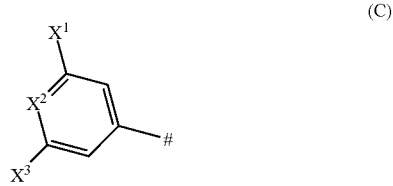

(C)

wherein $X^2$ is C—$X^6$ or nitrogen (preferably C—$X^6$); $X^1$, $X^3$ and $X^6$ are independently hydrogen, halogen or trihalomethyl.

9. A compound according to claim 1, wherein $R^5$ is hydrogen, chloro, bromo, fluoro, methyl or trifluoromethyl.

10. An insecticidal, acaricidal, nematicidal or molluscicidal composition comprising an insecticidally, acaricidally, nematicidally or molluscicidally effective amount of a compound of formula (I) as defined in claim 1.

11. An insecticidal, acaricidal, nematicidal or molluscicidal composition according to claim 10 comprising at least one additional compound having biological activity.

12. A combination product comprising a pesticidally effective amount of a component A and a pesticidally effective amount of component B, wherein component A is a compound of formula (I) as defined in claim 1, and compound B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide.

* * * * *